United States Patent
Aglietti et al.

(10) Patent No.: US 12,410,223 B2
(45) Date of Patent: Sep. 9, 2025

(54) TNF-ALPHA VARIANT FUSION MOLECULES

(71) Applicant: TREX BIO, INC., South San Francisco, CA (US)

(72) Inventors: Robin Allene Aglietti, South San Francisco, CA (US); Susannah Dale Barbee, San Francisco, CA (US); Peter Michael Bowers, La Jolla, CA (US); Melanie Angelika Kleinschek, San Francisco, CA (US)

(73) Assignee: TRex Bio, Inc., South San Francisco, CA (US)

( * ) Notice: Subject to any disclaimer, the term of this patent is extended or adjusted under 35 U.S.C. 154(b) by 0 days.

(21) Appl. No.: 18/942,121

(22) Filed: Nov. 8, 2024

(65) Prior Publication Data
US 2025/0122256 A1    Apr. 17, 2025

Related U.S. Application Data

(63) Continuation of application No. PCT/US2024/048933, filed on Sep. 27, 2024.

(60) Provisional application No. 63/586,809, filed on Sep. 29, 2023.

(51) Int. Cl.
| | |
|---|---|
| *A61K 38/19* | (2006.01) |
| *C07K 14/525* | (2006.01) |
| *C12N 5/10* | (2006.01) |
| *C12N 15/63* | (2006.01) |
| *A61K 38/00* | (2006.01) |

(52) U.S. Cl.
CPC .......... *C07K 14/525* (2013.01); *A61K 38/191* (2013.01); *C12N 5/10* (2013.01); *C12N 15/63* (2013.01); *A61K 38/00* (2013.01); *C07K 2319/30* (2013.01)

(58) Field of Classification Search
CPC .. C07K 14/525; C07K 19/00; C07K 2319/00; C07K 2319/30; A61K 38/191
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 4,816,567 A | 3/1989 | Cabilly et al. | |
| 5,597,899 A * | 1/1997 | Banner ................ | C07K 14/525 530/402 |
| 5,648,237 A | 7/1997 | Carter | |
| 5,739,277 A | 4/1998 | Presta et al. | |
| 5,789,199 A | 8/1998 | Joly et al. | |
| 5,840,523 A | 11/1998 | Simmons et al. | |
| 5,959,177 A | 9/1999 | Hein et al. | |
| 6,040,498 A | 3/2000 | Stomp et al. | |
| 6,133,426 A | 10/2000 | Gonzalez et al. | |
| 6,417,429 B1 | 7/2002 | Hein et al. | |
| 6,420,548 B1 | 7/2002 | Vezina et al. | |
| 6,946,292 B2 | 9/2005 | Kanda et al. | |
| 7,064,191 B2 | 6/2006 | Shinkawa et al. | |
| 7,125,978 B1 | 10/2006 | Vezina et al. | |
| 7,691,568 B2 | 4/2010 | Niwa et al. | |
| 7,700,099 B2 | 4/2010 | Strohl | |
| 7,749,753 B2 | 7/2010 | Kanda et al. | |
| 8,450,460 B2 | 5/2013 | Hill et al. | |
| 9,724,390 B2 | 8/2017 | Gurney | |
| 11,142,558 B2 | 10/2021 | Fischer et al. | |
| 11,530,247 B2 * | 12/2022 | Foster .................... | A61P 25/28 |
| 2003/0157108 A1 | 8/2003 | Presta | |
| 2004/0093621 A1 | 5/2004 | Shitara et al. | |
| 2004/0110704 A1 | 6/2004 | Yamane et al. | |
| 2004/0132140 A1 | 7/2004 | Satoh et al. | |
| 2005/0265962 A1 | 12/2005 | Desjarlais et al. | |
| 2011/0135657 A1 | 6/2011 | Hu et al. | |
| 2014/0322212 A1 | 10/2014 | Brogdon et al. | |
| 2015/0056159 A1 | 2/2015 | Kontermann et al. | |
| 2016/0222130 A1 | 8/2016 | Kamohara et al. | |
| 2017/0107270 A1 | 4/2017 | Pons et al. | |
| 2017/0320959 A1 | 11/2017 | Swanson et al. | |
| 2020/0102362 A1 | 4/2020 | Fischer et al. | |
| 2022/0026741 A1 | 1/2022 | Tranvouez-Bernardin et al. | |
| 2022/0267410 A1 * | 8/2022 | Fischer ................ | C07K 19/00 |

FOREIGN PATENT DOCUMENTS

| | | | |
|---|---|---|---|
| WO | 1997/11971 | A1 | 4/1997 |
| WO | 1999/058572 | A1 | 11/1999 |
| WO | 2004/42072 | A2 | 5/2004 |
| WO | 2007/106585 | A1 | 9/2007 |
| WO | 2008/079246 | A2 | 7/2008 |
| WO | 2010/010051 | A1 | 1/2010 |
| WO | 2015/148708 | A1 | 10/2015 |
| WO | 2016/070156 | A2 | 5/2016 |
| WO | 2016156291 | A1 | 10/2016 |

(Continued)

OTHER PUBLICATIONS

Shields et al. (2001) J. Biol. Chem. 276(9), 6591-6604.
Urlaub et al. (1980) Proc. Natl. Acad. Sci. USA 77: 4216-4220.
White et al. (2015) Cancer Cell 27, 138-148.
Xu et al., (2000) Cell Immunol. 200: 16-26.
Yamane-Ohnuki et al. (2004) Biotech. Bioeng. 87: 614-622.
Yazaki and Wu, Methods in Molecular Biology, vol. 248 (B.K.C. Lo, ed., Humana Press, Totowa, NJ), pp. 255-268 (2003).
Alegre et al. (1994) Transplantation 57: 1537-1543.
Angal et al. (1993) Mol Immunol. 30: 105-108.
Armour et al. (1999) Eur J Immunol 29: 2613-2624.
Armour et al. (2003) Mol. Immunol. 40: 585-593.

(Continued)

*Primary Examiner* — Bridget E Bunner
(74) *Attorney, Agent, or Firm* — Goodwin Procter LLP

(57) ABSTRACT

The present disclosure relates to TNF-alpha variants and TNF-alpha variant fusion molecules and therapeutic uses of such thereof.

23 Claims, 8 Drawing Sheets
Specification includes a Sequence Listing.

(56) References Cited

FOREIGN PATENT DOCUMENTS

| | | |
|---|---|---|
| WO | 2017/040312 A1 | 3/2017 |
| WO | 201822675 A1 | 2/2018 |
| WO | 2018185247 A1 | 10/2018 |
| WO | 2020260368 A1 | 12/2020 |
| WO | 2023095913 A1 | 6/2023 |
| WO | 2024200987 A1 | 10/2024 |
| WO | 2024200988 A1 | 10/2024 |
| WO | 2024201144 A1 | 10/2024 |
| WO | 2024204896 A1 | 10/2024 |
| WO | 2025068565 A1 | 4/2025 |

OTHER PUBLICATIONS

Bolt S et al. (1993) Eur J Immunol 23: 403-411.
Boschert et al. "Single chain TNF derivatives with individually mutated receptor binding sites reveal differential stoichiometry of ligand receptor complex formation for TNFR1 and TNFR2," Cellular Signaling 22 (2010) 1088-1096.
Brenner et at. Nat. Rev. Immunol. 15, 362-374 (2015).
Challener, BioPharm International-May 1, 2017 30(5): 30-31.
Chen, et al., 2013, Adv Drug Deliv Rev. 65(10): 1357-69.
Chopra et al. "Exogenous TNFR2 activation protects from acute GvHD via host T reg cell expansion," J. Exp. Med. Aug. 15, 2016, 2016, 1-20.
Chu et al. (2008) Mol Immunol. 45: 3926-3933.
Cole et al. (1999) Transplantation 68: 563-571.
Dong et al. "Essential protective role of tumor necrosis factor receptor 2 in neurodegeneration," PNAS, vol. 113, No. 43, Oct. 25, 2016, pp. 12304-12309.
Evans et al. (1987) J. Med. Chem., 30: 1229-1239.
Faustman and Davis. "TNF receptor 2 and disease: autoimmunity and regenerative medicine," Frontiers in Immunology, Dec. 2013, vol. 4, Article 478, pp. 1-8.
Faustman and Davis. "TNF receptor 2 pathway: drug target for autoimmune diseases," Nature Reviews, Jun. 2010, vol. 9, pp. 482-493.
Fischer et al. "A TNF Receptor 2 Selective Agonist Rescues Human Neurons from Oxidative Stress-Induced Cell Death," PLoS ONE Nov. 2011, vol. 6, Issue 11, pp. 1-11.
Fischer et al. "Astrocyte-Specific Activation of TNFR2 Promotes Oligodendrocyte Maturation by Secretion of Leukemia Inhibitory Factor," GLIA 2014; 62:272-283.
Fischer et al. "Novel strategies to mimic transmembrane tumor necrosis factor-dependent activation of tumor necrosis factor receptor 2," Scientific Reports, Jul. 26, 2017, 7:6607, 1-13.
Fischer et al. "Selective Activation of Tumor Necrosis Factor Receptor II Induces Anti-inflammatory Responses and Alleviates Experimental Arthritis," Arthritis & Rheumatology, vol. 70, No. 5, May 2018, 722-735.
Fischer et al. "Targeting sTNF-TNFR1 Signaling as a New Therapeutic Strategy," Antibodies 2015, 4, 48-70.
Gao et al. "Opposing Functions of Microglial and Macrophagic TNFR2 in the Pathogenesis of Experimental Autoimmune Encephalomyelitis," Cell Reports Jan. 3, 2017, 18, 198-212.
Gerngross (2004) Nat. Biotech. 22: 1409-1414.
Graham et al. (1977) J. Gen Virol. 36: 59-74.
Grell et al. Cell. 1995; 83(5): 793-802.
He et al. "A TNFR2-Agonist Faciliatates High Purity Expansion of Low Purity Treg Cells," PLoS ONE, May 25, 2016, vol. 11, Iss. 5, E01563311, pp. 1-17.
Hutchins et al. (1995) Proc Natl Acad Sci USA 92: 11980-11984.
Hutt et al. "Superior Properties of Fc-comprising scTRAIL Fusion Proteins," Mol Cancer Ther; 16(12) Dec. 2017, 2792-2802.
Kanda et al. (2006) Biotech. Bioeng. 94(4): 680-688.
Krippner-Heidenreich et al. "Single-Chain TNF, a TNF Derivative with Enhanced Stability and Antitumoral Activity," J Immunol 2008; 180:8176-8183.
Lazar et al. (2006) Proc Natl Acad Sci USA 103: 4005-4010.
Li et al. (2006) Nat. Biotech. 24: 210-215.
Lightle et al. Protein Sci. (2010) 19: 753-762.
Liu et al. "Pharmacokinetics of IgG1 monoclonal antibodies produced in humanized Pichia pastoris with specific glycoforms: A comparative study with CHO prodcued materials." Biologicals 39: 205-210 (2011).
Loetscher et al. "Human Tumor Necrosis Factor a (TNFa) Mutants with Exclusive Specificity for the 55-kDa or 75-kDa TNF Receptors," J. Bio. Chem., vol. 268, No. 36, Issue of Dec. 15, 1993, pp. 26360-26367.
Madsen et al. "Oligodendroglial TNFR2 Mediates Membrane TNF Dependent Repair in Experimental Autoimmune Encephalomyelitis by Promoting Oligodendrocyte Differentiation and Remyelination," Journal of Neuroscience, May 4, 2016, vol. 36, No. 18, pp. 5128-5413.
Mather (1980) Biol. Reprod. 23: 243-251.
Mather et al. (1982) Annals N. Y. Acad. Sci. 383:44-68.
McEarchern et al., (2007) Blood 109: 1185-1192.
Naismith et al. J Biol Chem (1995) 270:13303-7.
Oganesyan Vaheh et al. "Structural characterization of a human Fc fragment engineered for lack of effector functions," Acta Crystallographica Section D Biological Crystallography, vol. 64, No. 6, Jun. 1, 2008, pp. 700-704.
Okazaki et al. (2004) J. Mol. Biol. 336: 1239-1249.
Okubo et al. "Homogeneous Expansion of Human T-Regulatory Cells Via Tumor Necrosis Factor Receptor 2," Scientific Reports, Nov. 2013, 3:3153, 1-11.
Okubo et al. "Treg activation defect in type 1 diabetes: correction with TNFR2 agonism," Clinical & Translational Immunology (2016) 5, e56, 1-9.
Peters et al. (2012) J Biol Chem. 287(29): 24525-33.
Reddy et al. (2000) J. Immunol. 164: 1925-1933.
Ripka et al. (1986) Arch. Biochem. Biophys. 249: 533-545.
Rizo and Gierasch (1992) Ann. Rev. Biochem. 61: 387-418.
Sazinsky et al., (2008) Proc Natl Acad Sci USA 105: 20167-20172.
Seifert et al. "The IgM CH2 Domain as Covalently Linked Homodimerization Module for the Generation of Fusion Proteins with Dual Specificity," Protein Engineering, Design & Selection, Sep. 17, 2012, vol. 25, No. 10, pp. 603-612.

* cited by examiner

Binding to TNFR2 - expressing HEK cell line

TNF-ALPHA VARIANT FUSION MOLECULES

CROSS-REFERENCE

This application is a continuation of Application PCT/US2024/048933 filed on Sep. 27, 2024, which claims the benefit of and priority to U.S. Provisional Patent Application No. 63/586,809, filed Sep. 29, 2023. The entire contents of these applications are incorporated herein by reference in their entirety.

REFERENCE TO A SEQUENCE LISTING XML

This application contains a Sequence Listing which has been submitted electronically in XML format. The Sequence Listing XML is incorporated herein by reference. Said XML file, created on Sep. 27, 2024, is named TBI-011WO_SL.xml and is 63,100 bytes in size.

BACKGROUND

Tumor necrosis factor α (TNFα) is a pleiotropic cytokine which signals through TNF receptor 1 (TNFR1) and TNF receptor 2 (TNFR2). The extracellular domains of both receptors have similar a cysteine-rich motif that is repeated two to six times, are active as homodimers, but do not form TNFR1/TNFR2 heterodimers. See Naismith et al. *J Biol Chem* (1995) 270:13303-7. TNFR1 and TNFR2 are single transmembrane glycoproteins with 28% amino acid sequence identity mostly in their extracellular domain with both containing four tandemly repeated cysteine rich motifs. TNFR2 expression, in contrast to TNFR1, is restricted to lymphocytes. See Grell et al. Cell. 1995; 83(5):793-802. The two receptors are most divergent in the cytoplasmic domain, where TNFR1 has a death domain that is absent from TNFR2. See Brenner et al. *Nat. Rev. Immunol.* 15, 362-374 (2015).

TNFR1 is ubiquitously expressed on almost all cells, while TNFR2 exhibits a limited expression, predominantly on regulatory T cells (Tregs). TNFR2 plays a crucial role for human and mouse CD4$^+$FoxP3$^+$ Treg biology. Stimulation of TNFR2 maintains, activates, expands and stabilizes Tregs in inflammatory conditions and defines highly suppressive Tregs. TNFR2 regulates immune suppression in multiple diseases. See Dong et al. *Proc. Natl. Acad. Sci. USA.* 2016; 113:12304-12309; see also Fischer et al. *Arthritis Rheumatol.* 2018; 70:722-735.

All references cited herein, including patent applications and publications, are hereby incorporated by reference in their entirety.

BRIEF SUMMARY

Described herein, in certain embodiments, are TNF-alpha variants comprising a polypeptide that specifically binds to TNFR2, wherein the polypeptide comprises an amino acid sequence of SEQ ID NO: 10 or SEQ ID NO: 9. In some embodiments, the polypeptide comprises an amino acid sequence of SEQ ID NO: 10.

Described herein, in certain embodiments, are TNF-alpha variant molecules comprising one or more TNF-alpha variants described herein.

In some embodiments, the TNF-alpha variant molecule comprises a plurality of TNF-alpha variants, optionally at least three TNF-alpha variants.

In some embodiments, each TNF-alpha variant comprises three TNF-alpha variants, wherein one of the three TNF-alpha variants comprise a polypeptide comprising an amino acid sequence of SEQ ID NO: 9 and two of the three TNF-alpha variants comprise a polypeptide of an amino acid sequence of SEQ ID NO: 10.

In some embodiments, the TNF-alpha variant molecule comprises a linker between a TNF-alpha variant, optionally a linker comprising an amino acid sequence of SEQ ID NO: 16.

In some embodiments, the TNF-alpha variant molecule comprises one or more linkers.

In some embodiments, the TNF-alpha variant molecule comprises the amino acid sequence of SEQ ID NO: 15.

Described herein, in certain embodiments, are TNF-alpha variant fusion molecules comprising one or more TNF-alpha variant molecules described herein and an Fc domain.

In some embodiments of any of the TNF-alpha variant molecules, the TNF-alpha variant molecule comprises one or more TNF-alpha variant polypeptides comprising an amino acid sequence of SEQ ID NO: 9.

In some embodiments of any of the TNF-alpha variant molecules, the TNF-alpha variant molecule comprises one or more TNF-alpha variant polypeptides comprising an amino acid sequence of SEQ ID NO: 10.

In some embodiments of any of the TNF-alpha variant molecules, the TNF-alpha variant molecule comprises one or more TNF-alpha variant polypeptides comprising an amino sequence of SEQ ID NO: 9 and one or more TNF-alpha variant polypeptides comprising an amino acid sequence of SEQ ID NO: 10.

In some embodiments of any of the TNF-alpha variant molecules, the TNF-alpha variant molecule comprises one TNF-alpha variant comprising a polypeptide comprising an amino acid sequence of SEQ ID NO: 9 and two TNF-alpha variants a polypeptide comprising an amino acid sequence of SEQ ID NO: 10.

In some embodiments of any of the TNF-alpha variant molecules, the TNF-alpha variant molecule comprises one or two TNF-alpha variants comprising a polypeptide comprising an amino acid sequence of SEQ ID NO: 9 or SEQ ID NO: 10 and one or two TNF-alpha variants comprising a polypeptide comprising an amino acid sequence at least 80% (85%, 90%, 95%, 96%, 97%, 98%, 99%, or 100%) identical to any one of SEQ ID NOs: 3-8.

Described herein, in certain embodiments, are TNF-alpha variant fusion molecule comprising from N-terminus to C-terminus: a) a first TNF-alpha variant described herein; b) a first linker; c) a second TNF-alpha variant described herein; d) a second linker; e) a third TNF-alpha variant described herein; e) a third linker; and a Fc domain.

In some embodiments, the Fc domain is a human IgG1 isotype.

In some embodiments, the human IgG1 isotype Fc domain comprises a L234A mutation and a L235A mutation.

In some embodiments, the human IgG1 isotype Fc domain comprises a P331S mutation.

In some embodiments, the Fc domain has: a) reduced or eliminated binding to FcγRI, FcγRII, FcγRIII, or C1q; b) reduced or eliminated antibody-dependent cellular cytotoxicity (ADCC) and/or reduced complement binding activity; or any combination of a) and b). In some embodiments, the Fc domain comprises the amino acid sequence of SEQ ID NO: 17.

In some embodiments, the Fc domain is located at a C-terminus of the TNF-alpha variant fusion molecule. In some embodiments, the TNF-alpha variant fusion molecule comprises the amino acid sequence of SEQ ID NO: 23.

In some embodiments, the TNF-alpha variant fusion molecule comprises the amino acid sequence of SEQ ID NO: 23.

Described herein, in certain embodiments, are TNF-alpha variants, TNF-alpha variant molecules, or TNF-alpha variant fusion molecules described herein, wherein the TNF-alpha variant, TNF-alpha variant molecule, or TNF-alpha variant fusion molecule: a) binds to TNFR2 with over a 20 fold affinity compared TNFR1, optionally as determined by bio-layer interferometry; b) binds to and activates TNFR2 with an EC50 of at least about 5 ng/mL, optionally as determined by flow cytometry using human TNFR2 expressing (HEK293-NF-kB/Luc-TNFR2) cells and human TNFR2 non-expressing HEK293-NF-kB/Luc) cells; c) has increase Tm compared to SEQ ID NO: 21 or SEQ ID NO: 22, optionally as determined by differential scanning fluorimetry (DSF); d) has increased serum stability compared to SEQ ID NO: 21 or SEQ ID NO: 22, optionally as determined by Size Exclusion Chromatography; or e) any combinations of a)-d).

Described herein, in certain embodiments, is at least one isolated nucleic acid comprising a nucleic acid sequence that encodes the TNF-alpha variant, TNF-alpha variant molecule, or TNF-alpha variant fusion molecule described herein.

In some embodiments, the isolated nucleic acid encodes an amino acid sequence of SEQ ID NO: 23.

Described herein, in certain embodiments, is at least one expression vector comprising the isolated nucleic acid described herein.

Described herein, in certain embodiments, is at least one host cell comprising the isolated nucleic acid described herein or the expression vector described herein.

Described herein, in certain embodiments, is at least one host cell that expresses the TNF-alpha variant, TNF-alpha variant molecule, or TNF-alpha variant fusion molecule described herein.

Described herein, in certain embodiments, are methods of manufacturing the TNF-alpha variants, TNF-alpha variant molecules, or TNF-alpha variant fusion molecules described herein.

Described herein, in certain embodiments, are pharmaceutical compositions comprising the TNF-alpha variants, TNF-alpha variant molecules, or TNF-alpha variant fusion molecules described herein and a pharmaceutically acceptable carrier.

Described herein, in certain embodiments, are methods of treating an inflammatory disease or disorder, comprising administering to an individual with the inflammatory disorder the TNF-alpha variants, TNF-alpha variant molecules, or TNF-alpha variant fusion molecules described herein or the pharmaceutical compositions described herein.

In some embodiments, the inflammatory disease or disorder is selected from the group consisting of inflammatory bowel disease (IBD), ulcerative colitis, Crohn's disease, primary sclerosing cholangitis, celiac disease, atopic dermatitis, alopecia areata, vitiligo, dermatomyositis, hidradenitis suppurativa, systemic lupus erythematosus, rheumatoid arthritis, ankylosing spondylitis, multiple sclerosis, myasthenia gravis, Behcet's disease, or type I diabetes.

Described herein, in certain embodiments, are methods of treating a disease or disorder associated with dysregulation of Treg cells, autoreactive T cells, or by HLA-associated susceptibility, comprising administering to an individual with the inflammatory disorder the TNF-alpha variants, TNF-alpha variant molecules, or TNF-alpha variant fusion molecules described herein or the pharmaceutical compositions described herein.

Described herein, in certain embodiments, are methods for selectively activating TNFR2 in an individual, comprising administering to the individual the TNF-alpha variants, TNF-alpha variant molecules, or TNF-alpha variant fusion described herein or the pharmaceutical compositions described herein.

Described herein, in certain embodiments, are polypeptides comprising an amino acid sequence having at least 90% identity to the amino acid sequence of SEQ ID NO: 9 or SEQ ID NO: 10, and wherein the polypeptide comprises a tyrosine (Y) at amino acid position 143 and a glycine (G) at amino acid position 145 (corresponding amino acid position according to the amino acid sequence of SEQ ID NO: 9 and SEQ ID NO: 10).

It is to be understood that one, some, or all of the properties of the various embodiments described herein may be combined to form other embodiments of the present disclosure. These and other aspects of the disclosure will become apparent to one of skill in the art. These and other embodiments of the disclosure are further described by the detailed description that follows.

BRIEF DESCRIPTION OF FIGURES

FIG. 5A is a bar graph depicting the percentage of monomer retained in sample after 28 days of incubation for Variant 3 (D143N/A145R, black bar), Variant 4 (D143N/A145R, grey bar), Variant 5 (D143Y/A145G, black bar), or Variant 6 (D143Y/A145G, grey bar). FIG. 5B is a bar graph depicting, from left to right, the percentage of fragmentation in protein samples after 28 days of incubation for Variant 3 (D143N/A145R, C-terminal Fc), Variant 4 (D143N/A145R, N-terminal Fc), Variant 5 (D143Y/A145G, C-terminal Fc), or Variant 6 (D143Y/A145G, N-terminal Fc).

Figure 1:
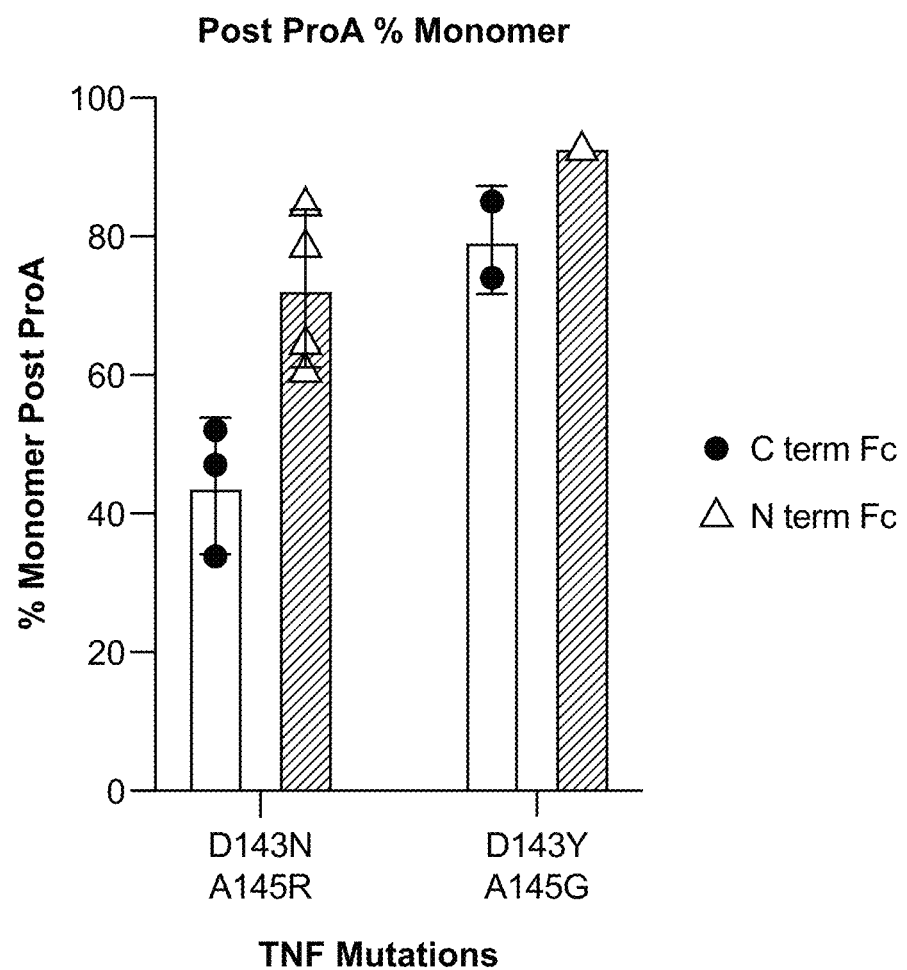
FIG. 1 is a bar graph depicting the percentage of monomer in samples comprising Variant 3 (D143N/A145R, dark grey bar), Variant 4 (D143N/A145R, light grey bar), Variant 5 (D143Y/A145G, dark grey bar), or Variant 6 (D143Y/A145G, light grey bar) TNF-alpha variant fusion molecules eluted under low-pH conditions from a Protein A column, as determined by HPLC-SEC.

With regards to the binding of a TNF-alpha variant and/or TNF-alpha variant fusion molecule to a target molecule, the term "specific binding" or "specifically binds" or is "specific for" a particular polypeptide means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide as used herein can be exhibited, for example, by a molecule having a KD for the target of about any of $10^{-4}$ M or lower, $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, $10^{-12}$ M or lower or a KD in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and KD values are inversely related. A high affinity for an antigen is measured by a low KD value. The test molecule specifically binds the target moiety if the binding affinity for the target moiety is at least 2-fold, or at least 3-fold, or at least 5-fold, or at least 10-fold stronger than the binding affinity for the control moiety. For the avoidance of doubt, specific binding does not require that a test molecule does not bind any other moieties.

An "amino-acid modification" at a specified position, e.g., of a TNF-alpha variant and/or TNF-alpha variant fusion molecule of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

Antibody "effector functions" refer to those biological activities attributable to the Fc region (a native sequence Fc region or amino acid sequence variant Fc region) of an antibody and vary with the antibody isotype.

The term "Fc region," "Fc domain," or "Fc" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" or "native sequence Fc domain" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region," "variant Fc domain," "variant Fc domain," or "variant Fc domain" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% amino acid sequence identity with a native sequence Fc region and/or with an Fc region of a parent polypeptide, and most preferably at least about 90% amino acid sequence identity therewith, more preferably at least about 95% amino acid sequence identity therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. Other FcRs, including those to be identified in the future, are encompassed by the term "FcR" herein. FcRs can also increase the serum half-life of antibodies. Binding to FcR in vivo and serum half-life of human FcR high-affinity binding polypeptides can be assayed, e.g., in transgenic mice or transfected human cell lines expressing human FcR, or in primates to which the polypeptides having a variant Fc region are administered. WO 2004/42072 (Presta) describes Fc region variants with improved or diminished binding to FcRs. See also, e.g., Shields et al., *J. Biol. Chem.* 9(2):6591-6604 (2001).

As used herein, "percent (%) amino acid sequence identity" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full-length of the sequences being compared.

An "TNFR2 agonist" as used herein is a TNF-alpha variant and/or TNF-alpha variant fusion molecule that increases, stimulates, and/or promotes one or more activities or functions of the TNFR2 after the variant or molecule binds the TNFR2. In some embodiments, the TNFR2 agonist is TNFR2 specific agonist.

An "isolated" fusion polypeptide, such as an isolated TNF-alpha variant and/or TNF-alpha variant fusion molecule of the present disclosure, is one that has been identified, separated and/or recovered from a component of its production environment {e.g., naturally or recombinantly). Preferably, the isolated fusion polypeptide is free of association with all other contaminant components from its production environment. Contaminant components from its production environment, such as those resulting from recombinant transfected cells, are materials that would typically interfere with research, diagnostic or therapeutic uses for the fusion polypeptide, and may include enzymes, hormones, and other proteinaceous or non-proteinaceous solutes. In preferred embodiments, the fusion polypeptide will be purified: (1) to greater than 95% by weight of TNF-alpha variant and/or TNF-alpha variant fusion molecule as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated fusion polypeptide includes the TNF-alpha variant and/or TNF-alpha variant fusion molecule in situ within recombinant T-cells since at least one component of the fusion polypeptide's natural environment will not be present. Ordinarily, however, an isolated fusion polypeptide will be prepared by at least one purification step.

An "isolated" nucleic acid molecule encoding a fusion polypeptide, such as a TNF-alpha variant molecule and/or a TNF-alpha variant fusion molecule of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the fusion polypeptides herein is in a form other than in the form or setting in which it is found in nature. Isolated nucleic acid molecules therefore are distinguished from nucleic acid encoding the fusion polypeptides herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of the present disclosure.

"Carriers" as used herein include pharmaceutically acceptable carriers, excipients, or stabilizers that are non-toxic to the cell or mammal being exposed thereto at the dosages and concentrations employed.

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

The terms "administer," "administering," "administration," and the like refer to methods that may be used to enable delivery of a therapeutic agent such as a TNF-alpha variant fusion molecule. Administration techniques that can be employed with the agents and methods described herein are found in e.g., Goodman and Gilman, The Pharmacological Basis of Therapeutics, current edition, Pergamon; and Remington's, Pharmaceutical Sciences, current edition, Mack Publishing Co., Easton, Pa.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

The terms "recipient," "individual," "subject," and "patient," are used interchangeably herein and in some embodiments, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human. None of these terms require the supervision of medical personnel.

As used herein, "in conjunction with" refers to administration of one treatment modality in addition to another treatment modality. As such, "in conjunction with" refers to administration of one treatment modality before, during, or after administration of the other treatment modality to the individual. Administration in conjunction also encompasses administration as a co-formulation or administration as separate compositions, including at different dosing frequencies or intervals, and using the same route of administration or different routes of administration. In some embodiments, administration in conjunction is administration as a part of the same treatment regimen.

As used herein, "About" a number, as used herein, refers to range including the number and ranging from 10% below that number to 10% above that number. "About" a range refers to 10% below the lower limit of the range, spanning to 10% above the upper limit of the range.

As used herein and in the appended claims, the singular forms "a," "an," and "the" include plural reference unless the context clearly indicates otherwise. For example, reference to a "fusion polypeptide" is a reference to from one to many fusion polypeptides, such as molar amounts, and includes equivalents thereof known to those skilled in the art, and so forth.

It is understood that aspects and embodiments of the present disclosure described herein include "comprising," "consisting," and "consisting essentially of" aspects and embodiments.

II. TNF-Alpha Variants and TNF-Alpha Variant Molecules a. TNF-Alpha Variants

Provided herein, in certain embodiments, are TNF-alpha variants which comprise a D143Y mutation and a A145G mutation (numbering according to the amino acid sequence of SEQ ID NO: 1). In some embodiments, TNF-alpha variants described herein specifically bind to TNFR2, e.g., specifically bind to TNFR2 compared to TNFR1. In some embodiments, the TNF-alpha variants specially bind to TNFR2 and selectively activate TNFR2, e.g., selectively active TNFR2 compared to TNFR1. In some embodiments, the TNF-alpha variants are primate or rodent TNF-alpha variants. In some embodiments, the TNF-alpha variants are human TNF-alpha variants. In some embodiments, the TNF-alpha variants are full-length unprocessed TNF-alpha variants or TNF-alpha variants that result from processing in the cell.

Provided herein, in certain embodiments, are TNF-alpha variants comprising a polypeptide that specifically binds to TNFR2, wherein the polypeptide comprises an amino acid sequence of SEQ ID NO: 9, functional fragments of SEQ ID NO: 9, and/or polypeptides comprising an amino acid sequence having at least 80% identity to SEQ ID NO: 9 and/or functional fragments of SEQ ID NO: 9, wherein such polypeptides comprises a tyrosine (Y) at amino acid position 143 and a glycine (G) at amino acid position 145, amino acid position according to the amino acid sequence of SEQ ID NO: 9.

In some embodiments, the polypeptide comprises an amino acid sequence having at least 80% (85%, 90%, 95%, 96%, 97%, 98%, 99%, or 100%) identity to the amino acid sequence of SEQ ID NO: 9, and wherein the polypeptide comprises a tyrosine (Y) at amino acid position 143 and a glycine (G) at amino acid position 145 (corresponding amino acid position according to the amino acid sequence of SEQ ID NO: 9). In some embodiments, the polypeptide comprises an amino acid sequence having at least 90% identity to the amino acid sequence of SEQ ID NO: 9, and wherein the polypeptide comprises a tyrosine (Y) at amino acid and a glycine (G) at amino acid position 145 (corresponding amino acid position according to the amino acid sequence of SEQ ID NO: 9). In some embodiments, the polypeptide comprises an amino acid sequence having at least 95% identity to the amino acid sequence of SEQ ID NO: 9, and wherein the polypeptide comprises a tyrosine (Y) at amino acid and a glycine (G) at amino acid position 145 (corresponding amino acid position according to the amino acid sequence of SEQ ID NO: 9). In some embodiments, the polypeptide comprises an amino acid sequence having at least 96% identity to the amino acid sequence of SEQ ID NO: 9, and wherein the polypeptide comprises a tyrosine (Y) at amino acid and a glycine (G) at amino acid position 145 (corresponding amino acid position according to the amino acid sequence of SEQ ID NO: 9). In some embodiments, the polypeptide comprises an amino acid sequence having at least 97% identity to the amino acid sequence of SEQ ID NO: 9, and wherein the polypeptide comprises a tyrosine (Y)

at amino acid and a glycine (G) at amino acid position 145 (corresponding amino acid position according to the amino acid sequence of SEQ ID NO: 9). In some embodiments, the polypeptide comprises an amino acid sequence having at least 98% identity to the amino acid sequence of SEQ ID NO: 9, and wherein the polypeptide comprises a tyrosine (Y) at amino acid and a glycine (G) at amino acid position 145 (corresponding amino acid position according to the amino acid sequence of SEQ ID NO: 9). In some embodiments, the polypeptide comprises an amino acid sequence having at least 99% identity to the amino acid sequence of SEQ ID NO: 9, and wherein the polypeptide comprises a tyrosine (Y) at amino acid and a glycine (G) at amino acid position 145 (corresponding amino acid position according to the amino acid sequence of SEQ ID NO: 9). In some embodiments, the polypeptide comprises an amino acid sequence having at least 99% identity to the amino acid sequence of SEQ ID NO: 9, and wherein the polypeptide comprises a tyrosine (Y) at amino acid and a glycine (G) at amino acid position 145 (corresponding amino acid position according to the amino acid sequence of SEQ ID NO: 9). In some embodiments, the polypeptide comprises an amino acid sequence of SEQ ID NO: 9.

In some embodiments of any of the foregoing, the TNF-alpha variants comprise a polypeptide that specifically binds to TNFR2, wherein the polypeptide comprises an amino acid sequence of a functional fragment of SEQ ID NO: 9, wherein the polypeptide comprises a tyrosine (Y) at amino acid and a glycine (G) at amino acid position 145 (corresponding amino acid position according to the amino acid sequence of SEQ ID NO: 9). In some embodiments, the polypeptide comprises an amino acid sequence of amino acids 2-157 of SEQ ID NO: 9. In some embodiments, the polypeptide comprises an amino acid sequence of amino acids 3-157 of SEQ ID NO: 9. In some embodiments, the polypeptide comprises an amino acid sequence of SEQ ID NO: 10. In some embodiments, the polypeptide comprises an amino acid sequence of amino acids 5-157 of SEQ ID NO: 9. In some embodiments, the polypeptide comprises an amino acid sequence of amino acids 6-157 of SEQ ID NO: 9.

In some embodiments, the polypeptide comprises an amino acid sequence at least 80% (85%, 90%, 95%, 96%, 97%, 98%, 99%, or 100%) identical to SEQ ID NO: 10. In some embodiments, the polypeptide comprises an amino acid sequence at least 80% identical to SEQ ID NO: 10. In some embodiments, the polypeptide comprises an amino acid sequence at least 90% identical SEQ ID NO: 10. In some embodiments, the polypeptide comprises an amino acid sequence at least 95% identical to SEQ ID NO: 10. In some embodiments, the polypeptide comprises an amino acid sequence at least 96% identical to SEQ ID NO: 10. In some embodiments, the polypeptide comprises an amino acid sequence at least 97% identical to SEQ ID NO: 10. In some embodiments, the polypeptide comprises an amino acid sequence at least 98% identical to SEQ ID NO: 10. In some embodiments, the polypeptide comprises an amino acid sequence at least 99% identical to SEQ ID NO: 10. In some embodiments, the polypeptide comprises an amino acid sequence 100% identical to SEQ ID NO: 10.

In some embodiments, the polypeptide further comprises one or more mutations described in WO2020260368, incorporated herein by reference in its entirety.

b. TNF-Alpha Variant Molecules

Provided herein, in certain embodiments, are TNF-alpha variant molecules. TNF-alpha variant molecules described herein can have specificity for TNFR2 and selectively activate TNFR2. In some embodiments, the TNF-alpha variant molecules comprise one or more TNF-alpha variants.

In some embodiments of any of the TNF-alpha variant molecules, the TNF-alpha variant molecule comprises one or more TNF-alpha variant polypeptides comprising an amino acid sequence of SEQ ID NO: 9. In some embodiments of any of the TNF-alpha variant molecules, the TNF-alpha variant molecule comprises one or more TNF-alpha variant polypeptides comprising an amino acid sequence of SEQ ID NO: 10. In some embodiments of any of the TNF-alpha variant molecules, the TNF-alpha variant molecule comprises one or more TNF-alpha variant polypeptides comprising an amino sequence of SEQ ID NO: 9 and one or more TNF-alpha variant polypeptides comprising an amino acid sequence of SEQ ID NO: 10. In some embodiments of any of the TNF-alpha variant molecules, the TNF-alpha variant molecule comprises one TNF-alpha variant comprising a polypeptide comprising an amino acid sequence of SEQ ID NO: 9 and two TNF-alpha variants a polypeptide comprising an amino acid sequence of SEQ ID NO: 10.

In some embodiments of any of the TNF-alpha variant molecules, the TNF-alpha variant molecule comprises one or more TNF-alpha variant polypeptides comprising an amino acid sequence comprising a D143N mutation and/or an A145R mutation, numbering according to the amino acid sequence of SEQ ID NO: 1. In some embodiments, the TNF alpha variant comprises an amino acid sequence at least 80% (85%, 90%, 95%, 96%, 97%, 98%, 99%, or 100%) identical to any one of SEQ ID NOs: 3-8. In some embodiments, the TNF alpha variant comprises an amino acid sequence at least 80% (85%, 90%, 95%, 96%, 97%, 98%, 99%, or 100%) identical to any one of SEQ ID NOs: 3-8, provided that the amino acid residue at position 143 of SEQ ID NOs: 3-8 is an asparagine (N) residue and/or the amino acid residue at position 145 of SEQ ID NOs: 3-8 is an arginine (R) residue, numbering according to the amino acid sequence of SEQ ID NO: 1.

In some embodiments, the TNF-alpha variant molecules comprise one, two, three, four, five, six, seven, eight, nine, ten, or more than ten TNF-alpha variants. In some embodiments, the TNF-alpha variant molecules comprise one TNF-alpha variant. In some embodiments, the TNF-alpha variant molecules comprise two TNF-alpha variants. In some embodiments, the TNF-alpha variant molecules comprise three TNF-alpha variants. In some embodiments, the TNF-alpha variant molecules comprise four TNF-alpha variants. In some embodiments, the TNF-alpha variant molecules comprise five TNF-alpha variants. In some embodiments, the TNF-alpha variant molecules comprise six TNF-alpha variants. In some embodiments, the TNF-alpha variant molecules comprise seven TNF-alpha variants. In some embodiments, the TNF-alpha variant molecules comprise eight TNF-alpha variants. In some embodiments, the TNF-alpha variant molecules comprise nine TNF-alpha variants. In some embodiments, the TNF-alpha variant molecules comprise ten TNF-alpha variants. In some embodiments, the TNF-alpha variants are the same. In some embodiments, the TNF-alpha variants are different.

In some embodiments, the TNF-alpha variant molecule comprises one or more linkers. In some embodiments, the linker is a peptide linker. In some embodiments, the peptide linker comprises a flexible peptide linker. In some embodiments, the peptide linker comprises a rigid peptide linker. In some embodiments, the peptide linker comprises a cleavable peptide linker. In some embodiments the linker is repeated once. In some embodiments the linker is repeated more than once. In some embodiments, the peptide linker comprises an amino acid sequence of SEQ ID NO: 16.

In some embodiments, the TNF-alpha variant molecule comprises at least three TNF-alpha variants and one or more linkers. In some embodiments, the one or more linkers is located between a first TNF-alpha variant of the at least three TNF-alpha variants and a second TNF-alpha variant of the at least three TNF-alpha variants and/or a second TNF-alpha variant of the at least three TNF-alpha variants and a third TNF-alpha variant of the at least three TNF-alpha variants. In some embodiments, a first linker of the one or more linkers is located between a first TNF-alpha variant of the at least three TNF-alpha variants and a second TNF-alpha variant of the at least three TNF-alpha variants. In some embodiments, a second linker of the one or more linkers is located between a second TNF-alpha variant of the at least three TNF-alpha variants and a third TNF-alpha variant of the at least three TNF-alpha variants.

In some embodiments, the TNF-alpha variant molecule comprises an amino acid sequence at least 80% (85%, 90%, 95%, 96%, 97%, 98%, 99%, or 100%) identical to SEQ ID NO: 15. In some embodiments, the TNF-alpha variant molecule comprises an amino acid sequence at least 80% identical to SEQ ID NO: 15. In some embodiments, the TNF-alpha variant molecule comprises an amino acid sequence at least 90% identical to SEQ ID NO: 15. In some embodiments, the TNF-alpha variant molecule comprises an amino acid sequence at least 95% identical to SEQ ID NO: 15. In some embodiments, the TNF-alpha variant molecule comprises an amino acid sequence at least 96% identical to SEQ ID NO: 15. In some embodiments, the TNF-alpha variant molecule comprises an amino acid sequence at least 97% identical to SEQ ID NO: 15. In some embodiments, the TNF-alpha variant molecule comprises an amino acid sequence at least 98% identical to SEQ ID NO: 15. In some embodiments, the TNF-alpha variant molecule comprises an amino acid sequence at least 99% identical to SEQ ID NO: 15. In some embodiments, the TNF-alpha variant molecule comprises an amino acid sequence at least 100% identical to SEQ ID NO: 15. In some embodiments, the TNF-alpha variant molecule comprises an amino acid sequence of SEQ ID NO: 15.

In some embodiments, the TNF-alpha variant molecule comprises an amino acid sequence at least 80% (85%, 90%, 95%, 96%, 97%, 98%, 99%, or 100%) identical to any one of SEQ ID NOs: 12-14.

Linker sequences can be used in the TNF-alpha variants and/or TNF-alpha variant fusion molecules to separate the different components (e.g., TNF-alpha variants, Fc domain).

In some embodiments, the linker is a peptide linker. In some embodiments, the peptide linker comprises a flexible peptide linker. In some embodiments, the peptide linker comprises a rigid peptide linker. In some embodiments, the peptide linker comprises a cleavable peptide linker. In some embodiments the linker is repeated once. In some embodiments the linker is repeated more than once. In some embodiments, the peptide linker comprises an amino acid sequence of SEQ ID NO: 16. In some embodiments, the peptide linker comprises GGGG (SEQ ID NO: 45). In some embodiments, the peptide linker comprises DKTHT (SEQ ID NO: 46).

In some embodiments, the linker comprises at least 5 to about 50 amino acids. In some embodiments, one or both of the linker and the second linker comprises about 5 to about 50 amino acids, about 5 to about 45 amino acids, about 5 to about 40 amino acids, about 5 to about 35 amino acids, about 5 to about 30 amino acids, about 5 to about 25 amino acids, about 5 to about 20 amino acids, about 5 to about 15 amino acids, about 5 to about 10 amino acids, about 10 to about 50 amino acids, about 15 to about 50 amino acids, about 20 to about 50 amino acids, about 25 to about 50 amino acids, about 30 to about 50 amino acids, about 35 to about 50 amino acids, about 40 to about 50 amino acids, or about 45 to about 50 amino acids.

In some embodiments, the linker comprises a sequence selected from the group consisting of $(GS)_n$ (SEQ ID NO: 47), $(G2S)_n$ (SEQ ID NO: 48), $(G3S)_n$ (SEQ ID NO: 49), $(G4S)_n$ (SEQ ID NO: 50), and $(G)_n$ (SEQ ID NO: 51), and wherein n is an integer from 2 to 20. In some embodiments, n is an integer from 2 to 18, from 2 to 16, from 2 to 14, from 2 to 12, from 2 to 10, from 2 to 8, from 2 to 6, from 2 to 4, from 4 to 20, from 6 to 20, from 8 to 20, from 10 to 20, from 12 to 20, from 14 to 20, from 16 to 20, or from 18 to 20.

In some embodiments, the linker comprises a sequence of GGGGG (SEQ ID NO: 25). In some embodiments, the linker comprises a sequence consisting of $(GGGGG)_n$ (SEQ ID NO: 52), and wherein n is an integer from 2 to 6.

In some embodiments, the linker comprises a sequence selected from GGSGGD (SEQ ID NO: 26) or GGSGGE (SEQ ID NO: 27). In some embodiments, the linker comprises a sequence selected from the group consisting of $(GGSGGD)_n$ (SEQ ID NO: 53) or $(GGSGGE)_n$ (SEQ ID NO: 54), and wherein n is an integer from 2 to 6.

In some embodiments, the linker comprises a sequence selected from the group consisting of GGGSGSGGGS (SEQ ID NO: 28) and GGGGGPGGGGP (SEQ ID NO: 29). In some embodiments, the linker comprises a sequence selected from the group consisting of $(GGGSGSGGGS)_n$ (SEQ ID NO: 55) and $(GGGGGPGGGGP)_n$ (SEQ ID NO: 56), and wherein n is an integer from 1 to 3.

In some embodiments, the linker comprises a sequence selected from the group consisting of GGGGGG (SEQ ID NO: 30) and GGGGGGGG (SEQ ID NO: 31).

In some embodiments, the linker comprises a sequence of EAAAK (SEQ ID NO: 32). In some embodiments, the linker comprises a sequence consisting of $(EAAAK)_n$ (SEQ ID NO: 57), and wherein n is an integer from 1 to 3. In some embodiments, the linker comprises a sequence of $A(EAAAK)_4ALEA(EAAAK)_4A$ (SEQ ID NO: 33). In some embodiments, the linker comprises a sequence of AEAAAKEAAAKA (SEQ ID NO: 34).

In some embodiments, the linker comprises a sequence of PAPA (SEQ ID NO: 35).

In some embodiments, the linker comprises a sequence of $(AP)_n$ (SEQ ID NO: 58), wherein n is an integer from 10 to 34.

In some embodiments, the linker comprises a cleavable linker. In some embodiments, the cleavable linker comprises a sequence of VSQTSKLTRAETVFPDV (SEQ ID NO: 36). In some embodiments, the cleavable linker comprises a sequence of PLGLWA (SEQ ID NO: 37). In some embodiments, the cleavable linker comprises a sequence of RVLAEA (SEQ ID NO: 38). In some embodiments, the cleavable linker comprises a sequence of EDVVCCSMSY (SEQ ID NO: 39). In some embodiments, the cleavable linker comprises a sequence of GGIEGRGS (SEQ ID NO: 40). In some embodiments, the cleavable linker comprises a sequence of TRHRQPRGWE (SEQ ID NO: 41). In some embodiments, the cleavable linker comprises a sequence of AGNRVRRSVG (SEQ ID NO: 42). In some embodiments, the cleavable linker comprises a sequence of RRRRRRRRR (SEQ ID NO: 43). In some embodiments, the cleavable linker comprises a sequence of GFLG (SEQ ID NO: 44).

In some embodiments, the linker comprises a sequence selected from the group consisting of $(GX)_n$, $(GGX)_n$, $(GGGX)_n$, $(GGGGX)_n$, and $(GzX)_n$, wherein z is between 1 and 20, and wherein n is at least 8. In some embodiments, z is between 2 and 18, 2 and 16, 2 and 14, 2 and 12, 2 and 10, 2 and 8, 2 and 6, 2 and 4, 4 and 20, 6 and 20, 8 and 20, 10 and 20, 12 and 20, 14 and 20, 16 and 20, or 18 and 20. In some embodiments, X is serine, aspartic acid, glutamic acid, threonine, or proline.

III. TNF-Alpha Variant Fusion Molecules

Provided herein, in certain embodiments, are TNF-alpha variant fusion molecules. TNF-alpha variant fusion molecules described herein can have specificity for TNFR2 and selectively activate TNFR2. In some embodiments, the TNF-alpha variant fusion molecules comprise a fusion partner (e.g., a polypeptide, a peptide, an antibody Fc domain, a polymer, a lipid, or other organic or inorganic moieties) linked to one or more TNF-alpha variant molecules. In some embodiments, the fusion partner of the TNF-alpha variant fusion molecule is located at the C-terminus of the TNF-alpha variant molecule. In some embodiments, the fusion partner of the TNF-alpha variant fusion molecule is located at the N-terminus of the TNF-alpha variant molecule.

Provided herein, in certain embodiments, are TNF-alpha variant fusion molecules comprising one or more TNF-alpha variants and an Fc domain.

Provided herein, in certain embodiments, are TNF-alpha variant fusion molecules comprising from N-terminus to C-terminus: a first TNF-alpha variant; a first linker; a second TNF-alpha variant; a second linker; a third TNF-alpha variant; a third linker; and a Fc domain.

In some embodiments, the TNF-alpha variant fusion molecule comprises an amino acid sequence at least 80% (85%, 90%, 95%, 96%, 97%, 98%, 99%, or 100%) identical to SEQ ID NO: 23. In some embodiments, the TNF-alpha variant fusion molecule comprises an amino acid sequence at least 80% identical to SEQ ID NO: 23. In some embodiments, the TNF-alpha variant fusion molecule comprises an amino acid sequence at least 90% identical to SEQ ID NO: 23. In some embodiments, the TNF-alpha variant fusion molecule comprises an amino acid sequence at least 95% identical to SEQ ID NO: 23. In some embodiments, the TNF-alpha variant fusion molecule comprises an amino acid sequence at least 96% identical to SEQ ID NO: 23. In some embodiments, the TNF-alpha variant fusion molecule comprises an amino acid sequence at least 97% identical to SEQ ID NO: 23. In some embodiments, the TNF-alpha variant fusion molecule comprises an amino acid sequence at least 98% identical to SEQ ID NO: 23. In some embodiments, the TNF-alpha variant fusion molecule comprises an amino acid sequence at least 99% identical to SEQ ID NO: 23. In some embodiments, the TNF-alpha variant fusion molecule comprises an amino acid sequence at least 100% identical to SEQ ID NO: 23. In some embodiments, the TNF-alpha variant fusion molecule comprises an amino acid sequence of SEQ ID NO: 23.

In some embodiments, the TNF-alpha variant fusion molecule comprises an amino acid sequence at least 80% (85%, 90%, 95%, 96%, 97%, 98%, 99%, or 100%) identical to SEQ ID NO: 24. In some embodiments, the TNF-alpha variant fusion molecule comprises an amino acid sequence at least 80% identical to SEQ ID NO: 24. In some embodiments, the TNF-alpha variant fusion molecule comprises an amino acid sequence at least 90% identical to SEQ ID NO: 24. In some embodiments, the TNF-alpha variant fusion molecule comprises an amino acid sequence at least 95% identical to SEQ ID NO: 24. In some embodiments, the TNF-alpha variant fusion molecule comprises an amino acid sequence at least 96% identical to SEQ ID NO: 24. In some embodiments, the TNF-alpha variant fusion molecule comprises an amino acid sequence at least 97% identical to SEQ ID NO: 24. In some embodiments, the TNF-alpha variant fusion molecule comprises an amino acid sequence at least 98% identical to SEQ ID NO: 24. In some embodiments, the TNF-alpha variant fusion molecule comprises an amino acid sequence at least 99% identical to SEQ ID NO: 24. In some embodiments, the TNF-alpha variant fusion molecule comprises an amino acid sequence at least 100% identical to SEQ ID NO: 24. In some embodiments, the TNF-alpha variant fusion molecule comprises an amino acid sequence of SEQ ID NO: 24.

In some embodiments, the TNF-alpha variant fusion molecule comprises an amino acid sequence at least 80% (85%, 90%, 95%, 96%, 97%, 98%, 99%, or 100%) identical to any one of SEQ ID NOs: 19-22.

In some embodiments, the Fc domain of the TNF-alpha variant fusion molecule is a multimer. In some embodiments, the Fc domain of the TNF-alpha variant fusion molecule is a dimer. In some embodiments, the Fc domain of the TNF-alpha variant fusion molecule is a trimer.

In some embodiments, the TNF-alpha variant fusion molecule described herein forms a homodimer of two TNF-alpha variant fusion molecules (e.g., dimerization through the Fc domain of the TNF-alpha variant fusion molecule).

a. Polymer, Lipid, and Other Organic or Inorganic Fusion Partners

In some embodiments of any of the TNF-alpha variant fusion molecules provided herein, the fusion partner is a polymer, lipid, or other organic or inorganic moiety. In certain embodiments, a fusion molecule can have a greater circulating half-life than a TNF-alpha variant molecule without a fusion partner. In certain embodiments, a TNF-alpha variant fusion molecule has improved targeting capacity for desired cells, tissues, and/or organs. In some embodiments, the fusion partner of the TNF-alpha variant fusion molecule comprises one or more water soluble polymer attachments, including, but not limited to, polyethylene glycol, polyoxyethylene glycol, or polypropylene glycol. See, e.g. U.S. Pat. Nos. 4,640,835, 4,496,689, 4,301,144, 4,670,417, 4,791,192 and 4,179,337. In certain embodiments, the fusion partner of the TNF-alpha variant fusion molecule comprises one or more polymer, including, but not limited to, monomethoxy-poly ethylene glycol, dextran, cellulose, copolymers of ethylene glycol/propylene glycol, carboxymethylcellulose, polyvinyl pyrrolidone, poly-1, 3-dioxolane, poly-1, 3, 6-trioxane, ethylene/maleic anhydride copolymer, polyaminoacids (either homopolymers or random copolymers), poly-(N-vinyl pyrrolidone)-poly ethylene glycol, propylene glycol homopolymers, a polypropylene oxide/ethylene oxide co-polymer, poly oxy ethylated polyols (e.g., glycerol) and polyvinyl alcohol, as well as mixtures of such polymers.

In certain embodiments, the fusion partner of the TNF-alpha variant fusion molecule modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for the fusion partner of the TNF-alpha variant fusion molecule. In certain embodiments, PEG is used to improve the therapeutic capacity for a protein. Certain such methods are discussed, for example, in U.S. Pat. No. 6,133,426, which is hereby incorporated by reference for any purpose.

b. Polypeptide or Peptide Fusion Partner

In some embodiments, the fusion partner of the TNF-alpha variant fusion molecule is a polypeptide or peptide. In some embodiment, the polypeptide or peptide comprises peptide analogs. Peptide analogs are commonly used in the pharmaceutical industry as non-peptide drugs with properties analogous to those of the template peptide. These types of non-peptide compound are termed "peptide mimetics" or "peptidomimetics." Fauchere, (1986) *J. Adv. Drug Res.,* 15:29; and Evans et al. (1987) *J. Med. Chem.,* 30:1229, which are incorporated herein by reference for any purpose. Such compounds are often developed with the aid of computerized molecular modeling. Peptide mimetics that are structurally similar to therapeutically useful peptides can be used to produce a similar therapeutic or prophylactic effect. Generally, peptidomimetics are structurally similar to a paradigm polypeptide (i.e., a polypeptide that has a biochemical property or pharmacological activity), such as human polypeptide, but have one or more peptide linkages optionally replaced by a linkage selected from: —CH2NH—, —CH2S—, —CH2-CH2-, —CH═CH-(cis and trans), —COCH2-, —CH(OH)CH2-, and —CH2SO—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo and Gierasch (1992) *Ann. Rev. Biochem.* 61:387, incorporated herein by reference for any purpose); for example, by adding internal cysteine residues capable of forming intramolecular disulfide bridges which cyclize the peptide.

c. FC Domain Fusion Partner

In some embodiments of any of the TNF-alpha variant fusion molecules provided herein, the fusion partner is an Fc domain. In some embodiments, the Fc domain is of the class IgA, IgD, IgE, IgG, or IgM. In some embodiments, the Fc domain is a human IgA1, IgA2, IgG1, IgG2, IgG3, or IgG4 isotype. In some embodiments, the Fc domain is a human IgG1 isotype. In some embodiments, the Fc domain is a human IgG2 isotype. In some embodiments, the Fc domain is a human IgG4 isotype. In some embodiments, the Fc domain is a hybrid of human IgA1, IgA2, IgG1, IgG2, IgG3, IgG4, or combinations thereof.

Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, MD, 1991.

In certain embodiments of any of the TNF-alpha variant fusion molecules, the Fc domain is human IgG1 isotype. In some embodiments, the TNF-alpha variant fusion molecule induces the one or more TNFR2 activities independently of binding to an Fc receptor. In some embodiments, the TNF-alpha variant fusion molecule binds an inhibitory Fc receptor. In certain embodiments, the inhibitory Fc receptor is inhibitory Fc-gamma receptor IIB (FcγIIB).

In certain embodiments of any of the TNF-alpha variant fusion molecules provided herein, the Fc domain has an IgG2 isotype. In some embodiments, the TNF-alpha variant fusion molecule induces the one or more TNFR2 activities or independently of binding to an Fc receptor. In some embodiments, the TNF-alpha variant fusion molecule binds an inhibitory Fc receptor. In certain embodiments, the inhibitory Fc receptor is inhibitory Fc-gamma receptor IIB (FcγIIB).

In certain embodiments of any of the TNF-alpha variant fusion molecules provided herein, the Fc domain has an IgG4 isotype. In certain embodiments, the inhibitory Fc receptor is inhibitory Fc-gamma receptor IIB (FcγIIB).

In certain embodiments of any of the TNF-alpha variant fusion molecules provided herein, the Fc domain has a hybrid IgG2/4 isotype. In some embodiments, the Fc domain includes an amino acid sequence comprising amino acids 118 to 260 according to EU numbering of human IgG2 and amino acids 261-447 according to EU numbering of human IgG4 (WO 1997/11971; WO 2007/106585).

In some embodiments of any of the TNF-alpha variant fusion molecules provided herein, the Fc domain comprises an amino acid sequence having at least 80% identity with an amino acid sequence according to SEQ ID NO: 17. In some embodiments of any of the TNF-alpha variant fusion molecules provided herein, the Fc domain comprises an amino acid sequence having at least 90% identity with an amino acid sequence according to SEQ ID NO: 17. In some embodiments of any of the TNF-alpha variant fusion molecules provided herein, the Fc domain comprises an amino acid sequence having at least 95% identity with an amino acid sequence according to SEQ ID NO: 17. In some embodiments of any of the TNF-alpha variant fusion molecules provided herein, the Fc domain comprises an amino acid sequence having at least 96% identity with an amino acid sequence according to SEQ ID NO: 17. In some embodiments of any of the TNF-alpha variant fusion molecules provided herein, the Fc domain comprises an amino acid sequence having at least 97% identity with an amino acid sequence according to SEQ ID NO: 17. In some embodiments of any of the TNF-alpha variant fusion molecules provided herein, the Fc domain comprises an amino acid sequence having at least 98% identity with an amino acid sequence according to SEQ ID NO: 17. In some embodiments of any of the TNF-alpha variant fusion molecules provided herein, the Fc domain comprises an amino acid sequence having at least 99% identity with an amino acid sequence according to SEQ ID NO: 17. In some embodiments of any of the TNF-alpha variant fusion molecules provided herein, the Fc domain comprises an amino acid sequence having at least 100% identity to SEQ ID NO: 17. In some embodiments of any of the TNF-alpha variant fusion molecules provided herein, the Fc domain comprises an amino acid sequence of SEQ ID NO: 17.

In some embodiments, the Fc domain comprises an Fc isotype and/or modified Fc domain. In some embodiments, the Fc isotype and/or modified Fc domain is capable of binding to Fc gamma receptor. In some embodiments, the modified Fc domain increases FcγRIIIa binding as compared to a corresponding antibody comprising an Fc region that does not comprise the amino acid substitutions. In some embodiments, the modified Fc domain decreases FcγRIIIa binding as compared to a corresponding antibody comprising an Fc region that does not comprise the amino acid substitutions. In some embodiments, the modified Fc domain increases FcγRIIa binding as compared to a corresponding antibody comprising an Fc region that does not comprise the amino acid substitutions. In some embodiments, the modified Fc domain increases FcγRIIb binding as compared to a corresponding antibody comprising an Fc region that does not comprise the amino acid substitutions. In some embodiments, the modified Fc domain decreases FcγRIIb binding as compared to a corresponding antibody comprising an Fc region that does not comprise the amino acid substitutions. In some embodiments, the modified Fc domain increases FcγRI binding as compared to a corresponding antibody comprising an Fc region that does not comprise the amino acid substitutions. In some embodiments, the modified Fc domain decreases FcγRI binding as compared to a corresponding antibody comprising an Fc region that does not comprise the amino acid substitutions. In some embodiments, the modified Fc domain increases C1q binding as compared to a corresponding antibody comprising an Fc region that does not comprise the amino acid substitutions. In some embodiments, the modified Fc domain increases C4b binding as compared to a corresponding antibody comprising an Fc region that does not comprise the amino acid substitutions. In some embodiments, the modified Fc domain increases hexamerization as compared to a corresponding antibody comprising an Fc region that does not comprise the amino acid substitutions. In some embodiments, the modified Fc domain deceases antibody glycosylation as compared to a corresponding antibody comprising an Fc region that does not comprise the amino acid substitutions. In some embodiments, the modified Fc domain increases FcRn binding at pH 6.0 as compared to a corresponding antibody comprising an Fc region that does not comprise the amino acid substitutions. In some embodiments, the modified Fc domain enhances antibody-dependent cell-mediated cytotoxicity (ADCC) as compared to a corresponding antibody comprising an Fc region that does not comprise the amino acid substitutions. In some embodiments, the modified Fc domain decreases antibody-dependent cell-mediated cytotoxicity (ADCC) as compared to a corresponding antibody comprising an Fc region that does not comprise the amino acid substitutions. In some embodiments, the modified Fc domain enhances antibody-dependent cellular phagocytosis (ADCP) as compared to a corresponding antibody comprising an Fc region that does not comprise the amino acid substitutions. In some embodiments, the modified Fc domain reduces antibody-dependent cellular phagocytosis (ADCP) as compared to a corresponding antibody comprising an Fc region that does not comprise the amino acid substitutions. In some embodiments, the modified Fc domain enhances complement-dependent cytotoxicity (CDC) as compared to a corresponding antibody comprising an Fc region that does not comprise the amino acid substitutions. In some embodiments, the modified Fc domain reduces complement-dependent cytotoxicity (CDC) as compared to a corresponding antibody comprising an Fc region that does not comprise the amino acid substitutions. In some embodiments, the modified Fc domain reduces effector function as compared to a corresponding antibody comprising an Fc region that does not comprise the amino acid substitutions. In some embodiments, the modified Fc domain increases half-life as compared to a corresponding antibody comprising an Fc region that does not comprise the amino acid substitutions. In some embodiments, the modified Fc domain decreases half-life as compared to a corresponding antibody comprising an Fc region that does not comprise the amino acid substitutions. In some embodiments, the modified Fc domain increases coengagement as compared to a corresponding antibody comprising an Fc region that does not comprise the amino acid substitutions. In some embodiments, the Fc region increases clustering without activating complement as compared to a corresponding antibody comprising an Fc region that does not comprise the amino acid substitutions. In some embodiments, the antibody induces one or more activities of a target specifically bound by the antibody. In some embodiments, the antibody binds to TNFR2.

It may also be desirable to modify the TNF-alpha variant fusion molecules of the present disclosure to modify effector function and/or to increase serum half-life of the antibody. Examples of effector functions include (i) C1q-binding, (ii) complement activation, (iii) complement-dependent cytotoxicity (CDC), (iv) oligomer formation, (v) oligomer stability, (vi) antibody-dependent cell-mediated cytotoxicity (ADCC), (vii) FcRn-binding, (viii) Fc-gamma receptor-binding, (ix) antibody-dependent cellular phagocytosis (ADCP), (x) complement-dependent cellular cytotoxicity (CDCC), (xi) complement-enhanced cytotoxicity, (xii) binding to complement receptor of an opsonized antibody mediated by the antibody, (xiii) internalization, (xiv) downmodulation, (xv) induction of apoptosis, (xvi) opsonisation, (xvii) proliferation modulation, such as proliferation reduction, inhibition, and stimulation, and (xvii) a combination of any of (i) to (xvi), of a dimeric protein, such as an antibody when e.g. bound to its antigen on a cell, on a cell membrane, on a virion, or on another particle. In some embodiments, for example, the Fc receptor binding site on the constant region may be modified or mutated to remove or reduce binding affinity to certain Fc receptors, such as FcγRI, FcγRII, and/or FcγRIII to reduce Fc-dependent cell-mediated cytotoxicity. In some embodiments, the effector function is impaired by removing N-glycosylation of the Fc region (e.g., in the CH2 domain of IgG) of the antibody. In some embodiments, the effector function is impaired by modifying regions such as 233-236, 297, and/or 327-331 of human IgG as described in WO 99/58572 and Armour et al. (2003) *Mol. Immunol.* 40:585-593; Reddy et al. (2000) *J. Immunol.* 164:1925-1933.

To increase the serum half-life of a TNF-alpha variant fusion molecule, one may incorporate a salvage receptor binding epitope into the molecule as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. Other amino acid sequence modifications.

In some embodiments, the modified Fc (e.g., IgG1 Fc) domain comprises one or more modifications. For example, in some embodiments, the Fc domain comprises one or more amino acid substitutions (e.g., relative to a wild-type Fc region of the same isotype). In some embodiments, the one or more amino acid substitutions are selected from N297A (Bolt S et al. (1993) *Eur J Immunol* 23:403-411), D265A (Shields et al. (2001) *J Biol. Chem.* 276, 6591-6604), L234A, L235A (Hutchins et al. (1995) *Proc Natl Acad Sci USA* 92:11980-11984; Alegre et al. (1994) *Transplantation* 57:1537-1543; Xu et al., (2000) *Cell Immunol.* 200:16-26), G237A (Alegre et al. (1994) *Transplantation* 57: 1537-1543; Xu et al. (2000) *Cell Immunol.* 200: 16-26), C226S, C229S, E233P, L234V, L234F, L235E (McEarchern et al., (2007) *Blood* 109: 1185-1192), P331S (Sazinsky et al., (2008) *Proc Natl Acad Sci USA* 105:20167-20172), S267E, L328F, A330L, M252Y, S254T, and/or T256E, where the amino acid position is according to the EU numbering convention.

In some embodiments, the modified Fc (e.g., IgG1 Fc) domain comprises N297A mutation according to EU numbering. In some embodiments, the modified Fc domain comprises D265A and N297A mutations according to EU numbering. In some embodiments, the modified Fc domain comprises D270A mutations according to EU numbering. In some embodiments, the modified Fc domain comprises L234A and L235A mutations according to EU numbering. In some embodiments, the modified Fc domain comprises a P331S mutation according to EU numbering. In some embodiments, the modified Fc domain comprises L234A and G237A mutations according to EU numbering. In some embodiments, the modified Fc domain comprises L234A, L235A and P331S mutations according to EU numbering. In some embodiments, the modified Fc domain comprises L234A, L235A, and G237A mutations according to EU numbering. In some embodiments, the modified Fc domain comprises one or more (including all) of P238D, L328E, E233, G237D, H268D, P271G, and A330R mutations according to EU numbering. In some embodiments, the modified Fc domain comprises one or more of S267E/F328F mutations according to EU numbering. In some embodiments, the modified Fc domain comprises P238D, F328E, E233D, G237D, H268D, P271G and A330R mutations according to EU numbering. In some embodiments, the modified Fc domain comprises P238D, F328E, G237D, H268D, P271G and A330R mutations according to EU numbering. In some embodiments, the modified Fc domain comprises P238D, S267E, F328E, E233D, G237D, H268D, P271G and A330R mutations according to EU numbering. In some embodiments, the modified Fc domain comprises P238D, S267E, F328E, G237D, H268D, P271G and A330R mutations according to EU numbering. In some embodiments, the modified Fc domain comprises C226S, C229S, E233P, F234V, and F235A mutations according to EU numbering. In some embodiments, the modified Fc domain comprises F234F, F235E, and P331S mutations according to EU numbering. In some embodiments, the modified Fc domain comprises S267E and F328F mutations according to EU numbering. In some embodiments, the modified Fc domain comprises S267E mutations according to EU numbering.

In some embodiments, the modified Fc (e.g., IgG1 Fc) domain comprises two or more amino acid substitutions that increase Fc clustering without activating complement as compared to a corresponding Fc region that does not include the two or more amino acid substitutions. In some embodiments, the modified Fc domain comprises an amino acid substitution at position E430G and one or more amino acid substitutions in the Fc region at a residue position selected from: F234F, F235A, F235E, S267E, K322A, F328F, A330S, P331S, and any combination thereof according to EU numbering. In some embodiments, the modified Fc domain comprises an amino acid substitution at positions E430G, F243A, F235A, and P331S according to EU numbering. In some embodiments, the modified Fc domain comprises an amino acid substitution at positions E430G and P331S according to EU numbering. In some embodiments, the modified Fc domain comprises an amino acid substitution at positions E430G and K322A according to EU numbering. In some embodiments, the modified Fc domain comprises an amino acid substitution at positions E430G, A330S, and P331S according to EU numbering. In some embodiments, the modified Fc domain comprises an amino acid substitution at positions E430G, K322A, A330S, and P331S according to EU numbering. In some embodiments, the modified Fc domain comprises an amino acid substitution at positions E430G, K322A, and A330S according to EU numbering. In some embodiments, the modified Fc domain comprises an amino acid substitution at positions E430G, K322A, and P331S according to EU numbering.

In some embodiments, the modified Fc (e.g., IgG1 Fc) domain further comprises herein are combined with an A330F mutation (Fazar et al. (2006) *Proc Natl Acad Sci USA* 103:4005-4010), or one or more of L234F, L235E, and/or P331S mutations (Sazinsky et al. (2008) *Proc Natl Acad Sci USA* 105:20167-20172), according to the EU numbering convention, to eliminate complement activation. In some embodiments of any of the modified Fc domain, the modified Fc further comprises one or more of A330L, A330S, L234F, L235E, and/or P331S according to EU numbering. In some embodiments, the modified Fc domain further comprises one or more mutations to enhance the half-life in human serum (e.g., one or more (including all) of M252Y, S254T, and T256E mutations according to the EU numbering convention). In some embodiments, the modified Fc domain further comprises one or more of E430G, E430S, E430F, E430T, E345K, E345Q, E345R, E345Y, S440Y, and/or S440W according to EU numbering.

In some embodiments, the modified Fc (e.g., IgG1 Fc) domain comprises two or more amino acid substitutions that enhance ADCC as compared to a corresponding Fc region that does not comprise the two or more amino acid substitutions. In some embodiments the modified Fc domain comprises an amino acid substitution at positions F243L/R292P/Y300L/V305I, according to the EU numbering convention, to increase FcγRIIIa binding. In some embodiments, the modified Fc domain comprises an amino acid substitution at positions S239D/I332E according to EU numbering to increase binding to FcγRIIIa and FcγRIIb. In some embodiments, the modified Fc domain comprises an amino acid substitution at positions S239D/I332E/A330L according to EU numbering to increase FcγRIIIa binding and decrease FcγRIIb binding. In some embodiments, the modified Fc domain comprises an amino acid substitution at positions G236A/S239D/I332E, according to the EU numbering convention, to increase FcγRIIIa and FcγRIIa binding, enhance FcγRIIb binding, and recover FcγRI binding lost by G236A mutation. In some embodiments, the modified Fc domain comprises an amino acid substitution at positions S298A/E333A/K334A, with L234Y/L235Q/G236W/S239M/H268D/D270E/S298A amino acid substitutions in one heavy chain and D270E/K326D/A330M/K334E amino acid substitutions in the opposing heavy chain, according to EU numbering, to increase FcγRIIIa binding. In some embodiments, the modified Fc domain comprises an amino acid substitution at positions S239D/A330L/I332E according to EU numbering to increase FcγRIIIa binding. In some embodiments, the modified Fc domain comprises an amino acid substitution at positions L234Y/G236W/S298A in one heavy chain constant region, according to EU numbering, to increase FcγRIIIa binding. In some embodiments, the modified Fc domain comprises an amino acid substitution at positions F243L/R292P/Y300L/V305I/P396L according to EU numbering to increase FcγRIIa and FcγRIIIa off-rates.

In some embodiments, the modified Fc (e.g., IgG1 Fc) domain comprises one or more amino acid substitutions that reduce ADCC as compared to a corresponding Fc region that does not include the one or more amino acid substitutions. In some embodiments, the modified Fc domain comprises an amino acid substitution at position L235E, according to the EU numbering convention, to decrease binding to cell surface FcγRIIIa binding. In some embodiments, the modified Fc domain comprises an amino acid substitution at positions L234A/L235A, according to EU numbering to decrease binding to FcγRI, FcγRII, and FcγRIII. In some embodiments, the modified Fc domain comprises an amino acid substitution at position D265A, according to EU numbering to decrease binding to FcγRI, FcγRII, and FcγRIII. In some embodiments, the modified Fc domain comprises an amino acid substitution at positions G236R/L328R, according to EU numbering to decrease binding to all FcγR. In some embodiments, the modified Fc domain comprises an amino acid substitution at positions L234A/L235A/G237A/P238S/H268A/A330S/P331S, according to EU numbering, to decrease binding to FcγRI, FcγRIIa, FcγRIIb, and FcγRIIIa. In some embodiments, the modified Fc domain comprises an amino acid substitution at position N297A or N297G or N297N according to EU numbering to decrease binding to C1q, and to decrease binding to FcγRI and FcγRIIIa.

In some embodiments, the modified Fc domain (e.g., IgG1 Fc) comprises one or more amino acid substitutions that enhance ADCP as compared to a corresponding Fc region that does not include the one or more amino acid substitutions. In some embodiments, the modified Fc domain comprises an amino acid substitution at positions G236A/S239D/I332E, according to the EU numbering convention, to increase FcγRIIIa and FcγRIIa binding, enhance FcγRIIb binding, and recover FcγRI binding lost by G236A mutation. In some embodiments, the modified Fc domain comprises an amino acid substitution at positions S239D/A330L/I332E according to EU numbering to decrease FcγRIIb binding. In some embodiments, the modified Fc domain comprises an amino acid substitution at positions S239D/I332E according to EU numbering to increase FcγRIIb binding. In some embodiments, the modified Fc domain comprises an amino acid substitution at positions G236A/S239D/A330L/I332E according to EU numbering to increase FcγRIIIa and FcγRIIa binding. In some embodiments, the modified Fc domain comprises an amino acid substitution at positions G236A according to EU numbering to increase FcγRIIa binding and decrease FcγR1 binding. In some embodiments, the modified Fc domain comprises an amino acid substitution at positions S239D/I332E according to EU numbering to increase binding to FcγRIIIa and FcγRIIb.

In some embodiments, the modified Fc (e.g., IgG1 Fc) domain comprises one or more amino acid substitutions that reduce ADCP as compared to a corresponding Fc region that does not include the one or more amino acid substitutions. In some embodiments, the modified Fc domain comprises an amino acid substitution at position L234A/L235A, according to EU numbering to decrease binding to FcγRI, FcγRII, and FcγRIII. In some embodiments, the modified Fc domain comprises an amino acid substitution at positions L234A/L235A/P329G according to EU numbering to eliminate binding to FcγRI, FcγRII, FcγRIII and C1q. In some embodiments, the modified Fc domain comprises an amino acid substitution at positions D265A, according to EU numbering to decrease binding to FcγRI, FcγRII, and FcγRIII. In some embodiments, the modified Fc domain comprises an amino acid substitution at position G237A, according to EU numbering to decrease binding to FcγRII. In some embodiments, the modified Fc domain comprises an amino acid substitution at position E318A, according to EU numbering to decrease binding to FcγRII. In some embodiments, the modified Fc domain comprises an amino acid substitution at position N297A or N297G or N297N according to EU numbering to decrease binding to C1q, and to decrease binding to FcγRI and FcγRIIIa.

In some embodiments, the modified Fc (e.g., IgG1 Fc) domain comprises one or more amino acid substitutions that enhance CDC as compared to a corresponding Fc region that does not include the one or more amino acid substitutions. In some embodiments, the modified Fc domain comprises an amino acid substitution at positions K326W/E333S, according to the EU numbering convention, to increase C1q binding. In some embodiments, the modified Fc domain comprises an amino acid substitution at positions K326W/E333A, according to the EU numbering convention, to increase C1q binding. In some embodiments, the modified Fc domain comprises an amino acid substitution at positions K326M/E333S, according to the EU numbering convention, to increase C1q binding. In some embodiments, the modified Fc domain comprises an amino acid substitution at positions C221D/D222C, according to the EU numbering convention, to increase C1q binding. In some embodiments, the modified Fc domain comprises an amino acid substitution at positions S267E/H268F/S324T according to EU numbering to increase C1q binding. In some embodiments, the modified Fc domain comprises an amino acid substitution at positions H268F/S324T according to EU numbering to increase C1q binding. In some embodiments, the modified Fc domain comprises an amino acid substitution at positions E345R/E430G/S440Y according to EU numbering to increase hexamerization. In some embodiments, the modified Fc domain comprises an amino acid substitution at position E345R according to EU numbering to increase hexamerization and to increase C1q binding.

In some embodiments, the modified Fc (e.g., IgG1 Fc) domain comprises one or more amino acid substitutions that reduce CDC as compared to a corresponding Fc region that does not include the one or more amino acid substitutions. In some embodiments, the modified Fc domain comprises an amino acid substitution at position L234A/L235A, according to EU numbering to decrease binding to FcγRI, FcγRII, and FcγRIII. In some embodiments, the modified Fc domain comprises an amino acid substitution at positions P331S/L234E/L235F according to EU numbering to decrease binding to FcγRI, FcγRII, FcγRIII, and C1q. In some embodiments, the modified Fc domain comprises an amino acid substitution at position D270A according to EU numbering to decrease binding to C1q. In some embodiments, the modified Fc domain comprises an amino acid substitution at position K322A according to EU numbering to decrease binding to C1q. In some embodiments, the modified Fc domain comprises an amino acid substitution at position P329A according to EU numbering to decrease binding to C1q. In some embodiments, the modified Fc domain comprises an amino acid substitution at position P331A according to EU numbering to decrease binding to C1q. In some embodiments, the modified Fc domain comprises an amino acid substitution at position V265A according to EU numbering to decrease binding to C1q. In some embodiments, the modified Fc domain comprises an amino acid substitution at position F241A according to EU numbering to decrease binding to C1q. In some embodiments, the modified Fc domain comprises an amino acid substitution at position N297A or N297G or N297N according to EU numbering to decrease binding to C1q, and to decrease binding to FcγRI and FcγRIIIa.

In some embodiments, the modified Fc (e.g., IgG1 Fc) domain comprises one or more amino acid substitutions that reduce effector function as compared to a corresponding Fc region that does not include the one or more amino acid substitutions. In some embodiments, the modified Fc domain comprises an amino acid substitution at position L235E, according to the EU numbering convention, to reduce FcγR and C1q binding. In some embodiments, the modified Fc domain comprises an N297A or N297Q or N297G amino acid substitution, according to the EU numbering convention, to reduce Fc glycosylation.

In some embodiments, the modified Fc (e.g., IgG1 Fc) domain comprises one or more amino acid substitutions that increase half-life as compared to a corresponding Fc region that does not include the one or more amino acid substitutions. In some embodiments, the modified Fc domain comprises an amino acid substitution at positions M252Y/S254T/T256E, according to the EU numbering convention, to increase FcRn binding at pH 6.0. In some embodiments, the modified Fc domain comprises an amino acid substitution at positions M428L/N434S according to EU numbering to increase FcRn binding at pH 6.0. In some embodiments, the modified Fc domain comprises an amino acid substitution at position R435H according to EU numbering to increase FcRn binding at low pH. In some embodiments, the modified Fc domain comprises an amino acid substitution at position N434A according to EU numbering to increase FcRn binding at pH 6.0. In some embodiments, the modified Fc domain comprises an amino acid substitution at positions T252L/T253S/T254F according to EU numbering to increase FcRn binding at or below pH 6.5. In some embodiments, the modified Fc domain comprises an amino acid substitution at positions E294 (residue deleted)/T307P/N434Y according to EU numbering to increase FcRn binding at or below pH 6.0 and decrease FcγRIIa binding. In some embodiments, the modified Fc domain comprises an amino acid substitution at positions T256N/A378V/S383N/N434Y according to EU numbering to increase FcRn binding at or below pH 6.0. In some embodiments, the modified Fc domain comprises an amino acid deletion at position E294 (residue deleted) according to EU numbering to increase sialylation.

In some embodiments, the modified Fc (e.g., IgG1 Fc) domain comprises two or more amino acid substitutions that increase coengagement as compared to a corresponding Fc region that does not include the two or more amino acid substitutions. In some embodiments, the modified Fc domain comprises an amino acid substitution at positions S267E/L328F, according to the EU numbering convention, to increase FcγRIIb binding. In some embodiments, the modified Fc domain comprises an amino acid substitution at positions N325S/L328F according to EU numbering to increase FcγRIIb binding and decrease FcγRIIIa binding.

In some embodiments, the modified Fc (e.g., IgG1 Fc) domain comprises one or more modification. In some embodiments, one or more modifications in the modified Fc is selected from the group consisting of: S298A, E333A, K334A, K326A, F243R, R292P, Y300L, V305I, P396L, F243L, R292P, Y300L, L235V, P396L, F243L, S239D, I332E, A330L, S267E, L328F, D265S, S239E, K326A, A327H, G237F, K326E, G236A, D270L, H268D, S324T, L234F, N325L, V266L, and S267D. In some embodiments, one or more modifications in the modified Fc is selected from the group consisting of S228P, M252Y, S254T, T256E, T256D, T250Q, H285D, T307A, T307Q, T307R, T307W, L309D, Q411H, Q311V, A378V, E380A, M428L, N434A, N434S, N297A, D265A, L234A, L235A, and N434W.

In some embodiments, the modified Fc domain (e.g., IgG1 Fc) comprises a specific combination of amino acid substitutions selected from the group consisting of: L234A/L235A; V234A/G237A; L235A/G237A/E318A; S228P/L236E; H268Q/V309L/A330S/P331S; C220S/C226S/C229S/P238S; C226S/C229S/E3233P/L235V/L235A; L234F/L235E/P331S; C226S/P230S; L234A/G237A; L234A/L235A/G237A; L234A/L235A/P329G.

In some embodiments, the modified Fc domain is an IgG2 modified Fc domain. In some embodiments, the modified Fc domain comprises one or more modifications. For example, in some embodiments, the modified Fc comprises one or more amino acid substitutions (e.g., relative to a wild-type Fc region of the same isotype). In some embodiments, the one or more amino acid substitutions are selected from V234A (Alegre et al. (1994) *Transplantation* 57:1537-1543; Xu et al. *Cell Immunol.* (2000) 200:16-26); G237A (Cole et al. (1999) *Transplantation* 68:563-571); H268Q, V309L, A330S, P331S (U.S. Pat. No. 7,700,099; Armour et al. (1999) *Eur J Immunol* 29:2613-2624; Armour et al. (2000) *Haematology Journal* 1 (Suppl. 1):27; Armour et al. (2000) *Haematology Journal* 1 (Suppl. 1):27), C219S, and/or C220S (White et al. (2015) *Cancer Cell* 27, 138-148); S267E, L328F (Chu et al. (2008) *Mol Immunol.* 45:3926-3933); and M252Y, S254T, and/or T256E according to the EU numbering convention. In some embodiments, the modified Fc domain comprises an amino acid substitution at positions V234A and G237A according to EU numbering. In some embodiments, the modified Fc domain comprises an amino acid substitution at positions C219S or C220S according to EU numbering. In some embodiments, the modified Fc domain comprises an amino acid substitution at positions A330S and P331S according to EU numbering. In some embodiments, the modified Fc domain comprises an amino acid substitution at positions S267E and L328F according to EU numbering.

In some embodiments, the modified Fc (e.g., IgG2 Fc) domain comprises a C127S amino acid substitution according to the EU numbering convention (White et al., (2015) *Cancer Cell* 27, 138-148; Lightle et al. *Protein Sci.* (2010) 19:753-762; and WO 2008/079246). In some embodiments, the modified Fc domain comprises a C220S amino acid substitution according to the EU numbering convention. In some embodiments, the modified Fc domain comprises a C219S amino acid substitution according to the EU numbering convention. In some embodiments of any of the IgG2 modified Fc, the Fc domain comprises a S267E amino acid substitution, a L328F amino acid substitution, or both, and/or a N297A or N297Q amino acid substitution according to the EU numbering convention. In some embodiments, the modified Fc domain further comprises one or more amino acid substitution at positions E430G, E430S, E430F, E430T, E345K, E345Q, E345R, E345Y, S440Y, and S440W according to EU numbering. In some embodiments, the modified Fc domain further comprises one or more mutations to enhance the molecule half-life in human serum (e.g., one or more (including all) of M252Y, S254T, and T256E mutations according to the EU numbering convention). In some embodiments, the modified Fc domain further comprises A330S and P331S.

In some embodiments, the modified Fc domain is an IgG2/4 hybrid Fc. In some embodiments, the IgG2/4 hybrid Fc comprises IgG2 aa 118 to 260 and IgG4 aa 261 to 447. In some embodiments, the modified Fc domain comprises one or more amino acid substitutions at positions H268Q, V309L, A330S, and P331S according to EU numbering.

In some embodiments, the modified Fc domain comprises one or more additional amino acid substitutions selected from A330L, L234F; L235E, P329G, or P331S according to EU numbering; and any combination thereof. In some embodiments, the modified Fc domain comprises one or more amino acid substitutions at a residue position selected from C127S, L234A, L234F, L235A, L235E, S267E, K322A, L328F, A330S, P331S, E345R, E430G, S440Y, and any combination thereof according to EU numbering. In some embodiments, the modified Fc domain comprises an amino acid substitution at positions E430G, L243A, L235A, and P331S according to EU numbering. In some embodiments of any of the IgG1 and/or IgG2 modified Fc domain, the Fc domain comprises an amino acid substitution at positions E430G and P331S according to EU numbering. In some embodiments of any of the IgG1 and/or IgG2 modified Fc domain, the Fc comprises an amino acid substitution at positions E430G and K322A according to EU numbering. In some embodiments, the modified Fc domain comprises an amino acid substitution at positions E430G, A330S, and P331S according to EU numbering. In some embodiments, the modified Fc domain comprises an amino acid substitution at positions E430G, K322A, A330S, and P331S according to EU numbering. In some embodiments, the modified Fc domain comprises an amino acid substitution at positions E430G, K322A, and A330S according to EU numbering. In some embodiments, the modified Fc domain comprises an amino acid substitution at positions E430G, K322A, and P331S according to EU numbering. In some embodiments, the modified Fc domain comprises an amino acid substitution at positions S267E and F328F according to EU numbering. In some embodiments of any of the IgG1 and/or IgG2 modified Fc, the Fc comprises an amino acid substitution at position C127S according to EU numbering. In some embodiments, the modified Fc domain comprises an amino acid substitution at positions E345R, E430G and S440Y according to EU numbering.

In some embodiments of any of the TNF-alpha variant fusion molecules provided herein, the modified Fc domain is an IgG4 modified Fc domain. In some embodiments, the modified Fc domain comprises one or more modifications. For example, in some embodiments, the modified Fc domain comprises one or more amino acid substitutions (e.g., relative to a wild-type Fc region of the same isotype). In some embodiments, the one or more amino acid substitutions are selected from F235A, G237A, S229P, F236E (Reddy et al. (2000) *J Immunol.* 164: 1925-1933), S267E, E318A, F328F, M252Y, S254T, and/or T256E according to the EU numbering convention. In some embodiments, the modified Fc domain further comprises F235A, G237A, and E318A according to the EU numbering convention. In some embodiments, the modified Fc domain further comprises S228P and F235E according to the EU numbering convention. In some embodiments, the modified Fc domain further comprises S267E and F328F according to the EU numbering convention. In some embodiments, the modified Fc domain is combined with an S228P mutation according to the EU numbering convention (Angal et al. (1993) *Mol Immunol.* 30: 105-108) and/or with one or more mutations described in (Peters et al. (2012) *J Biol Chem.* 287(29):24525-33) to enhance molecule stabilization. In some embodiments, the modified Fc domain further comprises one or more mutations to enhance the molecule half-life in human serum (e.g., one or more (including all) of M252Y, S254T, and T256E mutations according to the EU numbering convention).

In some embodiments, the modified Fc (e.g., IgG1, IgG2, IgG4 Fc) domain comprises a specific combination of amino acid substitutions selected from the group consisting of M428L/N434S (LS); M252Y/S254T/T256E (YTE); T250Q/M428L; T307A/E380A/N434A; T256D/T307Q (DQ); T256D/T307W (DW); M252Y/T256D (YD); T307Q/Q311V/A378V (QVV); T256D/H285D/T307R/Q311V/A378V (DDRVV); L309D/Q311H/N434S (DHS); S228P/L235E (SPLE); L234A/L235A (LALA); M428L/N434A (LA); L234A/G237A (LAGA); L234A/L235A/G237A (LALAGA); L234A/L235A/P329G (LALAPG); N297A/YTE; D265A/YTE; LALA/YTE; LAGA/YTE; LALAGA/YTE; LALAPG/YTE; N297A/LS; D265A/LS; LALA/LS; LAGA/LS; LALAGA/LS; LALAPG/LS; N297A/DHS; D265A/DHS; LALA/DHS; LAGA/DHS; LALAGA/DHS; LALAPG/DHS; SP/YTE; SPLE/YTE; SP/LS; SPLE/LS; SP/DHS; SPLE/DHS; N297A/LA; D265A/LA; LALA/LA; LAGA/LA; LALAGA/LA; LALAPG/LA; N297A/N434A; D265A/N434A; LALA/N434A; LAGA/N434A; LALAGA/N434A; LALAPG/N434A; N297A/N434W; D265A/N434W; LALA/N434W; LAGA/N434W; LALAGA/N434W; LALAPG/N434W; N297A/DQ; D265A/DQ; LALA/DQ; LAGA/DQ; LALAGA/DQ; LALAPG/DQ; N297A/DW; D265A/DW; LALA/DW; LAGA/DW; LALAGA/DW; LALAPG/DW; N297A/YD; D265A/YD; LALA/YD; LAGA/YD; LALAGA/YD; LALAPG/YD; N297A/QVV; D265A/QVV; LALA/QVV; LAGA/QVV, LALAGA/QVV; LALAPG/QVV; N297A/DDRVV; D265A/DDRVV; LALA/DDRVV; LAGA/DDRVV; LALAGA/DDRVV; and LALAPG/DDRVV.

In some embodiments of any of the TNF-alpha variant fusion molecules provided herein, the TNF-alpha variant fusion molecule particularly the Fc domain is altered to increase or decrease the extent to which the antibody is glycosylated. Addition or deletion of glycosylation sites to an antibody may be conveniently accomplished by altering the amino acid sequence such that one or more glycosylation sites is created or removed.

Glycosylation of Fc domains is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxy lysine may also be used.

Addition of glycosylation sites to the Fc domain is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the TNF-alpha variant fusion molecule comprises an Fc region, the carbohydrate attached thereto may be altered. Native antibodies produced by mammalian cells typically comprise a branched, biantennary oligosaccharide that is generally attached by an N-linkage to Asn297 according to Kabat numbering of the CH2 domain of the Fc region. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the disclosure may be made in order to create Fc variants domains with certain improved properties. In one embodiment, Fc variant domains are provided having a carbohydrate structure that lacks fucose attached (directly or indirectly) to an Fc region. See, e.g., US Patent Publication Nos. 2003/0157108 and 2004/0093621. Examples of publications related to "defucosylated" or "fucose-deficient" Fc variant domains include: US 2003/0157108; U.S. Pat. Nos. 6,946,292; 7,064,191; US 2004/0093621; US 2004/0132140; US 2004/0110704; U.S. Pat. Nos. 7,749,753; 7,691,568; Okazaki et al. (2004) *J. Mol. Biol.* 336:1239-1249; Yamane-Ohnuki et al. (2004) *Biotech. Bioeng.* 87:614. Examples of cell lines capable of producing defucosylated antibodies include Led 3 CHO cells deficient in protein fucosylation (Ripka et al. (1986) *Arch. Biochem. Biophys.* 249:533-545; US 2003/0157108), and knockout cell lines, such as alpha-1, 6-fucosyltransferase gene, FUT8, knockout CHO cells (see, e.g., Yamane-Ohnuki et al. (2004) *Biotech. Bioeng.* 87:614 and Kanda et al. (2006) *Biotech. Bioeng.* 94(4):680-688).

IV. Nucleic Acids, Vectors, and Host Cells

The TNF-alpha variants and/or TNF-alpha variant fusion molecules of the present disclosure may be produced using recombinant methods and compositions, e.g., as described in U.S. Pat. No. 4,816,567. In some embodiments, isolated nucleic acids having a nucleotide sequence encoding any of the TNF-alpha variants and/or TNF-alpha variant fusion molecules of the present disclosure are provided. In some embodiments, one or more vectors (e.g., expression vectors) comprising such nucleic acids are provided. In some embodiments, a host cell comprising such nucleic acid is also provided. In some embodiments, the host cell comprises (e.g., has been transduced with): a vector comprising a nucleic acid that encodes an amino acid sequence comprising the TNF-alpha variants and/or TNF-alpha variant fusion molecules. In some embodiments, the host cell is eukaryotic, e.g., a Chinese Hamster Ovary (CHO) cell or lymphoid cell (e.g., Y0, NSO, Sp20 cell). Host cells of the present disclosure also include, without limitation, isolated cells, in vitro cultured cells, and ex vivo cultured cells.

Methods of making TNF-alpha variants and/or TNF-alpha variant fusion molecules of the present disclosure are provided. In some embodiments, the method includes culturing a host cell of the present disclosure comprising a nucleic acid encoding the TNF-alpha variants and/or TNF-alpha variant fusion molecules, under conditions suitable for expression of the variant and/or molecule. In some embodiments, the TNF-alpha variant and/or TNF-alpha variant fusion molecule is subsequently recovered from the host cell (or host cell culture medium).

For recombinant production of TNF-alpha variants and/or TNF-alpha variant fusion molecules of the present disclosure, a nucleic acid encoding the TNF-alpha variants and/or TNF-alpha variant fusion molecules is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the TNF-alpha variant and/or TNF-alpha variant fusion molecule).

Suitable vectors comprising a nucleic acid sequence encoding any of the TNF-alpha variants and/or TNF-alpha variant fusion molecules of the present disclosure, or cell-surface expressed fragments or polypeptides thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones comprising the vector. Suitable examples include plasmids and bacterial viruses, e.g., pUC18, pUC19, Bluescript (e.g., pBS SK+) and its derivatives, mpl8, mpl9, pBR322, pMB9, ColEl, pCRl, RP4, phage DNAs, and shuttle vectors such as pSA3 and pAT28.

Suitable host cells for cloning or expression of protein-encoding vectors include prokaryotic or eukaryotic cells. For example, TNF-alpha variants and/or TNF-alpha variant fusion molecules of the present disclosure may be produced in bacteria, in particular when glycosylation and Fc effector function are not needed. For expression of TNF-alpha variants and/or TNF-alpha variant fusion molecules fragments and polypeptides in bacteria (e.g., U.S. Pat. Nos. 5,648,237, 5,789,199, and 5,840,523. After expression, the TNF-alpha variant and/or TNF-alpha variant fusion molecule may be isolated from the bacterial cell paste in a soluble fraction and can be further purified.

In addition to prokaryotes, eukaryotic microorganisms, such as filamentous fungi or yeast, are also suitable cloning or expression hosts for TNF-alpha variants and/or TNF-alpha variant fusion molecules-encoding vectors, including fungi and yeast strains whose glycosylation pathways have been "humanized," resulting in the production of an TNF-alpha variants and/or TNF-alpha variant fusion molecules with a partially or fully human glycosylation pattern (e.g., Gerngross (2004) *Nat. Biotech.* 22: 1409-1414; and Li et al. (2006) Nat. Biotech. 24:210-215).

Suitable host cells for the expression of TNF-alpha variant and/or glycosylated TNF-alpha variant fusion molecule can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125, 978, and 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or HEK293 cells as described, e.g., in Graham et al. (1977) *J. Gen Virol.* 36:59); baby hamster kidney cells (BHK); mouse sertoli cells (TM4 cells as described, e.g., in Mather (1980) *Biol. Reprod.* 23:243-251); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al. (1982) *Annals N. Y. Acad. Sci.* 383:44-68; MRC 5 cells; and FS4 cells. Other useful mammalian host cell lines include Chinese hamster ovary (CHO) cells, including DHFR-CHO cells (Urlaub et al. (1980) *Proc. Natl. Acad. Sci. USA* 77:4216); and myeloma cell lines such as Y0, NS0 and Sp2/0. For a review of certain mammalian host cell lines suitable for TNF-alpha variant and/or TNF-alpha variant fusion molecule production, see, e.g., Yazaki and Wu, Methods in Molecular Biology, Vol. 248 (B. K. C. Lo, ed., Humana Press, Totowa, NJ), pp. 255-268 (2003).

V. Pharmaceutical Compositions/Formulations

Provided herein are pharmaceutical compositions and/or pharmaceutical formulations comprising the TNF-alpha variants and/or TNF-alpha variant fusion molecules of the present disclosure and a pharmaceutically acceptable carrier.

In some embodiments, the pharmaceutically acceptable carriers preferably are nontoxic to recipients at the dosages and concentrations employed. The antibodies described herein may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutically acceptable carriers can include, depending on the formulation desired, non-toxic carriers of diluents, which are vehicles commonly used to formulate pharmaceutical compositions for animal or human administration. In certain embodiments, the pharmaceutical composition can comprise formulation materials for modifying, maintaining or preserving, for example, the pH, osmolarity, viscosity, clarity, color, isotonicity, odor, sterility, stability, rate of dissolution or release, adsorption or penetration of the composition.

In certain embodiments, pharmaceutically acceptable carriers include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants.

Further examples of formulations that are suitable for various types of administration can be found in Remington: The Science and Practice of Pharmacy, Pharmaceutical Press 22nd ed. (2013). For a brief review of methods for drug delivery, see, Langer (1990) Science 249:1527-1533. Formulations suitable for parenteral administration include aqueous and non-aqueous, isotonic sterile injection solutions, which can comprise antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the TNF-alpha variants and/or TNF-alpha variant fusion molecules of the present disclosure, in a biodegradable or bioerodible implant. The rate of release of the therapeutically active agent is controlled by the rate of transport through the polymeric matrix, and the biodegradation of the implant. Implants may be particles, sheets, patches, plaques, fibers, microcapsules and the like and may be of any size or shape compatible with the selected site of insertion. Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxy aliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the present disclosure. Hydrogels are typically a copolymer material, characterized by the ability to imbibe a liquid.

VI. Therapeutic Uses

As disclosed herein, the TNF-alpha variants and/or TNF-alpha variant fusion molecules of the present disclosure may be used for preventing, reducing risk, or treating a disease and disorder. In some embodiments, the disease or disorder is an inflammatory disease or disorder. In some embodiments, the inflammatory disease or disorder is an inflammatory bowel disease or disorder (e.g., ulcerative colitis, Crohn's disease). In some embodiments, the disease or disorder is an autoimmune disease or disorder. In some embodiments, the disease or disorder is characterized by dysregulation of Treg cells. In some embodiments, the disease or disorder is characterized by autoreactive T cells or by HLA-associated susceptibility.

In some embodiments of any of the methods herein, the disease or disorder is charactered by and/or the patient is selected for use in the methods by reduced levels of and/or low activity populations of CD3+CD4+FoxP3+ Tregs (for example compared to average levels and/or activity of population without the disease or disorder). In some embodiments of any of the CD3+CD4+FoxP3+ Tregs, the Tregs further express one or more of CD25, CD39, ICAM1, HLA-DR, CCR4, CCR7, CLA, integrin beta 7, and/or integrin alpha E. In some embodiments of any of the methods herein, the disease or disorder and/or the patient is selected for use in the methods by is charactered by reduced level of and/or low activity populations of CD3+CD4+FoxP3+CD25+ Tregs. In some embodiments of any of the methods herein, the disease or disorder is charactered by and/or the patient is selected for use in the methods by reduced level of and/or low activity populations of CD3+CD4+FoxP3+CD39+ Tregs. In some embodiments of any of the methods herein, the disease or disorder and/or the patient is selected for use in the methods by is charactered by reduced level of and/or low activity populations of CD3+CD4+FoxP3+CCR4+ Tregs. In some embodiments of any of the methods herein, the disease or disorder is charactered by and/or the patient is selected for use in the methods by reduced level of and/or low activity populations of CD3+CD4+FoxP3+CCR7+ Tregs. In some of the embodiments, levels of marker-identified Tregs may be determined by flow cytometry.

Further, the TNF-alpha variants and/or TNF-alpha variant fusion molecules of the present disclosure may be used for preventing, reducing risk, or treating a disease and disorder, wherein response to such TNF-alpha variants and/or TNF-alpha variant fusion molecules is determined by change in levels of and/or activity of CD3+CD4+FoxP3+ Tregs (for example compared to prior to use of the TNF-alpha variants and/or TNF-alpha variant fusion molecules of the present disclosure). In some embodiments, increased of levels of and/or increased activity of CD3+CD4+FoxP3+ Tregs (for example compared to prior to use of the TNF-alpha variants and/or TNF-alpha variant fusion molecules of the present disclosure) indicates response to the use of the TNF-alpha variants and/or TNF-alpha variant fusion molecules. In some embodiments of any of the CD3+CD4+FoxP3+ Tregs, the Tregs further express one or more of CD25, CD39, ICAM1, HLA-DR, CCR4, CCR7, CLA, integrin beta 7, and/or integrin alpha E. In some embodiments of any of the methods herein, response to such TNF-alpha variants and/or TNF-alpha variant fusion molecules is determined by change in levels (e.g., increase) of and/or activity (e.g., increase) of CD3+CD4+FoxP3+CD25+ Tregs. In some embodiments of any of the methods herein, the response to such TNF-alpha variants and/or TNF-alpha variant fusion molecules is determined by change in levels (e.g., increase) of and/or activity (e.g., increase) of CD3+CD4+FoxP3+CD39+ Tregs. In some embodiments of any of the methods herein, the response to such TNF-alpha variants and/or TNF-alpha variant fusion molecules is determined by change in levels (e.g., increase) of and/or activity (e.g., increase) of CD3+CD4+FoxP3+CCR4+ Tregs. In some embodiments of any of the methods herein, the response to such TNF-alpha variants and/or TNF-alpha variant fusion molecules is determined by change in levels (e.g., increase) of and/or activity (e.g., increase) of CD3+CD4+FoxP3+CCR7+ Tregs. In some of the embodiments, levels of marker-identified Tregs may be determined by flow cytometry.

In some embodiments, the TNF-alpha variants and/or TNF-alpha variant fusion molecules of the present disclosure are used for preventing, reducing risk, or treating a disease and disorder, wherein response to such TNF-alpha variants and/or TNF-alpha variant fusion molecules is determined by change in the TNFR2-induced gene expression signature or genes within the TNFR2-induced gene expression signature (for example compared to prior to use of the TNF-alpha variants and/or TNF-alpha variant fusion molecules of the present disclosure). In some embodiments, an increase or elevation of TNFR2-induced gene expression signature or genes within the TNFR2-induced gene expression signature (for example compared to prior to use of the TNF-alpha variants and/or TNF-alpha variant fusion molecules of the present disclosure) indicates response to the use of the TNF-alpha variants and/or TNF-alpha variant fusion molecules. In some embodiments, the TNFR2-induced gene expression signature or genes within the TNFR2-induced gene expression signature is determined in whole blood.

In some embodiments of any of the methods herein, the disease or disorder is charactered by and/or the patient is selected for use in the methods by elevated levels of CCL17 (TARC), CCL22, IgE, MMP12, S100A7/12 (for example compared to average levels of population without the disease or disorder). In some embodiments of any of the methods herein, the disease or disorder and/or the patient is selected for use in the methods by is charactered by elevated level of CCL17 (TARC). In some embodiments of any of the methods herein, the disease or disorder is charactered by and/or the patient is selected for use in the methods by elevated level of CCL22. In some embodiments of any of the methods herein, the disease or disorder and/or the patient is selected for use in the methods by is charactered by elevated level of IgE. In some embodiments of any of the methods herein, the disease or disorder is charactered by and/or the patient is selected for use in the methods by elevated level of MMP12. In some embodiments of any of the methods herein, the disease or disorder is charactered by and/or the patient is selected for use in the methods by elevated level of S100A7/12. In some of the embodiments, levels of marker-identified Tregs may be determined by flow cytometry.

In some embodiments, the TNF-alpha variants and/or TNF-alpha variant fusion molecules of the present disclosure are used for preventing, reducing risk, or treating a disease and disorder, wherein response to such TNF-alpha variants and/or TNF-alpha variant fusion molecules is determined by change in levels of CCL17 (TARC), CCL22, IgE, MMP12, S100A7/12 (for example compared to prior to use of the TNF-alpha variants and/or TNF-alpha variant fusion molecules of the present disclosure). In some embodiments, reduction of levels of CCL17 (TARC), CCL22, IgE, MMP12, S100A7/12 (for example compared to prior to use of the TNF-alpha variants and/or TNF-alpha variant fusion molecules of the present disclosure) indicates response to the use of the TNF-alpha variants and/or TNF-alpha variant fusion molecules. In some embodiments of any of the methods herein, response to such TNF-alpha variants and/or TNF-alpha variant fusion molecules is determined by change in levels (e.g., reduction) of CCL17 (TARC). In some embodiments of any of the methods herein, the response to such TNF-alpha variants and/or TNF-alpha variant fusion molecules is determined by change in levels (e.g., reduction) of CCL22. In some embodiments of any of the methods herein, the response to such TNF-alpha variants and/or TNF-alpha variant fusion molecules is determined by change in levels (e.g., reduction) of IgE. In some embodiments of any of the methods herein, the response to such TNF-alpha variants and/or TNF-alpha variant fusion molecules is determined by change in levels (e.g., reduction) of MMP12. In some embodiments of any of the methods herein, the response to such TNF-alpha variants and/or TNF-alpha variant fusion molecules is determined by change in levels (e.g., reduction) of S100A7/12.

In some embodiments, a TNF-alpha variant and/or TNF-alpha variant fusion molecule of the present disclosure is effective at preventing, reducing risk, or treating inflammatory bowel disease (IBD), ulcerative colitis, Crohn's disease, primary sclerosing cholangitis, celiac disease, atopic dermatitis, alopecia areata, vitiligo, dermatomyositis, hidradenitis suppurativa, systemic lupus erythematosus, rheumatoid arthritis, ankylosing spondylitis, multiple sclerosis, myasthenia gravis, Behcet's disease, or type I diabetes.

In some embodiments of any of the methods, a subject or individual is a mammal. Mammals include, without limitation, domesticated animals (e.g., cows, sheep, cats, dogs, and horses), primates (e.g., humans and non-human primates such as monkeys), rabbits, and rodents (e.g., mice and rats). In some embodiments, the subject or individual is a human.

The TNF-alpha variants and/or TNF-alpha variant fusion molecules provided herein (and any additional therapeutic agent) can be administered by any suitable means, including parenteral, intrapulmonary, intranasal, intralesional administration, intracerobrospinal, intracranial, intraspinal, intrasynovial, intrathecal, oral, topical, or inhalation routes. Parenteral infusions include intramuscular, intravenous administration as a bolus or by continuous infusion over a period of time, intraarterial, intra-articular, intraperitoneal, intradermal, or subcutaneous administration. In some embodiments, the administration is intravenous administration. In some embodiments, the administration is subcutaneous. Dosing can be by any suitable route, e.g., by injections, such as intravenous or subcutaneous injections, depending in part on whether the administration is brief or chronic. Various dosing schedules including but not limited to single or multiple administrations over various timepoints, bolus administration, and pulse infusion are contemplated herein.

The TNF-alpha variants and/or TNF-alpha variant fusion molecules provided herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The TNF-alpha variant and/or TNF-alpha variant fusion molecule may optionally be formulated with one or more agents currently used to prevent or treat the disorder in question. The effective amount of such other agents depends on the amount of TNF-alpha variant and/or TNF-alpha variant fusion molecule present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a TNF-alpha variant and/or TNF-alpha variant fusion molecule of the disclosure (when used alone or in combination with one or more other additional therapeutic agents) will depend on the type of disease to be treated, the type of TNF-alpha variant and/or TNF-alpha variant fusion molecule, the severity and course of the disease, whether the TNF-alpha variant and/or TNF-alpha variant fusion molecule is administered for preventive or therapeutic purposes, previous therapy, the patient's clinical history and response to the TNF-alpha variants and/or TNF-alpha variant fusion molecules, and the discretion of the attending physician. The TNF-alpha variant and/or TNF-alpha variant fusion molecule is suitably administered to the patient at one time or over a series of treatments.

VII. Articles of Manufacture

Provided herein are articles of manufacture (e.g., kit) comprising a TNF-alpha variant and/or TNF-alpha variant fusion molecule described herein. Article of manufacture may include one or more containers comprising a TNF-alpha variant and/or TNF-alpha variant fusion molecule described herein. Containers may be any suitable packaging including, but is not limited to, vials, bottles, jars, flexible packaging (e.g., sealed Mylar or plastic bags), and the like. The containers may be unit doses, bulk packages (e.g., multi-dose packages) or sub-unit doses.

In some embodiments, the kits may further include a second agent. In some embodiments, the second agent is a pharmaceutically-acceptable buffer or diluting agent including, but not limited to, such as bacteriostatic water for injection (BWFI), phosphate-buffered saline, Ringer's solution and dextrose solution. In some embodiments, the second agent is a pharmaceutically active agent.

In some embodiments of any of the articles of manufacture, the article of manufactures further include instructions for use in accordance with the methods of this disclosure. The instructions generally include information as to dosage, dosing schedule, and route of administration for the intended treatment.

In some embodiments, these instructions comprise a description of administration of the TNF-alpha variant and/or TNF-alpha variant fusion molecule of the present disclosure to prevent, reduce risk, or treat an individual having an inflammatory disease or disorder or an autoimmune disease or disorder. In some embodiments, these instructions comprise a description of administration of the TNF-alpha variant and/or TNF-alpha variant fusion molecule of the present disclosure to prevent, reduce risk, or treat an individual having ulcerative colitis, Crohn's disease, primary sclerosing cholangitis, celiac disease, atopic Dermatitis, alopecia areata, vitiligo, dermatomyositis, hidradenitis suppurativa, systemic lupus erythematosus, rheumatoid arthritis, ankylosing spondylitis, multiple sclerosis, myasthenia gravis, Behcet's disease, or type I diabetes.

In some embodiments, the instructions include instructions for use of the TNF-alpha variant and/or TNF-alpha variant fusion molecule and the second agent (e.g., second pharmaceutically active agent).

The present disclosure will be more fully understood by reference to the following Examples. They should not, however, be construed as limiting the scope of the present disclosure. All citations throughout the disclosure are hereby expressly incorporated by reference.

EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Engineering TNF-Alpha Variant Fusion Molecules

As stated in Challener et al., *BioPharm International*—May 1, 2017 30(5):30-31, the unique structures of fusion proteins can lead to expression, heterogeneity, and stability issues. Combining two different proteins—such as a cell surface receptor or cytokine and an immunoglobulin domain (e.g., IgG Fc)—in one molecule can lead to instability and aggregation, which creates manufacturing challenges during both upstream and downstream processing. The patent application WO201822675 describes various fusion proteins comprising a single chain TNFR2 selective agonist and an IgG Fc. In an effort to improve manufacture, purification, and storage properties of candidate TNFR2 selective fusion proteins, particularly instability and aggregation, various TNF-alpha variant fusion molecules having a TNF-alpha variant molecule attached to an Fc were constructed and assayed for stability and ability to retain specificity for TNFR2 compared to TNFR1. The TNF-alpha variant fusion molecules in these Examples included TNF-alpha variant molecules comprising three TNF-alpha variants covalently attached by a linker molecule. The Fc used in the Examples was an IgG1 isotype Fc that included mutations L234A, L235A, and P331S to block binding to Fc gamma receptors as well as complement binding. The Fc was fused to either the C-terminus or N-terminus of each TNF-alpha variant molecule. Table 1 provides the specific TNF-alpha mutations used in each TNF-alpha variant molecule, location of the Fc in relation to each TNF-alpha variant molecule, SEQ ID NO of each TNF-alpha variant, SEQ ID NO of each TNF-alpha variant molecule, and SEQ ID NO of each full-length TNF-alpha variant fusion molecule.

production run, with a temperature shift performed on day 1 post transfection. The conditioned media from the transient production run was harvested and clarified by centrifugation and filtration. The supernatant was loaded over a Protein A column pre-equilibrated with binding buffer. Washing buffer was passed through the column following standard procedures. Each TNF-alpha variant fusion molecule was eluted with a low pH buffer and neutralized immediately, fractions were collected, and the $OD_{280}$ value of each fraction was recorded. Fractions containing each TNF-alpha variant fusion molecule were pooled and filtered through a 0.2 m membrane filter. The protein concentration was calculated from the $OD_{280}$ value and the calculated extinction coefficient.

Analysis of each sample eluted from the Protein A column was performed by HPLC SEC to determine the percentage of monomer present in each sample (i.e., AUC). Calculated percentage of monomer in the Protein A eluted samples is shown in Table 2 and FIG. 1.

TABLE 1

TNF-alpha variant fusion molecules

| Name | TNF-alpha variant mutations | Fc location | Fc SEQ ID NO: | Linker SEQ ID NO: | TNF-alpha variant SEQ ID NOS: | variant TNF-alpha molecule SEQ ID NO: | TNF-alpha variant fusion molecule SEQ ID NO: |
|---|---|---|---|---|---|---|---|
| Wild-type | Wild-type | C-term Fc | 17 | 16 | 1, 2 | 11 | 18 |
| Variant 1 | D143N | C-term Fc | 17 | 16 | 3, 4 | 12 | 19 |
| Variant 2 | A145R | C-term Fc | 17 | 16 | 5, 6 | 13 | 20 |
| Variant 3 | D143N, A145R | C-term Fc | 17 | 16 | 7, 8 | 14 | 21 |
| Variant 4 | D143N, A145R | N-term Fc | 17 | 16 | 7, 8 | 14 | 22 |
| Variant 5 | D143Y, A145G | C-term Fc | 17 | 16 | 9, 10 | 15 | 23 |
| Variant 6 | D143Y, A145G | N-term Fc | 17 | 16 | 9, 10 | 15 | 24 |

Example 2: Low pH Elution-Mediated Aggregation of TNF-Alpha Variant Fusion Molecules This Example describes expression of the TNF-alpha variant fusion molecules described in Example 1 in a production cell line, and assesses sample aggregation of Variant 3, Variant 4, Variant 5, and Variant 6 after elution from protein A columns under low pH conditions.

Each recombinant TNF-alpha variant fusion molecule gene sequence was cloned into a high expression mammalian vector. Prior to transfection, each TNF-alpha variant fusion molecule gene sequence was confirmed for quality by agarose gel. Suspension CHO or HEK cells were seeded in a shake flask and were expanded using serum-free chemically defined medium. On the day of transfection, the expanded cells were seeded into a new flask with fresh medium. Each DNA construct was transiently transfected into CHO or HEK cells using standard methods. The cells were maintained as a batch-fed culture until the end of the

TABLE 2

Percentage of monomer for each TNF-alpha variant fusion molecule sample eluted from Protein A column

| Name | % Monomer post ProA elution |
|---|---|
| Variant 3 | 52[a] |
| Variant 3 | 47[b] |
| Variant 3 | 33[a] |
| Variant 4 | 61[b] |
| Variant 4 | 79[b] |
| Variant 4 | 65[a] |
| Variant 4 | 85[a] |
| Variant 5 | 74[a] |
| Variant 5 | 85[a] |
| Variant 6 | 93[a] |

[a]Result from CHO cell suspension culture
[b]Result from HEK cell suspension culture Variant 5 and Variant 6 exhibited a higher percentage of monomer after elution from protein A column relative to Variant 3 and Variant 4. These data indicate that TNF-alpha variant fusion molecules comprising the D143Y/A145G double mutation (i.e., Variant 5 and Variant 6) had a higher percentage of monomer after elution from protein A column relative to D143N/A145R double mutant variants (i.e., Variant 3 and Variant 4). Furthermore, Variant 6 and Variant 4 exhibited a higher percentage of monomer after elution than did Variant 5 and Variant 3, respectively.

Example 3: Melting Temperature of TNF-Alpha Variant Fusion Molecules

This Example assesses a measure of stability of TNF-alpha variant fusion molecules Variant 3, Variant 4, Variant 5, and Variant 6 via analysis of protein melting temperature.

Figure 2:
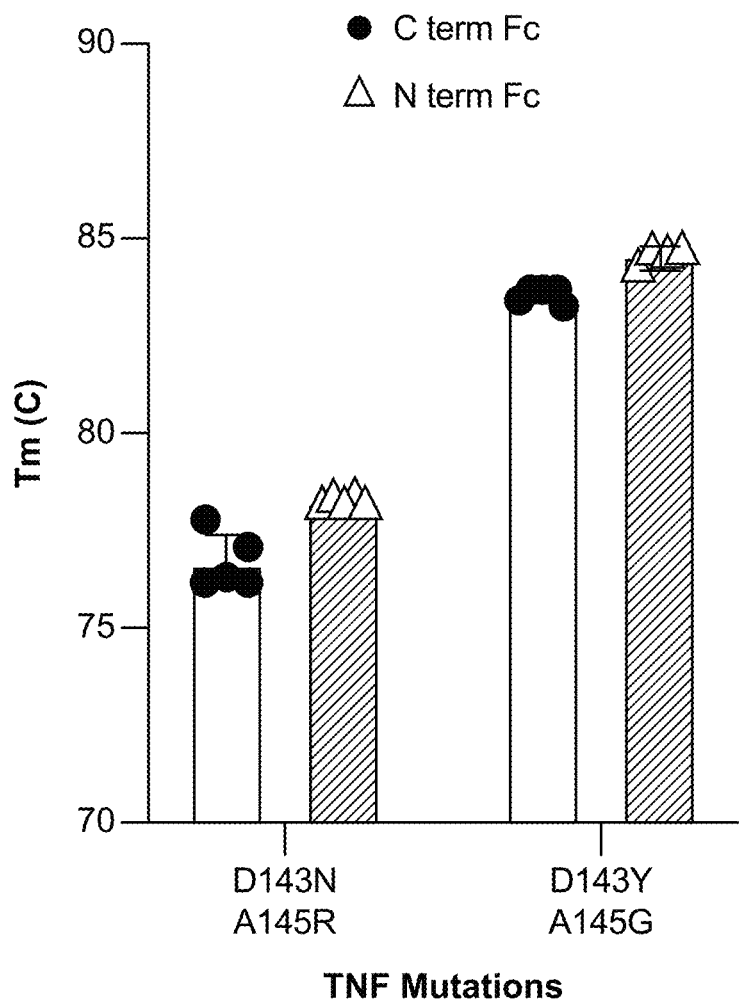
FIG. 2 is a bar graph depicting, from left to right, the melting temperature (Tm) of Variant 3 (D143N/A145R, C-terminal Fc), Variant 4 (D143N/A145R, N-terminal Fc), Variant 5 (D143Y/A145G, C-terminal Fc), or Variant 6 (D143Y/A145G, N-terminal Fc) TNF-alpha variant fusion molecules, as determined by differential scanning fluorimetry from multiple measurements.

Briefly, the melting temperature (Tm) of TNF-alpha variant fusion molecules Variant 3, Variant 4, Variant 5, and Variant 6 was analyzed by differential scanning fluorimetry (DSF). DSF was conducted using standard methods, where protein denaturation was monitored over a range of increasing temperatures using real time PCR to measure changes in fluorescence of a dye that preferentially binds to unfolded protein. Tm was determined as the temperature at which 50% of the protein monomer is 50% denatured. Calculated Tm data is shown in Table 3 and FIG. 2.

Variant 5 and Variant 6 were each found to exhibit higher melting temperatures relative to Variant 3 and Variant 4. These data indicate that TNF-alpha variant fusion molecules comprising the D143Y/A145G double mutation (i.e., Variant 5 and Variant 6) have greater thermal stability for the single chain TNF portion of the molecule, as measured via Tm, than those with the D143N/A145R double mutation (i.e., Variant 3 and Variant 4). Furthermore, Variant 6 and Variant 4 exhibited greater Tm than did Variant 5 and Variant 3, respectively. The CH2 and CH3 domains of the Fc, which unfold at approximately 68° C. and 81° C. respectively, were similar across all constructs

TABLE 3

Melting temperature of TNF-alpha variant fusion molecules

| Name | Tm (° C.) |
| --- | --- |
| Variant 3 | 75.1 |
| Variant 4 | 78.1 |
| Variant 5 | 83.7 |
| Variant 6 | 84.6 |

Example 4: TNF-Alpha Variant Fusion Molecule Aggregation Assessment During Freeze/Thaw Cycles This Example assesses sample aggregation of Variant 3, Variant 4, Variant 5, and Variant 6 after freeze/thaw cycling.

TNF-alpha variant fusion molecule samples were subject to freeze/thaw (FT) cycling at a concentration of 10 mg/ml in histidine buffer (10 mM Histidine pH 6, 120 mM NaCl). After cycling, Variant 3, Variant 4, Variant 5, and Variant 6 all exhibited similar percent retention of monomer in sample, indicating that the D143Y/A145G double mutation did not substantially alter the freeze/thaw induced aggregation of the relevant TNF-alpha variant fusion molecules relative to TNF-alpha variant fusion molecules comprising the D143N/A145R mutations. Data is shown in

TABLE 4

Percentage of Monomer from 10 mg/ml TNF-alpha Variant Fusion Molecule Sample After Freeze/Thaw Cycling

| Name | % Monomer (starting) | % Monomer (FT cycle 1) |
| --- | --- | --- |
| Variant 3 | 99.8 | 99.8 |
| Variant 4 | 99.9 | 99.9 |
| Variant 5 | 99.8 | 99.8 |
| Variant 6 | N/A | 99.5 |

Example 5: Affinity and Selectivity of TNF-Alpha Variant Fusion Molecules

Loetscher et al. "Human tumor necrosis factor alpha (TNF alpha) mutants with exclusive specificity for the 55-kDa or 75-kDa TNF receptors." *J Biol Chem.* (1993); 268(35): 26350-7, previously reported the effect of incorporating select mutations into TNFα molecules on binding affinity and selectivity between TNFα and TNFR-p55 (i.e., human TNFR1) or TNFR-p75 (i.e., human TNFR2) receptor molecules. In particular, single mutations at amino acid residues Asp143 (D143) and Ala145 (A145) were observed to produce TNFα molecules that largely retained binding to TNFR2 but lost considerable binding affinity to TNFR1 (Loetscher et al. at page 26356, paragraph 3). For example, a mutation of D143N resulted in a several thousand fold loss in binding affinity for TNFR1, whereas the loss in binding affinity for TNFR2 was about 10-fold (Loetscher et al. at page 26353, paragraph 2). Similarly, a mutation of D145R was reported to retain full binding activity for TNFR2, but decreased binding to TNFR1 by about 2,500-fold (Loetscher et al. at page 26353, paragraph 2). Additionally, Loetscher et al. reported that combining the single mutations (D143N and A145R) yielded a double mutant TNFα molecule, D143N/A145R, with enhanced selectivity for TNFR2, with the contribution of the two mutations in combination being roughly additive (Loetscher et al. at page 26353, paragraph 2).

This Example assesses the affinity and selectivity of TNF-alpha variant fusion molecules for TNFR2.

The binding affinity and selectivity of TNF-alpha variant fusion molecules for human TNFR2 (hTNFR2) and human TNFR1 (hTNFR1) receptors was analyzed by bio-layer interferometry (BLI). BLI binding studies were conducted using standard methods, where recombinant TNF-alpha variant fusion molecule was immobilized on the biosensor tip for experimentation. All experiments were performed at 30° C. with shaking at 1,000 r.p.m, and anti-IgG Fc biosensors were pre-equilibrated in K buffer, consisting of a 1/10 dilution of 0.2% BSA, 0.02% Tween20, 0.05% ProClin300 into PBS (138 mM NaCl, 2.7 mM KCl pH 7.4) for at least 300 seconds before use in experiments. 2 g/mL TNF-alpha variant fusion molecule was loaded onto anti-IgG Fc biosensors until a loading height of 0.6 nm was reached and flowed the difference in concentrations of hTNFR2 or hTNFR1, or buffer as control, for 200 seconds. Then both dissociate in K buffer for 400 seconds. Data was analyzed using standard methods. Calculated binding affinity is seen in Table 5.

TABLE 5

Binding affinity of TNF-alpha variant fusion molecules to hTNFR2 and hTNFR1

| Name | hTNFR2 Kd [M] | hTNFR1 Kd [M] |
|---|---|---|
| Wild-type | 3.40E−08 | 7.65E−09 |
| Variant 1 | 1.22E−07 | 3.18E−06 |
| Variant 2 | 6.76E−08 | 3.33E−07 |
| Variant 3 | 2.38E−07 | NB* |
| Variant 4 | 2.10E−07 | NB* |
| Variant 5 | 2.58E−07 | NB* |
| Variant 6 | 1.64E−07 | NB* |

*NB: no binding detected

In comparison to the wild-type TNF-alpha variant fusion molecule, Variant 1 exhibited a 3.6-fold decrease in binding affinity for hTNFR2 and a 415.7-fold decrease in binding affinity for hTNFR1, while Variant 2 exhibited a 2.0-fold decrease in binding affinity for hTNFR2 and a 43.5-fold decrease in binding affinity for hTNFR1. Variant 3 and Variant 4, i.e., double mutant TNF-alpha variant fusion molecules that incorporate both D143N and A145R mutations, exhibited a 7.0-fold (Variant 3) and 6.2-fold (Variant 4) decrease in binding affinity for hTNFR2, and no binding affinity for hTNFR1. Variant 5 and Variant 6, i.e., double mutant TNF-alpha variant fusion molecules that incorporate D143Y and A145G mutations, exhibited a 7.6-fold (Variant 5) and 4.8-fold (Variant 6) decrease in binding affinity for hTNFR2 and no detected binding affinity for hTNFR1.

Thus, similar to results reported by Loetscher et al., TNF-alpha variant fusion molecules comprising a D143N (Variant 1) or A145R (Variant 2) single mutation largely retained binding to hTNFR2 but lost considerable binding affinity for hTNFR1. Furthermore, TNF-alpha variant fusion molecules comprising a D143N/A145R double mutation (i.e., Variant 3 and Variant 4) exhibited binding characteristics that were roughly additive of the single mutant molecules, which is consistent with results reported by Loetscher et al. (page 26353, paragraph 2). In contrast, Variant 5 and Variant 6 exhibited similar binding affinities and selectivity for hTNFR2 when compared to Variant 3 and Variant 4. This result was unexpected because the A145G single mutation variant reported by Loetscher et al. had a limited effect in reducing binding affinity for hTNFR1 when compared to other single mutant variants tested, including A145R (Loetscher et al. at page 26353, Table I). Notably, of the eleven A145 single mutation variants tested by Loetscher et al., the A145R single mutation exhibited the lowest $ID_{50}$ ratio (<0.03 $ID_{50}$ ratio), followed by the A145F (0.04 $ID_{50}$ ratio) and A145K (0.05 $ID_{50}$ ratio) single mutations, whereas the A145G (0.4 $ID_{50}$ ratio) single mutation variant exhibited the sixth lowest $ID_{50}$ ratio (Loetscher et al. at page 26353, Table I), suggesting that the A145G mutation alone does not confer significant specificity.

Example 6: TNF-Alpha Variant Fusion Molecules Bind TNFR2-Expressing Cells

This Example describes binding of the TNF-alpha variant fusion molecules described in the above examples to TNFR2.

Flow Cytometry Analysis of Binding to TNFR2-Expressing HEK293 Cells

The ability of TNF-alpha variant fusion molecules to bind to TNFR2-expressing cells was analyzed by flow cytometry. Specifically, binding of recombinant TNF-alpha variant fusion molecules was assessed against cells engineered to express human TNFR2 (HEK293-NF-kB/Luc-TNFR2 cells) and cells that are TNFR2-negative (negative control; HEK293-NF-kB/Luc cells).

Briefly, cell monolayers grown in tissue culture flasks were trypsinized, counted, and stained with Zombie Violet Fixable Viability Stain (ZV stain added to PBS at a 1:200 dilution) according to manufacturer's instructions. These stained cells were then incubated with TNF-alpha variant fusion molecules prepared at different concentrations in a staining buffer composed of 1×PBS, 2% fetal bovine serum, and 1 mM EDTA. The cells were incubated with the molecules for 30 minutes on ice, before unbound molecules were removed by centrifugation and aspiration. The cells were then incubated for 30 minutes on ice with a fluorescently-conjugated antibody that recognizes the human IgG Fc domain, prepared in staining buffer. Samples were washed twice with staining buffer to remove all unbound articles and then analyzed on a flow cytometer.

Figure 3:
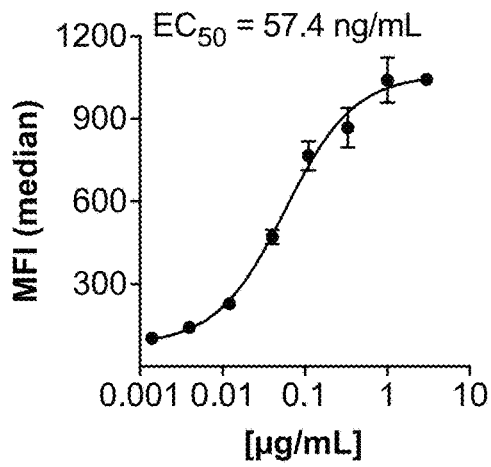
FIG. 3 shows dose response curves depicting binding of Variant 3, Variant 4, Variant 5, or Variant 6 TNF-alpha variant fusion molecules to TNFR2-expressing HEK293 cells or TNFR2-negative cells (as a control), as determined by flow cytometry. Binding is represented by MFI values plotted as a function of concentration of TNF-alpha variant fusion molecule, wherein EC50 corresponds to the half-maximal effective concentration of TNF-alpha variant fusion molecule.
Figure 3:
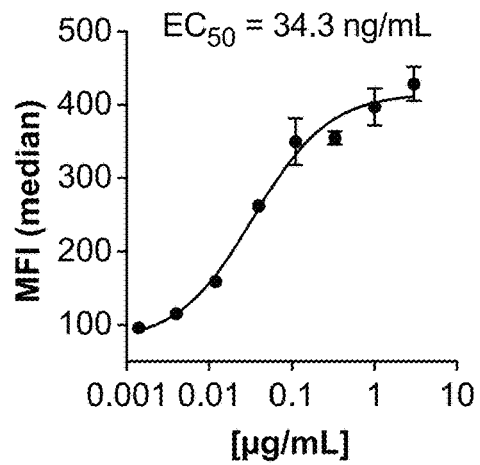
Figure 3:
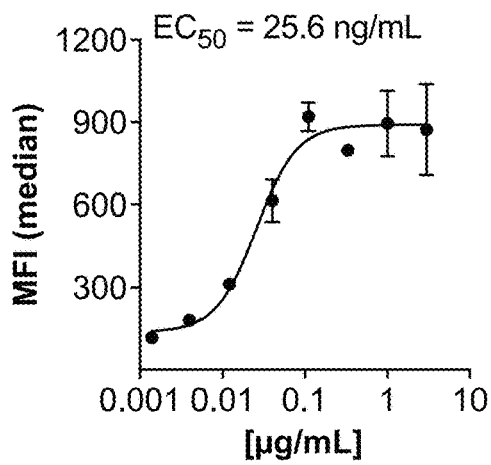
Figure 3:
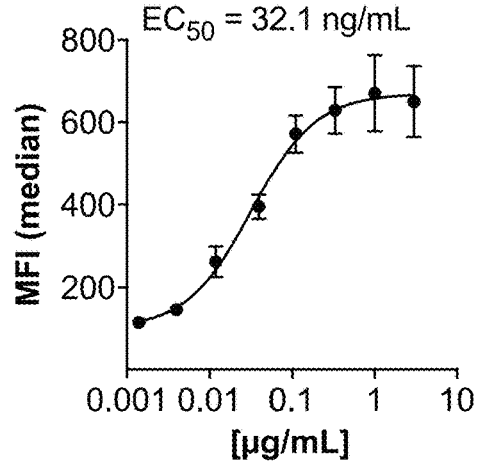
Figure 3:
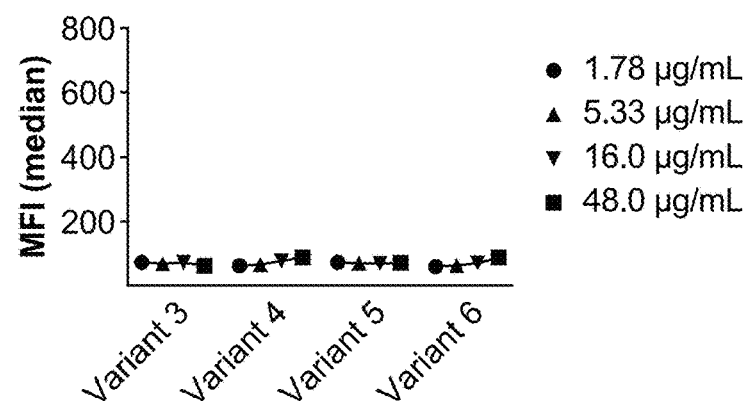

Data is shown in FIG. 3. Binding affinity of the D143Y/A145G TNF-alpha variant fusion molecule (i.e., Variant 5) to TNFR2-expressing HEK cells ($EC_{50}$=25.6 ng/mL) was comparable to that of Variant 3 ($EC_{50}$=57.4 ng/mL). None of the TNF-alpha variant fusion molecules tested (i.e., Variants 3, 4, 5, and 6) showed non-specific binding to TNFR2-negative control cells.

NF-kB-Luciferase Assay in TNFR2-Expressing HEK293 Cells

The ability of TNF-alpha variant fusion molecules to bind to TNFR2-expressing cells and to induce the activity of TNFR2 was analyzed by an NF-kB-Luciferase assay. As above, TNF-alpha variant fusion molecules were assessed against cells engineered to express human TNFR2 (HEK293-NFkB/Luc-TNFR2 cells) and cells that are TNFR2-negative (negative control; HEK293-NFkB/Luc cells). Briefly, cells were incubated with TNF-alpha variant fusion molecules at different concentrations in DMEM media supplemented with 10% fetal bovine serum for 5 hours at 37° C. in a humidity-controlled incubator at 5% $CO_2$. At the end of the incubation, luciferase substrate was added according to the manufacturer's instructions. The samples were incubated for 2 minutes at room temperature and then the luminescence was measured.

Figure 4:
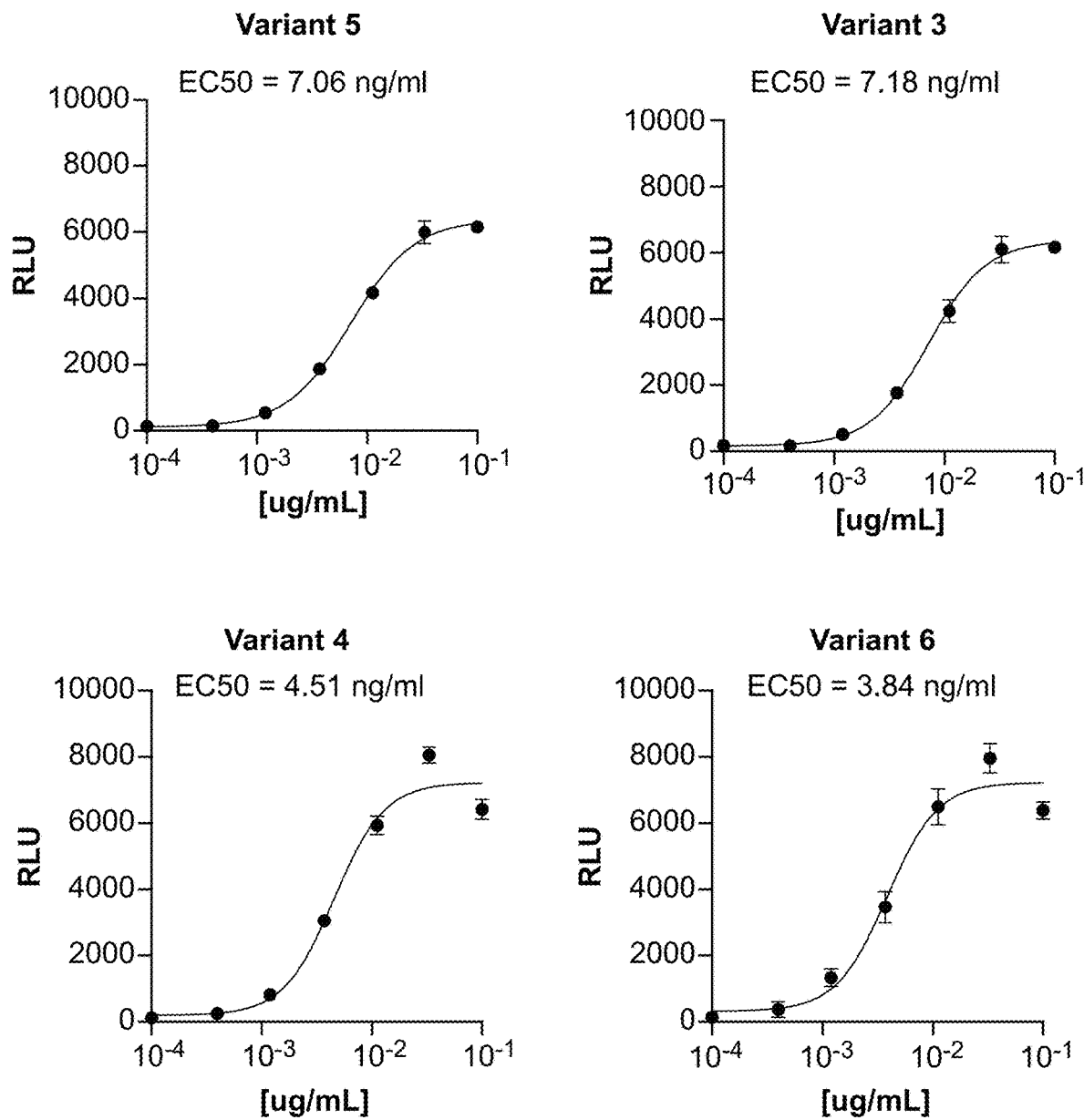
FIG. 4 shows dose response curves depicting the ability of Variant 3, Variant 4, Variant 5, or Variant 6 TNF-alpha variant fusion molecules to bind to TNFR2-expressing HEK293 cells and to induce the activity of TNFR2, as determined by NFkB-Luciferase assay. The functional potencies are represented by relative luminescence units (RLU) plotted as a function of concentration of TNF-alpha variant fusion molecule, wherein EC50 corresponds to the half-maximal effective concentration of TNF-alpha variant fusion molecule.

Data is shown in FIG. 4. Double mutant TNF-alpha variant fusion molecules with a C-terminal Fc yielded similar functional potencies: $EC_{50}$=7.06 ng/mL for Variant 5, and $EC_{50}$=7.18 ng/mL for Variant 3. Likewise, double mutant TNF-alpha variant fusion molecules with an N-terminal Fc exhibited similar functional potencies: $EC_{50}$=3.84 ng/mL for Variant 6, and $EC_{50}$=4.51 ng/mL for Variant 4. These data demonstrate that Variants 3, 4, 5 and 6 TNF-alpha variant fusion molecules are functionally active. TNFR2-negative cells incubated with TNF-alpha variant fusion molecules lacked activity, while TNFR2-negative cells incubated with wild-type TNF-alpha exhibited robust activity (data not shown).

Example 7: TNF-Alpha Variant Fusion Molecule Aggregation and Fragmentation in Accelerated Conditions This Example assesses sample aggregation and fragmentation of TNF-alpha variant fusion molecules after incubation in buffer at 40° C.

Figure 5A:
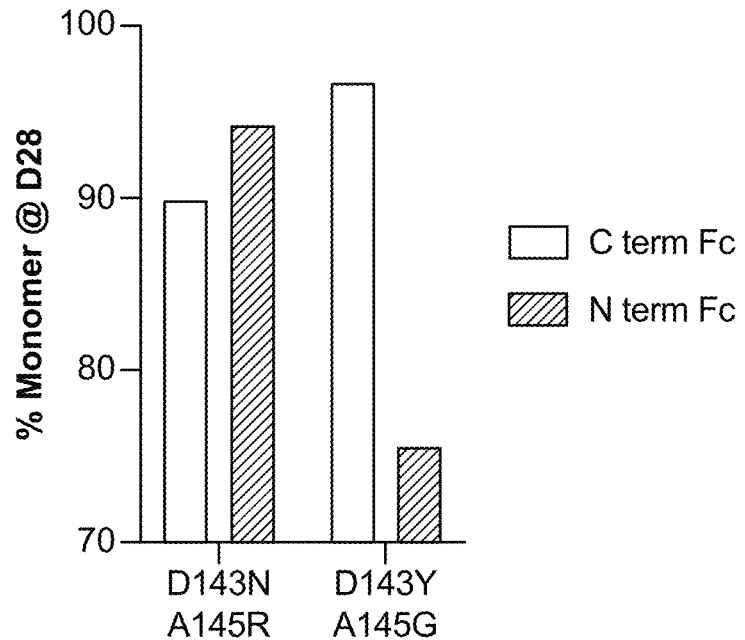
FIGS. 5A-5B show the stability of Variant 3, Variant 4, Variant 5, or Variant 6 TNF-alpha variant fusion molecules after incubation in histidine buffer at 40° C., as determined by HPLC-SEC analysis.
Figure 5B:
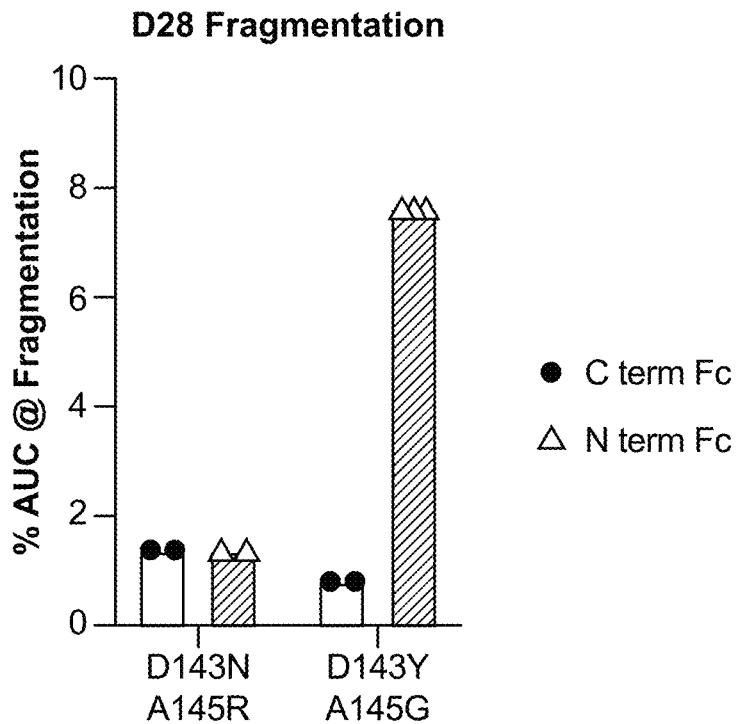

HPLC-SEC Assessment of Accelerated Conditions on 10 mg mL Samples Incubated in Histidine Buffer Over 28 Days TNF-alpha variant fusion molecule samples including Variant 3, Variant 4, Variant 5, and Variant 6 were incubated at a concentration of 10 mg/mL in histidine buffer (10 mM Histidine pH 6, 120 mM NaCl) for a period of 28 days at 40° C. The percentage of monomeric protein retained in sample at day 28 (results shown in FIG. 5A) and the percentage of sample fragmentation at day 28 (results shown in FIG. 5B) was determined via HPLC-SEC analysis.

Figure 6:
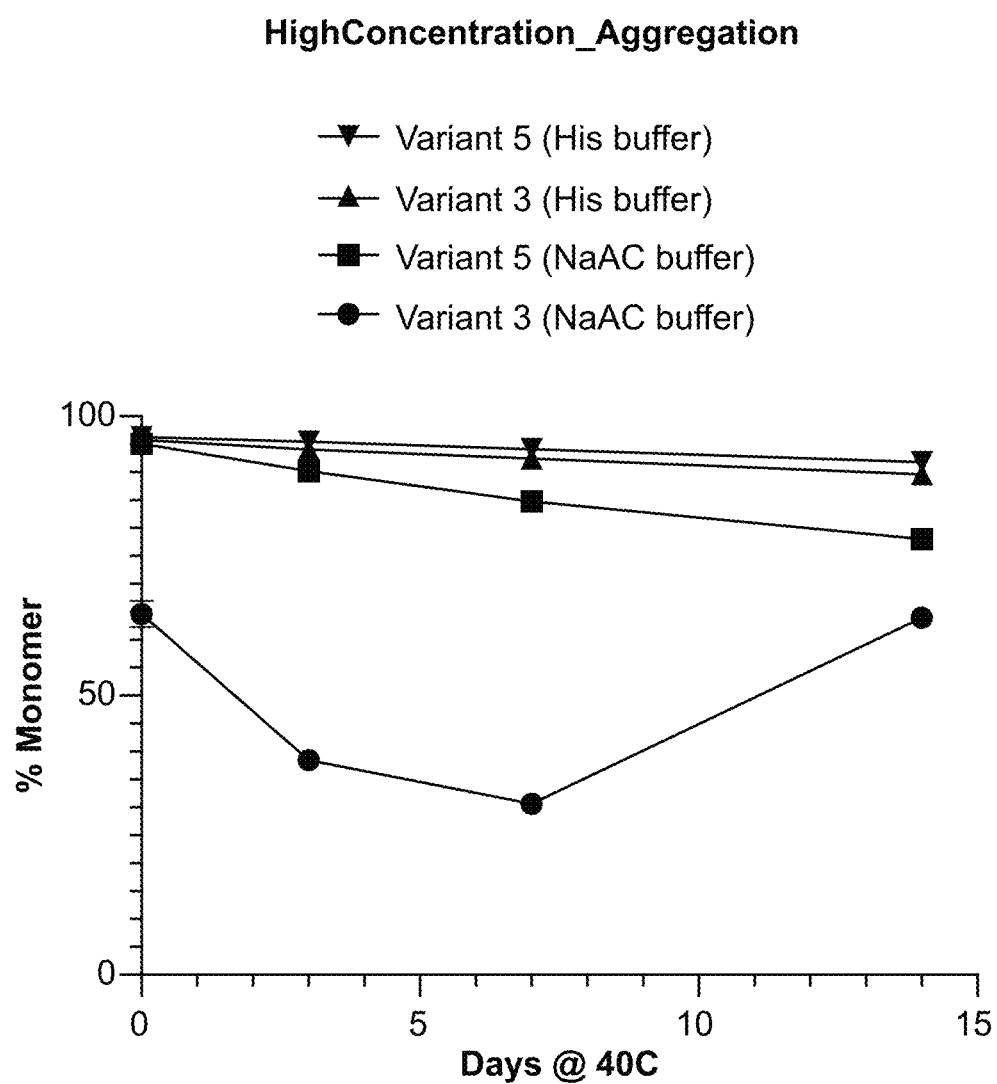
FIG. 6 shows the stability of Variant 3 and Variant 5 TNF-alpha variant fusion molecules incubated in histidine buffer or sodium acetate buffer at 40° C. for 14 days, as determined by HPLC-SEC analysis. The percentage of monomer retained in sample is plotted after 0, 3, 7, and 14 days of incubation at 40° C. for Variant 3 (D143N/A145R) in sodium acetate buffer fusion partner is located at a N-terminus of the TNF-alpha variant molecule. A TNF-alpha variant fusion molecule in which the fusion is an Fc domain may also be referred to herein as a "TNF-alpha variant Fc fusion polypeptides" or "TNF-alpha variant Fc fusion". Nonlimiting exemplary TNF-alpha variant Fc fusion polypeptides are shown in the amino acid sequences of any one of SEQ ID NOs: 19-24, including those sequences with or without their associated signal peptides.

After incubation in buffer for 28 days at 40° C., Variant 5 exhibited a higher percentage of monomeric protein relative to Variant 3 and Variant. In contrast, Variant 6 exhibited the lowest relative percentage of monomer after incubation. By comparison, Variant 6 exhibited a higher percentage of sample fragmentation relative to Variant 3 and Variant 4, while Variant 5 exhibited the lowest relative percentage of sample fragmentation of all samples tested. These data demonstrate that Variant 5, a TNF-alpha variant fusion molecule comprising a C-terminal Fc and the D143Y/A145G double mutation, has a reduced propensity to become fragmented or to form aggregate when incubated in buffer at 40° C. relative to D143N/A145R double mutant variants (i.e., Variant 3 and Variant 4) or the D143Y/A145G double mutant variant with an N-terminal Fc (i.e., Variant 6). HPLC-SEC Assessment of Accelerated Conditions on >50 mg mL Samples Incubated in Histidine or Sodium Acetate Buffer Over 14 Days Variant 5 and Variant 3 TNF-alpha variant fusion molecule samples were concentrated via spin concentrator to above 50 mg/mL in histidine buffer (10 mM Histidine pH 6, 120 mM NaCl, 9% sucrose) or sodium acetate buffer (10 mM NaAcetate pH 5.2, 120 mM NaCl, 9% sucrose) and incubated at room temperature for 40 days. At day 0, all four conditions started at 100% monomer (i.e., Day 0 at room temperature). After 41 days, samples were spun down to remove precipitate and the percentage of monomer retained in aqueous phase in sample was assessed via HPLC-SEC analysis. Sample concentrations were then normalized to 57 mg/mL, and samples were incubated at 40° C. for an additional 14 days. The percentage of monomer retained in sample after incubation for 0, 3, 7, and 14 days at 40° C. (results shown in FIG. 6) was determined via HPLC-SEC analysis.

After 40 days incubation at room temperature, Variant 3 in sodium acetate buffer started incubation at 40° C. (i.e., at Day 0 of incubation at 40° C.) with ~65% monomer in solution, while Variant 5 in sodium acetate, and Variants 3 and 5 in histidine buffer started incubation at 40° C. (i.e., also at Day 0 of incubation at 40° C.) with ~100% monomer in solution. After the additional incubation for 14 days at 40° C. in histidine buffer, Variant 5 exhibited a higher retention of percentage of monomer relative to Variant 3. Similarly, after incubation for 14 days at 40° C. in sodium acetate buffer, Variant 5 exhibited a higher percentage of monomer relative to Variant 3. These data demonstrate that Variant 5, a TNF-alpha variant fusion molecule comprising a C-terminal Fc and the D143Y/A145G double mutation, is stable at high concentration in 10 mM histidine buffer. Furthermore, the data show that Variant 5 has a reduced propensity to form aggregate when incubated in 10 mM histidine buffer at 40° C. relative to the Variant 3, a TNF-alpha variant fusion molecule comprising a C-terminal Fc and D143N/A145R double mutation.

Figure 7:
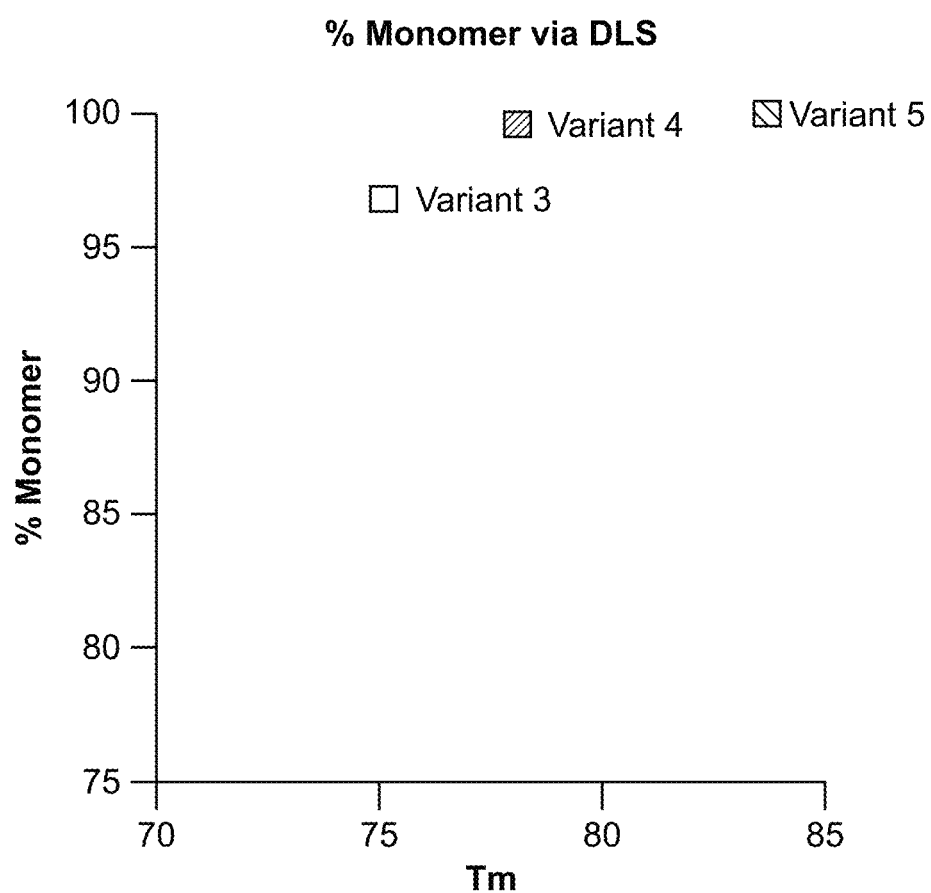

Dynamic Light Scattering Assessment of Accelerated Conditions on 10 mg mL Samples Incubated in Histidine Buffer Over 28 Days TNF-alpha variant fusion molecule samples consisting of Variant 3, Variant 4 or Variant 5 were incubated at a concentration of 10 mg/mL in histidine buffer (10 mM Histidine pH 6, 120 mM NaCl) for a period of 28 days at 40° C. The percentage of monomer retained in sample at day 28 (results shown in FIG. 7) was determined via dynamic light scattering (% mass measured at ~10 nm).

After incubation in buffer for 28 days at 40° C., Variant 5 (100%) exhibited a higher percentage of monomer relative to Variant 3 (96.8%) and Variant 4 (99.6%). These data demonstrate that Variant 5, a TNF-alpha variant fusion molecule comprising a C-terminal Fc and the D143Y/A145G double mutation, has a reduced propensity to form aggregate when incubated in buffer at 40° C. relative to D143N/A145R double mutant variants (i.e., Variant 3 and Variant 4).

Example 8: TNF-Alpha Variant Fusion Molecule Stability in Serum

This Example assesses the serum stability of TNF-alpha variant fusion molecules Variant 3, Variant 4, and Variant 5.

Figure 8:
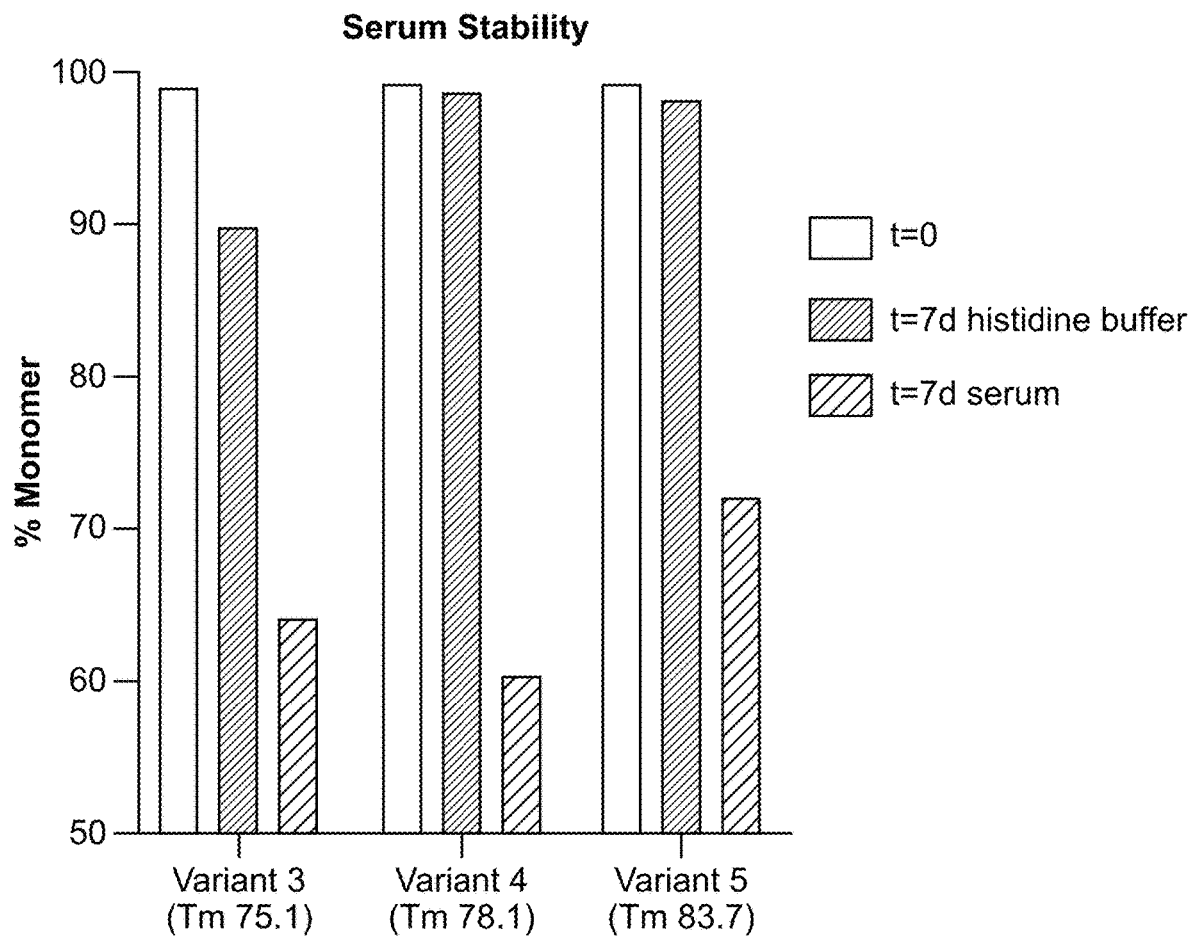

TNF-alpha variant fusion molecule samples were incubated in human serum or buffer for 7 days at 40° C. The percentage of monomer retained in sample at time 0, at day 7 in histidine buffer, or at day 7 in serum, was determined via SEC analysis (results shown in FIG. 8).

Variant 5 exhibited a higher percentage of monomer after 7 days incubation at 40° C. in serum relative to Variant 3 and Variant 4. These data indicate that Variant 5, a TNF-alpha variant fusion molecule comprising a C-terminal Fc and the D143Y/A145G double mutation, has increased serum stability at 40° C. relative to D143N/A145R double mutant variants (i.e., Variant 3 and Variant 4).

Example 9: TNF-Alpha Variants Fusion Molecule Hydrophobicity

This Example assesses the hydrophobicity of Variant 3, Variant 4, and Variant 5, one over several assays used to predict non-specific binding, solubility, and solution properties of protein based drugs.

For each TNF-alpha variant fusion molecule, 10 L of sample was injected into a Sepax Proteomix HIC butyl-NP 1.7, 4.6×35 mm column with a flow of 0.8 mL/min. Mobile phase started as 60% of Buffer C (1.8 M (NH4)2SO4, 0.1 M NaH2PO4, pH 6.5) and 40% of Buffer D (0.1 M NaH2PO4, pH 6.5) and changed in linear gradient to 0% of buffer C and 100% of buffer D from 1 min to 16 min. Signal was measured at 280 nm. The hydrophobic stability of the TNF-alpha variant fusion molecules was analyzed via hydrophobic interaction chromatography (HIC). Data is shown in Table 6.

Variant 5 exhibited a retention time similar to that of Variant 3 and Variant 4. These data indicate that for Variant 5, the D143Y/A145G TNF double mutation does not significantly alter the hydrophobic stability of the molecule relative to that of TNF-alpha variant fusion molecules comprising the D143N/A145R mutations (i.e., Variant 3 and Variant 4).

TABLE 6

Retention Time of TNF-alpha Variant Fusion Molecule Samples

| Name | HIC Elution time (min) |
|---|---|
| Variant 3 | 4.27 |
| Variant 4 | 3.39 |
| Variant 5 | 4.68 |

SEQUENCE LISTING

| Name | SEQ ID NO | Sequence |
|---|---|---|
| Wild type TNF-alpha | 1 | VRSSSRTPSDKPVAHVVANPQAEGQLQWLNRRANALLANGVELR DNQLVVPSEGLYLIYSQVLFKGQGCPSTHVLLTHTISRIAVSYQTKV NLLSAIKSPCQRETPEGAEAKPWYEPIYLGGVFQLEKGDRLSAEINR PDYLDFAESGQVYFGIIAL |
| Wild type TNF-alpha variant without N-terminal "VRS" | 2 | SSRTPSDKPVAHVVANPQAEGQLQWLNRRANALLANGVELRDNQ LVVPSEGLYLIYSQVLFKGQGCPSTHVLLTHTISRIAVSYQTKVNLL SAIKSPCQRETPEGAEAKPWYEPIYLGGVFQLEKGDRLSAEINRPD YLDFAESGQVYFGIIAL |
| D143N TNF-alpha variant | 3 | VRSSSRTPSDKPVAHVVANPQAEGQLQWLNRRANALLANGVELR DNQLVVPSEGLYLIYSQVLFKGQGCPSTHVLLTHTISRIAVSYQTKV NLLSAIKSPCQRETPEGAEAKPWYEPIYLGGVFQLEKGDRLSAEINR PDYLNFAESGQVYFGIIAL |
| D143N TNF-alpha variant without N-terminal "VRS" | 4 | SSRTPSDKPVAHVVANPQAEGQLQWLNRRANALLANGVELRDNQ LVVPSEGLYLIYSQVLFKGQGCPSTHVLLTHTISRIAVSYQTKVNLL SAIKSPCQRETPEGAEAKPWYEPIYLGGVFQLEKGDRLSAEINRPD YLNFAESGQVYFGIIAL |
| A145R TNF-alpha variant | 5 | VRSSSRTPSDKPVAHVVANPQAEGQLQWLNRRANALLANGVELR DNQLVVPSEGLYLIYSQVLFKGQGCPSTHVLLTHTISRIAVSYQTKV NLLSAIKSPCQRETPEGAEAKPWYEPIYLGGVFQLEKGDRLSAEINR PDYLDFRESGQVYFGIIAL |
| A145R TNF-alpha variant without N-terminal "VRS" | 6 | SSRTPSDKPVAHVVANPQAEGQLQWLNRRANALLANGVELRDNQ LVVPSEGLYLIYSQVLFKGQGCPSTHVLLTHTISRIAVSYQTKVNLL SAIKSPCQRETPEGAEAKPWYEPIYLGGVFQLEKGDRLSAEINRPD YLDFRESGQVYFGIIAL |
| D143N, A145R TNF-alpha variant | 7 | VRSSSRTPSDKPVAHVVANPQAEGQLQWLNRRANALLANGVELR DNQLVVPSEGLYLIYSQVLFKGQGCPSTHVLLTHTISRIAVSYQTKV NLLSAIKSPCQRETPEGAEAKPWYEPIYLGGVFQLEKGDRLSAEINR PDYLNFRESGQVYFGIIAL |
| D143N, A145R TNF-alpha variant without N-terminal "VRS" | 8 | SSRTPSDKPVAHVVANPQAEGQLQWLNRRANALLANGVELRDNQ LVVPSEGLYLIYSQVLFKGQGCPSTHVLLTHTISRIAVSYQTKVNLL SAIKSPCQRETPEGAEAKPWYEPIYLGGVFQLEKGDRLSAEINRPD YLNFRESGQVYFGIIAL |
| D143Y, A145G TNF-alpha variant | 9 | VRSSSRTPSDKPVAHVVANPQAEGQLQWLNRRANALLANGVELR DNQLVVPSEGLYLIYSQVLFKGQGCPSTHVLLTHTISRIAVSYQTKV NLLSAIKSPCQRETPEGAEAKPWYEPIYLGGVFQLEKGDRLSAEINR PDYLYFGESGQVYFGIIAL |
| D143Y, A145G TNF-alpha variant without N-terminal "VRS" | 10 | SSRTPSDKPVAHVVANPQAEGQLQWLNRRANALLANGVELRDNQ LVVPSEGLYLIYSQVLFKGQGCPSTHVLLTHTISRIAVSYQTKVNLL SAIKSPCQRETPEGAEAKPWYEPIYLGGVFQLEKGDRLSAEINRPD YLYFGESGQVYFGIIAL |
| Wild type TNF-alpha variant molecule | 11 | VRSSSRTPSDKPVAHVVANPQAEGQLQWLNRRANALLANGVELR DNQLVVPSEGLYLIYSQVLFKGQGCPSTHVLLTHTISRIAVSYQTKV NLLSAIKSPCQRETPEGAEAKPWYEPIYLGGVFQLEKGDRLSAEINR PDYLDFAESGQVYFGIIALGGGGSSSRTPSDKPVAHVVANPQAEGQ LQWLNRRANALLANGVELRDNQLVVPSEGLYLIYSQVLFKGQGCP STHVLLTHTISRIAVSYQTKVNLLSAIKSPCQRETPEGAEAKPWYEP IYLGGVFQLEKGDRLSAEINRPDYLDFAESGQVYFGIIALGGGGSSS RTPSDKPVAHVVANPQAEGQLQWLNRRANALLANGVELRDNQLV VPSEGLYLIYSQVLFKGQGCPSTHVLLTHTISRIAVSYQTKVNLLSA IKSPCQRETPEGAEAKPWYEPIYLGGVFQLEKGDRLSAEINRPDYL DFAESGQVYFGIIAL |
| D143N TNF-alpha variant molecule | 12 | VRSSSRTPSDKPVAHVVANPQAEGQLQWLNRRANALLANGVELR DNQLVVPSEGLYLIYSQVLFKGQGCPSTHVLLTHTISRIAVSYQTKV NLLSAIKSPCQRETPEGAEAKPWYEPIYLGGVFQLEKGDRLSAEINR PDYLNFAESGQVYFGIIALGGGGSSSRTPSDKPVAHVVANPQAEGQ LQWLNRRANALLANGVELRDNQLVVPSEGLYLIYSQVLFKGQGCP |

-continued

SEQUENCE LISTING

| Name | SEQ ID NO | Sequence |
|---|---|---|
| | | STHVLLTHTISRIAVSYQTKVNLLSAIKSPCQRETPEGAEAKPWYEP IYLGGVFQLEKGDRLSAEINRPDYLNFAESGQVYFGIIALGGGGSSS RTPSDKPVAHVVANPQAEGQLQWLNRRANALLANGVELRDNQLV VPSEGLYLIYSQVLFKGQGCPSTHVLLTHTISRIAVSYQTKVNLLSA IKSPCQRETPEGAEAKPWYEPIYLGGVFQLEKGDRLSAEINRPDYL NFAESGQVYFGIIAL |
| A145R TNF-alpha variant molecule | 13 | VRSSSRTPSDKPVAHVVANPQAEGQLQWLNRRANALLANGVELR DNQLVVPSEGLYLIYSQVLFKGQGCPSTHVLLTHTISRIAVSYQTKV NLLSAIKSPCQRETPEGAEAKPWYEPIYLGGVFQLEKGDRLSAEINR PDYLDFRESGQVYFGIIALGGGGSSSRTPSDKPVAHVVANPQAEGQ LQWLNRRANALLANGVELRDNQLVVPSEGLYLIYSQVLFKGQGCP STHVLLTHTISRIAVSYQTKVNLLSAIKSPCQRETPEGAEAKPWYEP IYLGGVFQLEKGDRLSAEINRPDYLDFRESGQVYFGIIALGGGGSSS RTPSDKPVAHVVANPQAEGQLQWLNRRANALLANGVELRDNQLV VPSEGLYLIYSQVLFKGQGCPSTHVLLTHTISRIAVSYQTKVNLLSA IKSPCQRETPEGAEAKPWYEPIYLGGVFQLEKGDRLSAEINRPDYL DFRESGQVYFGIIAL |
| D143N, A145R TNF-alpha variant molecule | 14 | VRSSSRTPSDKPVAHVVANPQAEGQLQWLNRRANALLANGVELR DNQLVVPSEGLYLIYSQVLFKGQGCPSTHVLLTHTISRIAVSYQTKV NLLSAIKSPCQRETPEGAEAKPWYEPIYLGGVFQLEKGDRLSAEINR PDYLNFRESGQVYFGIIALGGGGSSSRTPSDKPVAHVVANPQAEGQ LQWLNRRANALLANGVELRDNQLVVPSEGLYLIYSQVLFKGQGCP STHVLLTHTISRIAVSYQTKVNLLSAIKSPCQRETPEGAEAKPWYEP IYLGGVFQLEKGDRLSAEINRPDYLNFRESGQVYFGIIALGGGGSSS RTPSDKPVAHVVANPQAEGQLQWLNRRANALLANGVELRDNQLV VPSEGLYLIYSQVLFKGQGCPSTHVLLTHTISRIAVSYQTKVNLLSA IKSPCQRETPEGAEAKPWYEPIYLGGVFQLEKGDRLSAEINRPDYL NFRESGQVYFGIIAL |
| D143Y, A145G TNF-alpha variant molecule | 15 | VRSSSRTPSDKPVAHVVANPQAEGQLQWLNRRANALLANGVELR DNQLVVPSEGLYLIYSQVLFKGQGCPSTHVLLTHTISRIAVSYQTKV NLLSAIKSPCQRETPEGAEAKPWYEPIYLGGVFQLEKGDRLSAEINR PDYLYFGESGQVYFGIIALGGGGSSSRTPSDKPVAHVVANPQAEGQ LQWLNRRANALLANGVELRDNQLVVPSEGLYLIYSQVLFKGQGCP STHVLLTHTISRIAVSYQTKVNLLSAIKSPCQRETPEGAEAKPWYEP IYLGGVFQLEKGDRLSAEINRPDYLYFGESGQVYFGIIALGGGGSSS RTPSDKPVAHVVANPQAEGQLQWLNRRANALLANGVELRDNQLV VPSEGLYLIYSQVLFKGQGCPSTHVLLTHTISRIAVSYQTKVNLLSA IKSPCQRETPEGAEAKPWYEPIYLGGVFQLEKGDRLSAEINRPDYL YFGESGQVYFGIIAL |
| Linker | 16 | GGGGS |
| IgG1 Fc | 17 | EPKSSDKTHTCPPCPAPEAAGGPSVFLFPPKPKDTLMISRTPEVTCV VVDVSHEDPEVKFNWYVDGVEVHNAKTKPREEQYNSTYRVVSVL TVLHQDWLNGKEYKCKVSNKALPASIEKTISKAKGQPREPQVYTL PPSRDELTKNQVSLTCLVKGFYPSDIAVEWESNGQPENNYKTTPPV LDSDGSFFLYSKLTVDKSRWQQGNVFSCSVMHEALHNHYTQKSLS LSPGK |
| Wild-type (Wild type TNF-alpha (C-term Fc) fusion molecule) | 18 | VRSSSRTPSDKPVAHVVANPQAEGQLQWLNRRANALLANGVELR DNQLVVPSEGLYLIYSQVLFKGQGCPSTHVLLTHTISRIAVSYQTKV NLLSAIKSPCQRETPEGAEAKPWYEPIYLGGVFQLEKGDRLSAEINR PDYLDFAESGQVYFGIIALGGGGSSSRTPSDKPVAHVVANPQAEGQ LQWLNRRANALLANGVELRDNQLVVPSEGLYLIYSQVLFKGQGCP STHVLLTHTISRIAVSYQTKVNLLSAIKSPCQRETPEGAEAKPWYEP IYLGGVFQLEKGDRLSAEINRPDYLDFAESGQVYFGIIALGGGGSSS RTPSDKPVAHVVANPQAEGQLQWLNRRANALLANGVELRDNQLV VPSEGLYLIYSQVLFKGQGCPSTHVLLTHTISRIAVSYQTKVNLLSA IKSPCQRETPEGAEAKPWYEPIYLGGVFQLEKGDRLSAEINRPDYL DFAESGQVYFGIIALGGGGSEPKSSDKTHTCPPCPAPEAAGGPSVFL FPPKPKDTLMISRTPEVTCVVVDVSHEDPEVKFNWYVDGVEVHNA KTKPREEQYNSTYRVVSVLTVLHQDWLNGKEYKCKVSNKALPASI EKTISKAKGQPREPQVYTLPPSRDELTKNQVSLTCLVKGFYPSDIAV EWESNGQPENNYKTTPPVLDSDGSFFLYSKLTVDKSRWQQGNVFS CSVMHEALHNHYTQKSLSLSPGK |
| Variant 1 (D143N (C-term Fc) TNF-alpha | 19 | VRSSSRTPSDKPVAHVVANPQAEGQLQWLNRRANALLANGVELR DNQLVVPSEGLYLIYSQVLFKGQGCPSTHVLLTHTISRIAVSYQTKV NLLSAIKSPCQRETPEGAEAKPWYEPIYLGGVFQLEKGDRLSAEINR PDYLNFAESGQVYFGIIALGGGGSSSRTPSDKPVAHVVANPQAEGQ |

-continued

SEQUENCE LISTING

| Name | SEQ ID NO | Sequence |
|---|---|---|
| variant fusion molecule) | | LQWLNRRANALLANGVELRDNQLVVPSEGLYLIYSQVLFKGQGCP STHVLLTHTISRIAVSYQTKVNLLSAIKSPCQRETPEGAEAKPWYEP IYLGGVFQLEKGDRLSAEINRPDYLNFAESGQVYFGIIALGGGGSSS RTPSDKPVAHVVANPQAEGQLQWLNRRANALLANGVELRDNQLV VPSEGLYLIYSQVLFKGQGCPSTHVLLTHTISRIAVSYQTKVNLLSA IKSPCQRETPEGAEAKPWYEPIYLGGVFQLEKGDRLSAEINRPDYL NFAESGQVYFGIIALGGGGSEPKSSDKTHTCPPCPAPEAAGGPSVFL FPPKPKDTLMISRTPEVTCVVVDVSHEDPEVKFNWYVDGVEVHNA KTKPREEQYNSTYRVVSVLTVLHQDWLNGKEYKCKVSNKALPASI EKTISKAKGQPREPQVYTLPPSRDELTKNQVSLTCLVKGFYPSDIAV EWESNGQPENNYKTTPPVLDSDGSFFLYSKLTVDKSRWQQGNVFS CSVMHEALHNHYTQKSLSLSPGK |
| Variant 2 (A145R (C-term Fc) TNF-alpha variant fusion molecule) | 20 | VRSSSRTPSDKPVAHVVANPQAEGQLQWLNRRANALLANGVELR DNQLVVPSEGLYLIYSQVLFKGQGCPSTHVLLTHTISRIAVSYQTKV NLLSAIKSPCQRETPEGAEAKPWYEPIYLGGVFQLEKGDRLSAEINR PDYLDFRESGQVYFGIIALGGGGSSSRTPSDKPVAHVVANPQAEGQ LQWLNRRANALLANGVELRDNQLVVPSEGLYLIYSQVLFKGQGCP STHVLLTHTISRIAVSYQTKVNLLSAIKSPCQRETPEGAEAKPWYEP IYLGGVFQLEKGDRLSAEINRPDYLDFRESGQVYFGIIALGGGGSSS RTPSDKPVAHVVANPQAEGQLQWLNRRANALLANGVELRDNQLV VPSEGLYLIYSQVLFKGQGCPSTHVLLTHTISRIAVSYQTKVNLLSA IKSPCQRETPEGAEAKPWYEPIYLGGVFQLEKGDRLSAEINRPDYL DFRESGQVYFGIIALGGGGSEPKSSDKTHTCPPCPAPEAAGGPSVFL FPPKPKDTLMISRTPEVTCVVVDVSHEDPEVKFNWYVDGVEVHNA KTKPREEQYNSTYRVVSVLTVLHQDWLNGKEYKCKVSNKALPASI EKTISKAKGQPREPQVYTLPPSRDELTKNQVSLTCLVKGFYPSDIAV EWESNGQPENNYKTTPPVLDSDGSFFLYSKLTVDKSRWQQGNVFS CSVMHEALHNHYTQKSLSLSPGK |
| Variant 3 (D143N, A145R (C-term Fc) TNF-alpha variant fusion molecule) | 21 | VRSSSRTPSDKPVAHVVANPQAEGQLQWLNRRANALLANGVELR DNQLVVPSEGLYLIYSQVLFKGQGCPSTHVLLTHTISRIAVSYQTKV NLLSAIKSPCQRETPEGAEAKPWYEPIYLGGVFQLEKGDRLSAEINR PDYLNFRESGQVYFGIIALGGGGSSSRTPSDKPVAHVVANPQAEGQ LQWLNRRANALLANGVELRDNQLVVPSEGLYLIYSQVLFKGQGCP STHVLLTHTISRIAVSYQTKVNLLSAIKSPCQRETPEGAEAKPWYEP IYLGGVFQLEKGDRLSAEINRPDYLNFRESGQVYFGIIALGGGGSSS RTPSDKPVAHVVANPQAEGQLQWLNRRANALLANGVELRDNQLV VPSEGLYLIYSQVLFKGQGCPSTHVLLTHTISRIAVSYQTKVNLLSA IKSPCQRETPEGAEAKPWYEPIYLGGVFQLEKGDRLSAEINRPDYL NFRESGQVYFGIIALGGGGSEPKSSDKTHTCPPCPAPEAAGGPSVFL FPPKPKDTLMISRTPEVTCVVVDVSHEDPEVKFNWYVDGVEVHNA KTKPREEQYNSTYRVVSVLTVLHQDWLNGKEYKCKVSNKALPASI EKTISKAKGQPREPQVYTLPPSRDELTKNQVSLTCLVKGFYPSDIAV EWESNGQPENNYKTTPPVLDSDGSFFLYSKLTVDKSRWQQGNVFS CSVMHEALHNHYTQKSLSLSPGK |
| Variant 4 (D143N, A145R (N-term Fc) TNF-alpha variant fusion molecule) | 22 | EPKSSDKTHTCPPCPAPEAAGGPSVFLFPPKPKDTLMISRTPEVTCV VVDVSHEDPEVKFNWYVDGVEVHNAKTKPREEQYNSTYRVVSVL TVLHQDWLNGKEYKCKVSNKALPASIEKTISKAKGQPREPQVYTL PPSRDELTKNQVSLTCLVKGFYPSDIAVEWESNGQPENNYKTTPPV LDSDGSFFLYSKLTVDKSRWQQGNVFSCSVMHEALHNHYTQKSLS LSPGKGGGGSVRSSSRTPSDKPVAHVVANPQAEGQLQWLNRRAN ALLANGVELRDNQLVVPSEGLYLIYSQVLFKGQGCPSTHVLLTHTI SRIAVSYQTKVNLLSAIKSPCQRETPEGAEAKPWYEPIYLGGVFQLE KGDRLSAEINRPDYLNFRESGQVYFGIIALGGGGSSSRTPSDKPVAH VVANPQAEGQLQWLNRRANALLANGVELRDNQLVVPSEGLYLIY SQVLFKGQGCPSTHVLLTHTISRIAVSYQTKVNLLSAIKSPCQRETP EGAEAKPWYEPIYLGGVFQLEKGDRLSAEINRPDYLNFRESGQVYF GIIALGGGGSSSRTPSDKPVAHVVANPQAEGQLQWLNRRANALLA NGVELRDNQLVVPSEGLYLIYSQVLFKGQGCPSTHVLLTHTISRIAV SYQTKVNLLSAIKSPCQRETPEGAEAKPWYEPIYLGGVFQLEKGDR LSAEINRPDYLNFRESGQVYFGIIAL |
| Variant 5 (D143Y, A145G (C-term Fc) TNF-alpha variant fusion molecule) | 23 | VRSSSRTPSDKPVAHVVANPQAEGQLQWLNRRANALLANGVELR DNQLVVPSEGLYLIYSQVLFKGQGCPSTHVLLTHTISRIAVSYQTKV NLLSAIKSPCQRETPEGAEAKPWYEPIYLGGVFQLEKGDRLSAEINR PDYLYFGESGQVYFGIIALGGGGSSSRTPSDKPVAHVVANPQAEGQ LQWLNRRANALLANGVELRDNQLVVPSEGLYLIYSQVLFKGQGCP STHVLLTHTISRIAVSYQTKVNLLSAIKSPCQRETPEGAEAKPWYEP IYLGGVFQLEKGDRLSAEINRPDYLYFGESGQVYFGIIALGGGGSSS RTPSDKPVAHVVANPQAEGQLQWLNRRANALLANGVELRDNQLV VPSEGLYLIYSQVLFKGQGCPSTHVLLTHTISRIAVSYQTKVNLLSA |

-continued

SEQUENCE LISTING

| Name | SEQ ID NO | Sequence |
|---|---|---|
| | | IKSPCQRETPEGAEAKPWYEPIYLGGVFQLEKGDRLSAEINRPDYL YFGESGQVYFGIIALGGGGSEPKSSDKTHTCPPCPAPEAAGGPSVFL FPPKPKDTLMISRTPEVTCVVVDVSHEDPEVKFNWYVDGVEVHNA KTKPREEQYNSTYRVVSVLTVLHQDWLNGKEYKCKVSNKALPASI EKTISKAKGQPREPQVYTLPPSRDELTKNQVSLTCLVKGFYPSDIAV EWESNGQPENNYKTTPPVLDSDGSFFLYSKLTVDKSRWQQGNVFS CSVMHEALHNHYTQKSLSLSPGK |
| Variant 6 (D143Y, A145G (N-term Fc) TNF-alpha variant fusion molecule) | 24 | EPKSSDKTHTCPPCPAPEAAGGPSVFLFPPKPKDTLMISRTPEVTCV VVDVSHEDPEVKFNWYVDGVEVHNAKTKPREEQYNSTYRVVSVL TVLHQDWLNGKEYKCKVSNKALPASIEKTISKAKGQPREPQVYTL PPSRDELTKNQVSLTCLVKGFYPSDIAVEWESNGQPENNYKTTPPV LDSDGSFFLYSKLTVDKSRWQQGNVFSCSVMHEALHNHYTQKSLS LSPGKGGGGSVRSSSRTPSDKPVAHVVANPQAEGQLQWLNRRAN ALLANGVELRDNQLVVPSEGLYLIYSQVLFKGQGCPSTHVLLTHTI SRIAVSYQTKVNLLSAIKSPCQRETPEGAEAKPWYEPIYLGGVFQLE KGDRLSAEINRPDYLYFGESGQVYFGIIALGGGGSSSRTPSDKPVAH VVANPQAEGQLQWLNRRANALLANGVELRDNQLVVPSEGLYLIY SQVLFKGQGCPSTHVLLTHTISRIAVSYQTKVNLLSAIKSPCQRETP EGAEAKPWYEPIYLGGVFQLEKGDRLSAEINRPDYLYFGESGQVYF GIIALGGGGSSSRTPSDKPVAHVVANPQAEGQLQWLNRRANALLA NGVELRDNQLVVPSEGLYLIYSQVLFKGQGCPSTHVLLTHTISRIAV SYQTKVNLLSAIKSPCQRETPEGAEAKPWYEPIYLGGVFQLEKGDR LSAEINRPDYLYFGESGQVYFGIIAL |
| Linker | 25 | GGGGG |
| Linker | 26 | GGSGGD |
| Linker | 27 | GGSGGE |
| Linker | 28 | GGGSGSGGGGS |
| Linker | 29 | GGGGGPGGGGP |
| Linker | 30 | GGGGGG |
| Linker | 31 | GGGGGGGG |
| Linker | 32 | EAAAK |
| Linker | 33 | AEAAAKEAAAKEAAAKEAAAKALEAEAAAKEAAAKEAAA KEAAAKA |
| Linker | 34 | AEAAAKEAAAKA |
| Linker | 35 | PAPA |
| Linker | 36 | VSQTSKLTRAETVFPDV |
| Linker | 37 | PLGLWA |
| Linker | 38 | RVLAEA |
| Linker | 39 | EDVVCCSMSY |
| Linker | 40 | GGIEGRGS |
| Linker | 41 | TRHRQPRGWE |
| Linker | 42 | AGNRVRRSVG |
| Linker | 43 | RRRRRRRRR |
| Linker | 44 | GFLG |

SEQUENCE LISTING

```
Sequence total quantity: 58
SEQ ID NO: 1                    moltype = AA   length = 157
FEATURE                         Location/Qualifiers
source                          1..157
                                mol_type = protein
                                organism = Homo sapiens
SEQUENCE: 1
VRSSSRTPSD KPVAHVVANP QAEGQLQWLN RRANALLANG VELRDNQLVV PSEGLYLIYS    60
QVLFKGQGCP STHVLLTHTI SRIAVSYQTK VNLLSAIKSP CQRETPEGAE AKPWYEPIYL   120
GGVFQLEKGD RLSAEINRPD YLDFAESGQV YFGIIAL                            157

SEQ ID NO: 2                    moltype = AA   length = 154
FEATURE                         Location/Qualifiers
source                          1..154
                                mol_type = protein
                                organism = synthetic construct
SEQUENCE: 2
SSRTPSDKPV AHVVANPQAE GQLQWLNRRA NALLANGVEL RDNQLVVPSE GLYLIYSQVL    60
FKGQGCPSTH VLLTHTISRI AVSYQTKVNL LSAIKSPCQR ETPEGAEAKP WYEPIYLGGV   120
FQLEKGDRLS AEINRPDYLD FAESGQVYFG IIAL                               154

SEQ ID NO: 3                    moltype = AA   length = 157
FEATURE                         Location/Qualifiers
source                          1..157
                                mol_type = protein
                                organism = synthetic construct
SEQUENCE: 3
VRSSSRTPSD KPVAHVVANP QAEGQLQWLN RRANALLANG VELRDNQLVV PSEGLYLIYS    60
QVLFKGQGCP STHVLLTHTI SRIAVSYQTK VNLLSAIKSP CQRETPEGAE AKPWYEPIYL   120
GGVFQLEKGD RLSAEINRPD YLNFAESGQV YFGIIAL                            157

SEQ ID NO: 4                    moltype = AA   length = 154
FEATURE                         Location/Qualifiers
source                          1..154
                                mol_type = protein
                                organism = synthetic construct
SEQUENCE: 4
SSRTPSDKPV AHVVANPQAE GQLQWLNRRA NALLANGVEL RDNQLVVPSE GLYLIYSQVL    60
FKGQGCPSTH VLLTHTISRI AVSYQTKVNL LSAIKSPCQR ETPEGAEAKP WYEPIYLGGV   120
FQLEKGDRLS AEINRPDYLN FAESGQVYFG IIAL                               154

SEQ ID NO: 5                    moltype = AA   length = 157
FEATURE                         Location/Qualifiers
source                          1..157
                                mol_type = protein
                                organism = synthetic construct
SEQUENCE: 5
VRSSSRTPSD KPVAHVVANP QAEGQLQWLN RRANALLANG VELRDNQLVV PSEGLYLIYS    60
QVLFKGQGCP STHVLLTHTI SRIAVSYQTK VNLLSAIKSP CQRETPEGAE AKPWYEPIYL   120
GGVFQLEKGD RLSAEINRPD YLDFRESGQV YFGIIAL                            157

SEQ ID NO: 6                    moltype = AA   length = 154
FEATURE                         Location/Qualifiers
source                          1..154
                                mol_type = protein
                                organism = synthetic construct
SEQUENCE: 6
SSRTPSDKPV AHVVANPQAE GQLQWLNRRA NALLANGVEL RDNQLVVPSE GLYLIYSQVL    60
FKGQGCPSTH VLLTHTISRI AVSYQTKVNL LSAIKSPCQR ETPEGAEAKP WYEPIYLGGV   120
FQLEKGDRLS AEINRPDYLD FRESGQVYFG IIAL                               154

SEQ ID NO: 7                    moltype = AA   length = 157
FEATURE                         Location/Qualifiers
source                          1..157
                                mol_type = protein
                                organism = synthetic construct
SEQUENCE: 7
VRSSSRTPSD KPVAHVVANP QAEGQLQWLN RRANALLANG VELRDNQLVV PSEGLYLIYS    60
QVLFKGQGCP STHVLLTHTI SRIAVSYQTK VNLLSAIKSP CQRETPEGAE AKPWYEPIYL   120
GGVFQLEKGD RLSAEINRPD YLNFRESGQV YFGIIAL                            157

SEQ ID NO: 8                    moltype = AA   length = 154
FEATURE                         Location/Qualifiers
source                          1..154
                                mol_type = protein
                                organism = synthetic construct
SEQUENCE: 8
SSRTPSDKPV AHVVANPQAE GQLQWLNRRA NALLANGVEL RDNQLVVPSE GLYLIYSQVL    60
```

```
FKGQGCPSTH VLLTHTISRI AVSYQTKVNL LSAIKSPCQR ETPEGAEAKP WYEPIYLGGV    120
FQLEKGDRLS AEINRPDYLN FRESGQVYFG IIAL                                154

SEQ ID NO: 9               moltype = AA  length = 157
FEATURE                    Location/Qualifiers
source                     1..157
                           mol_type = protein
                           organism = synthetic construct
SEQUENCE: 9
VRSSSRTPSD KPVAHVVANP QAEGQLQWLN RRANALLANG VELRDNQLVV PSEGLYLIYS     60
QVLFKGQGCP STHVLLTHTI SRIAVSYQTK VNLLSAIKSP CQRETPEGAE AKPWYEPIYL    120
GGVFQLEKGD RLSAEINRPD YLYFGESGQV YFGIIAL                             157

SEQ ID NO: 10              moltype = AA  length = 154
FEATURE                    Location/Qualifiers
source                     1..154
                           mol_type = protein
                           organism = synthetic construct
SEQUENCE: 10
SSRTPSDKPV AHVVANPQAE GQLQWLNRRA NALLANGVEL RDNQLVVPSE GLYLIYSQVL     60
FKGQGCPSTH VLLTHTISRI AVSYQTKVNL LSAIKSPCQR ETPEGAEAKP WYEPIYLGGV    120
FQLEKGDRLS AEINRPDYLY FGESGQVYFG IIAL                                154

SEQ ID NO: 11              moltype = AA  length = 475
FEATURE                    Location/Qualifiers
source                     1..475
                           mol_type = protein
                           organism = synthetic construct
SEQUENCE: 11
VRSSSRTPSD KPVAHVVANP QAEGQLQWLN RRANALLANG VELRDNQLVV PSEGLYLIYS     60
QVLFKGQGCP STHVLLTHTI SRIAVSYQTK VNLLSAIKSP CQRETPEGAE AKPWYEPIYL    120
GGVFQLEKGD RLSAEINRPD YLDFAESGQV YFGIIALGGG GSSSRTPSDK PVAHVVANPQ    180
AEGQLQWLNR RANALLANGV ELRDNQLVVP SEGLYLIYSQ VLFKGQGCPS THVLLTHTIS    240
RIAVSYQTKV NLLSAIKSPC QRETPEGAEA KPWYEPIYLG GVFQLEKGDR LSAEINRPDY    300
LDFAESGQVY FGIIALGGGG SSSRTPSDKP VAHVVANPQA EGQLQWLNRR ANALLANGVE    360
LRDNQLVVPS EGLYLIYSQV LFKGQGCPST HVLLTHTISR IAVSYQTKVN LLSAIKSPCQ    420
RETPEGAEAK PWYEPIYLGG VFQLEKGDRL SAEINRPDYL DFAESGQVYF GIIAL         475

SEQ ID NO: 12              moltype = AA  length = 475
FEATURE                    Location/Qualifiers
source                     1..475
                           mol_type = protein
                           organism = synthetic construct
SEQUENCE: 12
VRSSSRTPSD KPVAHVVANP QAEGQLQWLN RRANALLANG VELRDNQLVV PSEGLYLIYS     60
QVLFKGQGCP STHVLLTHTI SRIAVSYQTK VNLLSAIKSP CQRETPEGAE AKPWYEPIYL    120
GGVFQLEKGD RLSAEINRPD YLNFAESGQV YFGIIALGGG GSSSRTPSDK PVAHVVANPQ    180
AEGQLQWLNR RANALLANGV ELRDNQLVVP SEGLYLIYSQ VLFKGQGCPS THVLLTHTIS    240
RIAVSYQTKV NLLSAIKSPC QRETPEGAEA KPWYEPIYLG GVFQLEKGDR LSAEINRPDY    300
LNFAESGQVY FGIIALGGGG SSSRTPSDKP VAHVVANPQA EGQLQWLNRR ANALLANGVE    360
LRDNQLVVPS EGLYLIYSQV LFKGQGCPST HVLLTHTISR IAVSYQTKVN LLSAIKSPCQ    420
RETPEGAEAK PWYEPIYLGG VFQLEKGDRL SAEINRPDYL NFAESGQVYF GIIAL         475

SEQ ID NO: 13              moltype = AA  length = 475
FEATURE                    Location/Qualifiers
source                     1..475
                           mol_type = protein
                           organism = synthetic construct
SEQUENCE: 13
VRSSSRTPSD KPVAHVVANP QAEGQLQWLN RRANALLANG VELRDNQLVV PSEGLYLIYS     60
QVLFKGQGCP STHVLLTHTI SRIAVSYQTK VNLLSAIKSP CQRETPEGAE AKPWYEPIYL    120
GGVFQLEKGD RLSAEINRPD YLDFRESGQV YFGIIALGGG GSSSRTPSDK PVAHVVANPQ    180
AEGQLQWLNR RANALLANGV ELRDNQLVVP SEGLYLIYSQ VLFKGQGCPS THVLLTHTIS    240
RIAVSYQTKV NLLSAIKSPC QRETPEGAEA KPWYEPIYLG GVFQLEKGDR LSAEINRPDY    300
LDFRESGQVY FGIIALGGGG SSSRTPSDKP VAHVVANPQA EGQLQWLNRR ANALLANGVE    360
LRDNQLVVPS EGLYLIYSQV LFKGQGCPST HVLLTHTISR IAVSYQTKVN LLSAIKSPCQ    420
RETPEGAEAK PWYEPIYLGG VFQLEKGDRL SAEINRPDYL DFRESGQVYF GIIAL         475

SEQ ID NO: 14              moltype = AA  length = 475
FEATURE                    Location/Qualifiers
source                     1..475
                           mol_type = protein
                           organism = synthetic construct
SEQUENCE: 14
VRSSSRTPSD KPVAHVVANP QAEGQLQWLN RRANALLANG VELRDNQLVV PSEGLYLIYS     60
QVLFKGQGCP STHVLLTHTI SRIAVSYQTK VNLLSAIKSP CQRETPEGAE AKPWYEPIYL    120
GGVFQLEKGD RLSAEINRPD YLNFRESGQV YFGIIALGGG GSSSRTPSDK PVAHVVANPQ    180
AEGQLQWLNR RANALLANGV ELRDNQLVVP SEGLYLIYSQ VLFKGQGCPS THVLLTHTIS    240
RIAVSYQTKV NLLSAIKSPC QRETPEGAEA KPWYEPIYLG GVFQLEKGDR LSAEINRPDY    300
```

```
LNFRESGQVY FGIIALGGGG SSSRTPSDKP VAHVVANPQA EGQLQWLNRR ANALLANGVE  360
LRDNQLVVPS EGLYLIYSQV LFKGQGCPST HVLLTHTISR IAVSYQTKVN LLSAIKSPCQ  420
RETPEGAEAK PWYEPIYLGG VFQLEKGDRL SAEINRPDYL NFRESGQVYF GIIAL       475

SEQ ID NO: 15            moltype = AA   length = 475
FEATURE                  Location/Qualifiers
source                   1..475
                         mol_type = protein
                         organism = synthetic construct
SEQUENCE: 15
VRSSSRTPSD KPVAHVVANP QAEGQLQWLN RRANALLANG VELRDNQLVV PSEGLYLIYS  60
QVLFKGQGCP STHVLLTHTI SRIAVSYQTK VNLLSAIKSP CQRETPEGAE AKPWYEPIYL  120
GGVFQLEKGD RLSAEINRPD YLYFGESGQV YFGIIALGGG GSSSRTPSDK PVAHVVANPQ  180
AEGQLQWLNR RANALLANGV ELRDNQLVVP SEGLYLIYSQ VLFKGQGCPS THVLLTHTIS  240
RIAVSYQTKV NLLSAIKSPC QRETPEGAEA KPWYEPIYLG GVFQLEKGDR LSAEINRPDY  300
LYFGESGQVY FGIIALGGGG SSSRTPSDKP VAHVVANPQA EGQLQWLNRR ANALLANGVE  360
LRDNQLVVPS EGLYLIYSQV LFKGQGCPST HVLLTHTISR IAVSYQTKVN LLSAIKSPCQ  420
RETPEGAEAK PWYEPIYLGG VFQLEKGDRL SAEINRPDYL YFGESGQVYF GIIAL       475

SEQ ID NO: 16            moltype = AA   length = 5
FEATURE                  Location/Qualifiers
source                   1..5
                         mol_type = protein
                         organism = synthetic construct
SEQUENCE: 16
GGGGS                                                              5

SEQ ID NO: 17            moltype = AA   length = 232
FEATURE                  Location/Qualifiers
source                   1..232
                         mol_type = protein
                         organism = synthetic construct
SEQUENCE: 17
EPKSSDKTHT CPPCPAPEAA GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPASIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 18            moltype = AA   length = 712
FEATURE                  Location/Qualifiers
source                   1..712
                         mol_type = protein
                         organism = synthetic construct
SEQUENCE: 18
VRSSSRTPSD KPVAHVVANP QAEGQLQWLN RRANALLANG VELRDNQLVV PSEGLYLIYS  60
QVLFKGQGCP STHVLLTHTI SRIAVSYQTK VNLLSAIKSP CQRETPEGAE AKPWYEPIYL  120
GGVFQLEKGD RLSAEINRPD YLDFAESGQV YFGIIALGGG GSSSRTPSDK PVAHVVANPQ  180
AEGQLQWLNR RANALLANGV ELRDNQLVVP SEGLYLIYSQ VLFKGQGCPS THVLLTHTIS  240
RIAVSYQTKV NLLSAIKSPC QRETPEGAEA KPWYEPIYLG GVFQLEKGDR LSAEINRPDY  300
LDFAESGQVY FGIIALGGGG SSSRTPSDKP VAHVVANPQA EGQLQWLNRR ANALLANGVE  360
LRDNQLVVPS EGLYLIYSQV LFKGQGCPST HVLLTHTISR IAVSYQTKVN LLSAIKSPCQ  420
RETPEGAEAK PWYEPIYLGG VFQLEKGDRL SAEINRPDYL DFAESGQVYF GIIALGGGGS  480
EPKSSDKTHT CPPCPAPEAA GGPSVFLFPP KPKDTLMISR TPEVTCVVVD VSHEDPEVKF  540
NWYVDGVEVH NAKTKPREEQ YNSTYRVVSV LTVLHQDWLN GKEYKCKVSN KALPASIEKT  600
ISKAKGQPRE PQVYTLPPSR DELTKNQVSL TCLVKGFYPS DIAVEWESNG QPENNYKTTP  660
PVLDSDGSFF LYSKLTVDKS RWQQGNVFSC SVMHEALHNH YTQKSLSLSP GK          712

SEQ ID NO: 19            moltype = AA   length = 712
FEATURE                  Location/Qualifiers
source                   1..712
                         mol_type = protein
                         organism = synthetic construct
SEQUENCE: 19
VRSSSRTPSD KPVAHVVANP QAEGQLQWLN RRANALLANG VELRDNQLVV PSEGLYLIYS  60
QVLFKGQGCP STHVLLTHTI SRIAVSYQTK VNLLSAIKSP CQRETPEGAE AKPWYEPIYL  120
GGVFQLEKGD RLSAEINRPD YLNFAESGQV YFGIIALGGG GSSSRTPSDK PVAHVVANPQ  180
AEGQLQWLNR RANALLANGV ELRDNQLVVP SEGLYLIYSQ VLFKGQGCPS THVLLTHTIS  240
RIAVSYQTKV NLLSAIKSPC QRETPEGAEA KPWYEPIYLG GVFQLEKGDR LSAEINRPDY  300
LNFAESGQVY FGIIALGGGG SSSRTPSDKP VAHVVANPQA EGQLQWLNRR ANALLANGVE  360
LRDNQLVVPS EGLYLIYSQV LFKGQGCPST HVLLTHTISR IAVSYQTKVN LLSAIKSPCQ  420
RETPEGAEAK PWYEPIYLGG VFQLEKGDRL SAEINRPDYL NFAESGQVYF GIIALGGGGS  480
EPKSSDKTHT CPPCPAPEAA GGPSVFLFPP KPKDTLMISR TPEVTCVVVD VSHEDPEVKF  540
NWYVDGVEVH NAKTKPREEQ YNSTYRVVSV LTVLHQDWLN GKEYKCKVSN KALPASIEKT  600
ISKAKGQPRE PQVYTLPPSR DELTKNQVSL TCLVKGFYPS DIAVEWESNG QPENNYKTTP  660
PVLDSDGSFF LYSKLTVDKS RWQQGNVFSC SVMHEALHNH YTQKSLSLSP GK          712

SEQ ID NO: 20            moltype = AA   length = 712
FEATURE                  Location/Qualifiers
source                   1..712
```

```
                              mol_type = protein
                              organism = synthetic construct
SEQUENCE: 20
VRSSSRTPSD KPVAHVVANP QAEGQLQWLN RRANALLANG VELRDNQLVV PSEGLYLIYS     60
QVLFKGQGCP STHVLLTHTI SRIAVSYQTK VNLLSAIKSPC QRETPEGAEA AKPWYEPIYL   120
GGVFQLEKGD RLSAEINRPD YLDFRESGQV YFGIIALGGG GSSSRTPSDK PVAHVVANPQ   180
AEGQLQWLNR RANALLANGV ELRDNQLVVP SEGLYLIYSQ VLFKGQGCPS THVLLTHTIS   240
RIAVSYQTKV NLLSAIKSPC QRETPEGAEA KPWYEPIYLG GVFQLEKGDR LSAEINRPDY   300
LDFRESGQVY FGIIALGGGG SSSRTPSDKP VAHVVANPQA EGQLQWLNRR ANALLANGVE   360
LRDNQLVVPS EGLYLIYSQV LFKGQGCPST HVLLTHTISR IAVSYQTKVN LLSAIKSPCQ   420
RETPEGAEAK PWYEPIYLGG VFQLEKGDRL SAEINRPDYL DFRESGQVYF GIIALGGGGS   480
EPKSSDKTHT CPPCPAPEAA GGPSVFLFPP KPKDTLMISR TPEVTCVVVD VSHEDPEVKF   540
NWYVDGVEVH NAKTKPREEQ YNSTYRVVSV LTVLHQDWLN GKEYKCKVSN KALPASIEKT   600
ISKAKGQPRE PQVYTLPPSR DELTKNQVSL TCLVKGFYPS DIAVEWESNG QPENNYKTTP   660
PVLDSDGSFF LYSKLTVDKS RWQQGNVFSC SVMHEALHNH YTQKSLSLSP GK           712

SEQ ID NO: 21             moltype = AA  length = 712
FEATURE                   Location/Qualifiers
source                    1..712
                          mol_type = protein
                          organism = synthetic construct
SEQUENCE: 21
VRSSSRTPSD KPVAHVVANP QAEGQLQWLN RRANALLANG VELRDNQLVV PSEGLYLIYS     60
QVLFKGQGCP STHVLLTHTI SRIAVSYQTK VNLLSAIKSP CQRETPEGAE AKPWYEPIYL   120
GGVFQLEKGD RLSAEINRPD YLNFRESGQV YFGIIALGGG GSSSRTPSDK PVAHVVANPQ   180
AEGQLQWLNR RANALLANGV ELRDNQLVVP SEGLYLIYSQ VLFKGQGCPS THVLLTHTIS   240
RIAVSYQTKV NLLSAIKSPC QRETPEGAEA KPWYEPIYLG GVFQLEKGDR LSAEINRPDY   300
LNFRESGQVY FGIIALGGGG SSSRTPSDKP VAHVVANPQA EGQLQWLNRR ANALLANGVE   360
LRDNQLVVPS EGLYLIYSQV LFKGQGCPST HVLLTHTISR IAVSYQTKVN LLSAIKSPCQ   420
RETPEGAEAK PWYEPIYLGG VFQLEKGDRL SAEINRPDYL NFRESGQVYF GIIALGGGGS   480
EPKSSDKTHT CPPCPAPEAA GGPSVFLFPP KPKDTLMISR TPEVTCVVVD VSHEDPEVKF   540
NWYVDGVEVH NAKTKPREEQ YNSTYRVVSV LTVLHQDWLN GKEYKCKVSN KALPASIEKT   600
ISKAKGQPRE PQVYTLPPSR DELTKNQVSL TCLVKGFYPS DIAVEWESNG QPENNYKTTP   660
PVLDSDGSFF LYSKLTVDKS RWQQGNVFSC SVMHEALHNH YTQKSLSLSP GK           712

SEQ ID NO: 22             moltype = AA  length = 712
FEATURE                   Location/Qualifiers
source                    1..712
                          mol_type = protein
                          organism = synthetic construct
SEQUENCE: 22
EPKSSDKTHT CPPCPAPEAA GGPSVFLFPP KPKDTLMISR TPEVTCVVVD VSHEDPEVKF     60
NWYVDGVEVH NAKTKPREEQ YNSTYRVVSV LTVLHQDWLN GKEYKCKVSN KALPASIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GKGGGGSVRS   240
SSRTPSDKPV AHVVANPQAE GQLQWLNRRA NALLANGVEL RDNQLVVPSE GLYLIYSQVL   300
FKGQGCPSTH VLLTHTISRI AVSYQTKVNL LSAIKSPCQR ETPEGAEAKP WYEPIYLGGV   360
FQLEKGDRLS AEINRPDYLN FRESGQVYFG IIALGGGGSS SRTPSDKPVA HVVANPQAEG   420
QLQWLNRRAN ALLANGVELR DNQLVVPSEG LYLIYSQVLF KGQGCPSTHV LLTHTISRIA   480
VSYQTKVNLL SAIKSPCQRE TPEGAEAKPW YEPIYLGGVF QLEKGDRLSA EINRPDYLNF   540
RESGQVYFGI IALGGGGSSS RTPSDKPVAH VVANPQAEGQ LQWLNRRANA LLANGVELRD   600
NQLVVPSEGL YLIYSQVLFK GQGCPSTHVL LTHTISRIAV SYQTKVNLLS AIKSPCQRET   660
PEGAEAKPWY EPIYLGGVFQ LEKGDRLSAE INRPDYLNFR ESGQVYFGII AL            712

SEQ ID NO: 23             moltype = AA  length = 712
FEATURE                   Location/Qualifiers
source                    1..712
                          mol_type = protein
                          organism = synthetic construct
SEQUENCE: 23
VRSSSRTPSD KPVAHVVANP QAEGQLQWLN RRANALLANG VELRDNQLVV PSEGLYLIYS     60
QVLFKGQGCP STHVLLTHTI SRIAVSYQTK VNLLSAIKSP CQRETPEGAE AKPWYEPIYL   120
GGVFQLEKGD RLSAEINRPD YLYFGESGQV YFGIIALGGG GSSSRTPSDK PVAHVVANPQ   180
AEGQLQWLNR RANALLANGV ELRDNQLVVP SEGLYLIYSQ VLFKGQGCPS THVLLTHTIS   240
RIAVSYQTKV NLLSAIKSPC QRETPEGAEA KPWYEPIYLG GVFQLEKGDR LSAEINRPDY   300
LYFGESGQVY FGIIALGGGG SSSRTPSDKP VAHVVANPQA EGQLQWLNRR ANALLANGVE   360
LRDNQLVVPS EGLYLIYSQV LFKGQGCPST HVLLTHTISR IAVSYQTKVN LLSAIKSPCQ   420
RETPEGAEAK PWYEPIYLGG VFQLEKGDRL SAEINRPDYL YFGESGQVYF GIIALGGGGS   480
EPKSSDKTHT CPPCPAPEAA GGPSVFLFPP KPKDTLMISR TPEVTCVVVD VSHEDPEVKF   540
NWYVDGVEVH NAKTKPREEQ YNSTYRVVSV LTVLHQDWLN GKEYKCKVSN KALPASIEKT   600
ISKAKGQPRE PQVYTLPPSR DELTKNQVSL TCLVKGFYPS DIAVEWESNG QPENNYKTTP   660
PVLDSDGSFF LYSKLTVDKS RWQQGNVFSC SVMHEALHNH YTQKSLSLSP GK           712

SEQ ID NO: 24             moltype = AA  length = 712
FEATURE                   Location/Qualifiers
source                    1..712
                          mol_type = protein
                          organism = synthetic construct
SEQUENCE: 24
```

```
EPKSSDKTHT CPPCPAPEAA GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPASIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GKGGGGSVRS   240
SSRTPSDKPV AHVVANPQAE GQLQWLNRRA NALLANGVEL RDNQLVVPSE GLYLIYSQVL   300
FKGQGCPSTH VLLTHTISRI AVSYQTKVNL LSAIKSPCQR ETPEGAEAKP WYEPIYLGGV   360
FQLEKGDRLS AEINRPDYLY FGESGQVYFG IIALGGGGSS SRTPSDKPVA HVVANPQAEG   420
QLQWLNRRAN ALLANGVELR DNQLVVPSEG LYLIYSQVLF KGQGCPSTHV LLTHTISRIA   480
VSYQTKVNLL SAIKSPCQRE TPEGAEAKPW YEPIYLGGVF QLEKGDRLSA EINRPDYLYF   540
GESGQVYFGI IALGGGGSSS RTPSDKPVAH VVANPQAEGQ LQWLNRRANA LLANGVELRD   600
NQLVVPSEGL YLIYSQVLFK GQGCPSTHVL LTHTISRIAV SYQTKVNLLS AIKSPCQRET   660
PEGAEAKPWY EPIYLGGVFQ LEKGDRLSAE INRPDYLYFG ESGQVYFGII AL           712

SEQ ID NO: 25          moltype = AA   length = 5
FEATURE                Location/Qualifiers
source                 1..5
                       mol_type = protein
                       organism = synthetic construct
SEQUENCE: 25
GGGGG                                                                 5

SEQ ID NO: 26          moltype = AA   length = 6
FEATURE                Location/Qualifiers
source                 1..6
                       mol_type = protein
                       organism = synthetic construct
SEQUENCE: 26
GGSGGD                                                                6

SEQ ID NO: 27          moltype = AA   length = 6
FEATURE                Location/Qualifiers
source                 1..6
                       mol_type = protein
                       organism = synthetic construct
SEQUENCE: 27
GGSGGE                                                                6

SEQ ID NO: 28          moltype = AA   length = 11
FEATURE                Location/Qualifiers
source                 1..11
                       mol_type = protein
                       organism = synthetic construct
SEQUENCE: 28
GGGSGSGGGG S                                                         11

SEQ ID NO: 29          moltype = AA   length = 11
FEATURE                Location/Qualifiers
source                 1..11
                       mol_type = protein
                       organism = synthetic construct
SEQUENCE: 29
GGGGGPGGGG P                                                         11

SEQ ID NO: 30          moltype = AA   length = 6
FEATURE                Location/Qualifiers
source                 1..6
                       mol_type = protein
                       organism = synthetic construct
SEQUENCE: 30
GGGGGG                                                                6

SEQ ID NO: 31          moltype = AA   length = 8
FEATURE                Location/Qualifiers
source                 1..8
                       mol_type = protein
                       organism = synthetic construct
SEQUENCE: 31
GGGGGGGG                                                              8

SEQ ID NO: 32          moltype = AA   length = 5
FEATURE                Location/Qualifiers
source                 1..5
                       mol_type = protein
                       organism = synthetic construct
SEQUENCE: 32
EAAAK                                                                 5

SEQ ID NO: 33          moltype = AA   length = 46
FEATURE                Location/Qualifiers
```

```
                        -continued source                  1..46
                        mol_type = protein
                        organism = synthetic construct
SEQUENCE: 33
AEAAAKEAAA KEAAAKEAAA KALEAEAAAK EAAAKEAAAK EAAAKA           46

SEQ ID NO: 34           moltype = AA   length = 12
FEATURE                 Location/Qualifiers
source                  1..12
                        mol_type = protein
                        organism = synthetic construct
SEQUENCE: 34
AEAAAKEAAA KA                                                12

SEQ ID NO: 35           moltype = AA   length = 4
FEATURE                 Location/Qualifiers
source                  1..4
                        mol_type = protein
                        organism = synthetic construct
SEQUENCE: 35
PAPA                                                         4

SEQ ID NO: 36           moltype = AA   length = 17
FEATURE                 Location/Qualifiers
source                  1..17
                        mol_type = protein
                        organism = synthetic construct
SEQUENCE: 36
VSQTSKLTRA ETVFPDV                                           17

SEQ ID NO: 37           moltype = AA   length = 6
FEATURE                 Location/Qualifiers
source                  1..6
                        mol_type = protein
                        organism = synthetic construct
SEQUENCE: 37
PLGLWA                                                       6

SEQ ID NO: 38           moltype = AA   length = 6
FEATURE                 Location/Qualifiers
source                  1..6
                        mol_type = protein
                        organism = synthetic construct
SEQUENCE: 38
RVLAEA                                                       6

SEQ ID NO: 39           moltype = AA   length = 10
FEATURE                 Location/Qualifiers
source                  1..10
                        mol_type = protein
                        organism = synthetic construct
SEQUENCE: 39
EDVVCCSMSY                                                   10

SEQ ID NO: 40           moltype = AA   length = 8
FEATURE                 Location/Qualifiers
source                  1..8
                        mol_type = protein
                        organism = synthetic construct
SEQUENCE: 40
GGIEGRGS                                                     8

SEQ ID NO: 41           moltype = AA   length = 10
FEATURE                 Location/Qualifiers
source                  1..10
                        mol_type = protein
                        organism = synthetic construct
SEQUENCE: 41
TRHRQPRGWE                                                   10

SEQ ID NO: 42           moltype = AA   length = 10
FEATURE                 Location/Qualifiers
source                  1..10
                        mol_type = protein
                        organism = synthetic construct
SEQUENCE: 42
AGNRVRRSVG                                                   10

SEQ ID NO: 43           moltype = AA   length = 9
```

```
FEATURE                 Location/Qualifiers
source                  1..9
                        mol_type = protein
                        organism = synthetic construct
SEQUENCE: 43
RRRRRRRRR                                                                      9

SEQ ID NO: 44           moltype = AA  length = 4
FEATURE                 Location/Qualifiers
source                  1..4
                        mol_type = protein
                        organism = synthetic construct
SEQUENCE: 44
GFLG                                                                           4

SEQ ID NO: 45           moltype = AA  length = 4
FEATURE                 Location/Qualifiers
source                  1..4
                        mol_type = protein
                        organism = synthetic construct
SEQUENCE: 45
GGGG                                                                           4

SEQ ID NO: 46           moltype = AA  length = 5
FEATURE                 Location/Qualifiers
source                  1..5
                        mol_type = protein
                        organism = synthetic construct
SEQUENCE: 46
DKTHT                                                                          5

SEQ ID NO: 47           moltype = AA  length = 40
FEATURE                 Location/Qualifiers
source                  1..40
                        mol_type = protein
                        organism = synthetic construct
VARIANT                 5..40
                        note = GS repeats may be deleted
SEQUENCE: 47
GSGSGSGSGS GSGSGSGSGS GSGSGSGSGS GSGSGSGSGS                                    40

SEQ ID NO: 48           moltype = AA  length = 60
FEATURE                 Location/Qualifiers
source                  1..60
                        mol_type = protein
                        organism = synthetic construct
VARIANT                 7..60
                        note = GGS repeats may be deleted
SEQUENCE: 48
GGSGGSGGSG GSGGSGGSGG SGGSGGSGGS GGSGGSGGSG GSGGSGGSGG SGGSGGSGGS              60

SEQ ID NO: 49           moltype = AA  length = 80
FEATURE                 Location/Qualifiers
source                  1..80
                        mol_type = protein
                        organism = synthetic construct
VARIANT                 9..80
                        note = GGGS repeats may be deleted
SEQUENCE: 49
GGGSGGGSGG GSGGGSGGGS GGGSGGGSGG GSGGGSGGGS GGGSGGGSGG GSGGGSGGGS              60
GGGSGGGSGG GSGGGSGGGS                                                         80

SEQ ID NO: 50           moltype = AA  length = 100
FEATURE                 Location/Qualifiers
source                  1..100
                        mol_type = protein
                        organism = synthetic construct
VARIANT                 11..100
                        note = GGGGS repeats may be deleted
SEQUENCE: 50
GGGGSGGGGS GGGGSGGGGS GGGGSGGGGS GGGGSGGGGS GGGGSGGGGS GGGGSGGGGS              60
GGGGSGGGGS GGGGSGGGGS GGGGSGGGGS GGGGSGGGGS                                   100

SEQ ID NO: 51           moltype = AA  length = 20
FEATURE                 Location/Qualifiers
source                  1..20
                        mol_type = protein
                        organism = synthetic construct
VARIANT                 3..20
```

```
                         note = Residue may be deleted
SEQUENCE: 51
GGGGGGGGGG GGGGGGGGGG                                               20

SEQ ID NO: 52            moltype = AA   length = 30
FEATURE                  Location/Qualifiers
source                   1..30
                         mol_type = protein
                         organism = synthetic construct
VARIANT                  11..30
                         note = GGGGG repeats may be deleted
SEQUENCE: 52
GGGGGGGGGG GGGGGGGGGG GGGGGGGGGG                                    30

SEQ ID NO: 53            moltype = AA   length = 36
FEATURE                  Location/Qualifiers
source                   1..36
                         mol_type = protein
                         organism = synthetic construct
VARIANT                  13..36
                         note = GGSGGD repeats may be deleted
SEQUENCE: 53
GGSGGDGGSG GDGGSGGDGG SGGDGGSGGD GGSGGD                             36

SEQ ID NO: 54            moltype = AA   length = 36
FEATURE                  Location/Qualifiers
source                   1..36
                         mol_type = protein
                         organism = synthetic construct
VARIANT                  13..36
                         note = GGSGGE repeats may be deleted
SEQUENCE: 54
GGSGGEGGSG GEGGSGGEGG SGGEGGSGGE GGSGGE                             36

SEQ ID NO: 55            moltype = AA   length = 33
FEATURE                  Location/Qualifiers
source                   1..33
                         mol_type = protein
                         organism = synthetic construct
VARIANT                  12..33
                         note = GGGSGSGGGGS repeats may be deleted
SEQUENCE: 55
GGGSGSGGGG SGGGSGSGGG GSGGGGSGSGG GGS                               33

SEQ ID NO: 56            moltype = AA   length = 33
FEATURE                  Location/Qualifiers
source                   1..33
                         mol_type = protein
                         organism = synthetic construct
VARIANT                  12..33
                         note = GGGGGPGGGGP repeats may be deleted
SEQUENCE: 56
GGGGGPGGGG PGGGGGPGGG GPGGGGGPGG GGP                                33

SEQ ID NO: 57            moltype = AA   length = 15
FEATURE                  Location/Qualifiers
source                   1..15
                         mol_type = protein
                         organism = synthetic construct
VARIANT                  6..15
                         note = EAAAK repeats may be deleted
SEQUENCE: 57
EAAAKEAAAK EAAAK                                                    15

SEQ ID NO: 58            moltype = AA   length = 68
FEATURE                  Location/Qualifiers
source                   1..68
                         mol_type = protein
                         organism = synthetic construct
VARIANT                  21..68
                         note = AP repeats may be deleted
SEQUENCE: 58
APAPAPAPAP APAPAPAPAP APAPAPAPAP APAPAPAPAP APAPAPAPAP APAPAPAPAP   60
APAPAPAP                                                            68
```

The invention claimed is:

1. A TNF-alpha variant molecule comprising one or more TNF-alpha variants, wherein the one or more TNF-alpha variants comprises a polypeptide that specifically binds TNFR2 and comprises the amino acid sequence of SEQ ID NO: 9 or SEQ ID NO: 10.

2. The TNF-alpha variant molecule of claim 1, wherein the TNF-alpha variant molecule comprises a plurality of TNF-alpha variants, optionally at least three TNF-alpha variants.

3. The TNF-alpha variant molecule of claim 1, wherein the TNF-alpha variant molecule comprises at least three TNF-alpha variants, wherein one of the three TNF-alpha variants comprises a polypeptide comprising the amino acid sequence of SEQ ID NO: 9 and two of the three TNF-alpha variants comprise a polypeptide comprising the amino acid sequence of SEQ ID NO: 10.

4. The TNF-alpha variant molecule of claim 3, wherein the TNF-alpha variant molecule comprises a linker between the TNF-alpha variants, optionally a linker comprising the amino acid sequence of SEQ ID NO: 16.

5. The TNF-alpha variant molecule of claim 3, wherein the TNF-alpha variant molecule comprises one or more linkers.

6. The TNF-alpha variant molecule of claim 1, wherein the TNF-alpha variant molecule comprises the amino acid sequence of SEQ ID NO: 15.

7. A nucleic acid encoding the TNF-alpha variant molecule of claim 1.

8. At least one expression vector comprising the nucleic acid of claim 7.

9. At least one host cell comprising the nucleic acid of claim 7.

10. At least one host cell that expresses the TNF-alpha variant molecule of claim 1.

11. A pharmaceutical composition comprising the TNF-alpha variant molecule of claim 1 and a pharmaceutically acceptable carrier.

12. A TNF-alpha variant fusion molecule comprising from N-terminus to C-terminus:
a) a first TNF-alpha variant comprising a polypeptide comprising the amino acid sequence of SEQ ID NO: 9;
b) a first linker;
c) a second TNF-alpha variant comprising a polypeptide comprising the amino acid sequence of SEQ ID NO: 10;
d) a second linker;
e) a third TNF-alpha variant comprising a polypeptide comprising the amino acid sequence of SEQ ID NO: 10;
f) a third linker; and
g) a Fc domain.

13. The TNF-alpha variant fusion molecule of claim 12, wherein the Fc domain is a human IgG1 isotype.

14. The TNF-alpha variant fusion molecule of claim 13, wherein the human IgG1 isotype Fc domain comprises a L234A mutation and a L235A mutation.

15. The TNF-alpha variant fusion molecule of claim 13, wherein the human IgG1 isotype Fc domain comprises a P331S mutation.

16. The TNF-alpha variant fusion molecule of claim 13, wherein the Fc domain comprises the amino acid sequence of SEQ ID NO: 17.

17. The TNF-alpha variant fusion molecule of claim 16, wherein the TNF-alpha variant fusion molecule:
a) binds to TNFR2 with over a 20 fold affinity compared TNFR1, optionally as determined by bio-layer interferometry;
b) binds to and activates TNFR2 with an EC50 of at least about 5 ng/mL, optionally as determined by flow cytometry using human TNFR2 expressing cells and human TNFR2 non-expressing cells;
c) has increased Tm compared to SEQ ID NO: 21 or SEQ ID NO: 22, optionally as determined by differential scanning fluorimetry (DSF);
d) has increased serum stability compared to SEQ ID NO: 21 or SEQ ID NO: 22, optionally as determined by Size Exclusion Chromatography; or
e) any combinations of a)-d).

18. A TNF-alpha variant fusion molecule comprising the amino acid sequence of SEQ ID NO: 23.

19. A nucleic acid encoding the TNF-alpha variant fusion molecule of claim 18.

20. At least one expression vector comprising the nucleic acid of claim 19.

21. At least one host cell comprising the nucleic acid of claim 19.

22. At least one host cell that expresses the TNF-alpha variant fusion molecule of claim 18.

23. A pharmaceutical composition comprising the TNF-alpha variant fusion molecule of claim 18 and a pharmaceutically acceptable carrier.

* * * * *